(12) United States Patent
Hoffee et al.

(10) Patent No.: US 10,000,566 B2
(45) Date of Patent: *Jun. 19, 2018

(54) ANTI-CD33 ANTIBODIES AND METHODS FOR TREATMENT OF ACUTE MYELOID LEUKEMIA USING THE SAME

(71) Applicant: IMMUNOGEN INC., Waltham, MA (US)

(72) Inventors: Mary G. Hoffee, Brookline, MA (US); Daniel Tavares, Natick, MA (US); Robert J. Lutz, Wayland, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/154,115

(22) Filed: May 13, 2016

(65) Prior Publication Data
US 2016/0362490 A1 Dec. 15, 2016

Related U.S. Application Data

(60) Continuation of application No. 14/249,602, filed on Apr. 10, 2014, now Pat. No. 9,359,442, which is a division of application No. 13/680,614, filed on Nov. 19, 2012, now Pat. No. 8,747,851, which is a division of application No. 13/019,478, filed on Feb. 2, 2011, now Pat. No. 8,337,855, which is a continuation of application No. 12/358,832, filed on Jan. 23, 2009, now abandoned, which is a continuation of application No. 10/700,632, filed on Nov. 5, 2003, now Pat. No. 7,557,189.

(60) Provisional application No. 60/424,332, filed on Nov. 7, 2002.

(51) Int. Cl.
| | | |
|---|---|---|
| C07K 16/28 | (2006.01) | |
| A61K 39/395 | (2006.01) | |
| A61K 47/68 | (2017.01) | |
| A61K 39/00 | (2006.01) | |

(52) U.S. Cl.
CPC ...... *C07K 16/2803* (2013.01); *A61K 39/3955* (2013.01); *A61K 47/6803* (2017.08); *A61K 47/6849* (2017.08); *C07K 16/2896* (2013.01); *A61K 2039/505* (2013.01); *C07K 2317/24* (2013.01); *C07K 2317/56* (2013.01); *C07K 2317/565* (2013.01); *C07K 2317/70* (2013.01); *C07K 2317/92* (2013.01)

(58) Field of Classification Search
CPC ............ C07K 16/2896; C07K 2317/24; C07K 2317/565; C07K 2317/56; A61K 47/6849
USPC .................................................... 424/133.1
See application file for complete search history.

(56) References Cited

U.S. PATENT DOCUMENTS

| | | | |
|---|---|---|---|
| 5,730,982 | A | 3/1998 | Scheinberg |
| 6,417,337 | B1 | 7/2002 | Anderson et al. |
| 6,759,045 | B2 | 7/2004 | Goldenberg et al. |
| 7,557,189 | B2 | 7/2009 | Hoffee et al. |
| 8,337,855 | B2* | 12/2012 | Hoffee ............... C07K 16/2803 424/173.1 |
| 8,747,851 | B2 | 6/2014 | Hoffee et al. |
| 2002/0052479 | A1 | 5/2002 | Anderson et al. |
| 2005/0287164 | A1 | 12/2005 | Patti et al. |
| 2006/0233814 | A1* | 10/2006 | Goldmakher ...... A61K 31/5383 424/178.1 |
| 2010/0028346 | A1* | 2/2010 | Lutz ..................... A61K 31/198 424/135.1 |
| 2017/0080102 | A1* | 3/2017 | Whiteman ....... A61K 47/48384 |

FOREIGN PATENT DOCUMENTS

| | | |
|---|---|---|
| ES | 2152216 T3 | 2/2001 |
| WO | 9410332 A1 | 5/1994 |

OTHER PUBLICATIONS

Supplemental European Search Report corresponding to European Application No. 03 77 9105, dated Jun. 10, 2008.
Lutz et al., "Eradication of acute myeloid leukemia tumor xenograft by an anti CD33-DM1 immunoconjugate," Proceedings of the Annual Meeting of the American Association for Cancer Research, New York, NY, 43:912 (Mar. 1, 2002).
Monneret et al., "Ciblage de molecules antitumorales par les anticorps monoclonaux," Bulletin du Cancer, Edition Scientifiques, Elsevier, Paris, France, 87(11):829-838 (Jan. 1, 2000).
Roy et al., "Anti-MY9-Blocked-Ricin: An Immunotoxin for Selective Targeting of Acute Myeloid Leukemia Cells", *Blood*, The American Society of Hematology, 77:2404-2412 (Jun. 1, 1991).
Smith, "Technology evaluation: C242-DM1, ImmunoGen Inc", Current Opinion in Molecular Therapeutics, 2001, 198-203, 3(2), PharmaPress Ltd.

(Continued)

*Primary Examiner* — Lynn A Bristol
(74) *Attorney, Agent, or Firm* — McCarter & English, LLP; Yu Lu; Xin Zhang

(57) ABSTRACT

The present invention relates to antibodies that bind CD33. More particularly, the invention relates to anti-CD33 antibodies, fragments and homologues of these antibodies, humanized and resurfaced versions of these antibodies, functional equivalents and improved versions of these antibodies, immunoconjugates and compositions comprising these antibodies, and the uses of same in diagnostic, research and therapeutic applications. The invention also relates to a polynucleotide encoding these antibodies, vectors comprising the polynucleotides, host cells transformed with polynucleotides and methods of producing these antibodies.

18 Claims, 29 Drawing Sheets

(56) References Cited

OTHER PUBLICATIONS

Goldmacher et al., "Specific cytotoxicity of an anti-CD33-DM1 tumor-activated pro-drug for cultured cell lines expressing CD33", *Proceedings of the American Association for Cancer Research*, 43:254 (2002).
Biocentury Part II, 9(48): B1-B22 (Oct. 29, 2001).
Favaloro et al., "Characterization of monoclonal antibodies to the human myeloid-differentiation antigen, gp67" (CD-33), Dis Markers, 5(4):215-225 (1987), Abstract.
Kasai et al., "Introduction: Immunology," Kodansha, pp. 41-42 (Jul. 10, 1989).
Ecuadorian Office Action for Patent No. SP-05-5831-PCT, dated Feb. 10, 2011.
ES2152216, Cancer Research.
Wu et al., AAC04264.1, [Mus musculus] NCBI 1998, "Cloning and Sequencing of VH gene of monoclonal antibody against beet necrotic yellow vein virus", Unpublished; and Parra et al., Blast Report date Mar. 18, 2011, Query ID lcl57959, "All non-redundant GenBank CDS translations+PDB+SwissProt+PIR+PRF excluding Environmental samples from WGS projects".
gb\AAA99393.1\immunoglobulin kappa chain [Homo sapiens], 1996.
Schmaljohn et al., CAB44483.1, [Homo sapiens] 1999, linear PRI Jun. 7, 1999, "Production and Characterization of human monoclonal antibody Fab fragments to vaccinia virus from phage-display Combinatorial library", *Virology*, 258(1):189-200 (1999).
Reed et al., AAF76155.1, [Mus musculus], NCBI 2000, Differing sensitivities to negative selection exhibited by auto-reactive primary response and memory B cells, Unpublished; and Parra et al., Blast Report date Mar. 18, 2011, Query ID lcl43769, "All non-redundant GenBank CDS translations+PDB+SwissProt+PIR+PRF excluding Environmental samples from WGS projects".
Fitzsimons et al., AAC13704.1, [Mus musculus] NCBI 1998, "Diverse lupus like autoantibodies recovered from non autoimmune Ig-transgenic mice", *J. Am. Soc., Nephrol.*, 8:A2112 (1997); and Parra et al., Blast Report date Mar. 18, 2011, Query ID lcl27242, "All non-redundant GenBank CDS translations+PDB+SwissProt+PIR+PRF excluding Environmental samples from WGS projects".
Leung et al., AAB34246.1, [Mus musculus], NCBI 1995, linear ROD Sep. 26, 1995, Chimerization of LL2, a rapidly internalizing antibody specific for B cell Lymphoma; *Hybridoma*, 13(6):469-476 (1994); and Parra et al., Blast Report date Mar. 18, 2011, Query ID lcl27242, "All non-redundant GenBank CDS translations+PDB+SwissProt+PIR+PRF excluding Environmental samples from WGS projects".
Office Action for Chinese Application No. 201210362462.9 dated Dec. 12, 2013.
Sievers et al., "Efficacy and Safety of Gemtuzumab Ozogamicin in Patients with CD33-Positive Acute Myeloid Leukemia in First Relapse", Journal of Clinical Oncology, 19(13):3244-3254 (2001).
Amit et al., Science, 233:747-753 (1986).
Bendig, Methods: A Companion to Methods in Enzymology, 8:83-93 (1995).
Casset et al., Biochemical and Biophysical Research Communication, 307:198-205 (2003).
Coleman, Research in Immunology, 145:33-36 (1994).
Bridges et al, AAA99393.1, [Homo sapiens] 1996, linear PRI May 10, 1996, "Somatic mutation and CDR3 lengths of immunoglobulin kappa light chains expressed in patients with rheumatoid arthritis and in normal individuals", J. Clin. Invest., 96(2):831-841 (1995).
CML NewyBytes, Oct. 24, 2001, www.cmlsupport.com/cmlnewsbytesarchives2.htm.
Gawinowicz et al, *J. of Immunology*, 147(3):915-920 (1991).
Griffin et al, *Leukemia Res.*, 8:521-534 (1984).
Larussa et al, *Exp. Hematol.*, 20:442-448 (1992).
MacCallum et al., *J. Mol. Biol.*, 262:732-745 (1996).
Mason et al., Eds., Leucocyte Typing VII White Cell Differentiation Antigens, Oxford University Press, pp. 777-778 (2002).
Paul, *Fundamental Immunology*, 3$^{rd}$ Edition, pp. 292-295 (1993).
R&D Focus Drug News (Nov. 12, 2001).
Rudikoff et al, *Proc. Natl. Acad. Sci., USA*, 79(6):1979-1983 (1982).
Sabbath et al, *J. Clin. Invest.*, 75:746-753 (1985).
Van der Velden et al., "Targeting of the CD33-calicheamicin immunoconjugate Mylotarg (CMA-676) in acute myeloid leukemia: in vivo and in vitro saturation and internalization by leukemic and normal myeloid cells", Neoplasia, *Blood*, 97(10):3197-3204 (2001).
Weitzhandler et al., *J. of Pharmaceutical Sciences*, 83(12):1670-1675 (1994).
Wu et al., *Nature Biotechnology*, 23:9 (2005).
Zaho et al., "New Water Soluble CC-1065 Analog Prodrugs: Design, Synthesis and Evaluation", American Chemical Society 224th National Meeting, pp. 18-22 (Aug. 2002).
Jurcic, Curr. Hematol. Malig. Rep., 7:65-73 (2012).
Morris, Expert Rev. Molec. Med., 11:e29 (2009), Abstract Only.

* cited by examiner

Figure 2

My9-6 Light Chain Signal Sequence Degenerate Primers

| Name | Sequence | SEQ ID NO: |
|---|---|---|
| Leaddeg1 | TTTTGATTCTGCTGTGGGTGTCCGGNACNTGYGG | 17 |
| Leaddeg2 | TTTTGATTCGCTGCTGCTGCTGTGGGTNWSNGG | 18 |
| Leaddeg3 | TTTTGATTCCCAGGTGTTCATGCTGCTGYTNYTNTGGGT | 19 |

Mixed bases: S = G+C, Y = C+T, W = A+T, N = A+T+G+C.

Figure 3

| 127 Brookhaven Structure Files Used for Surface Predictions ||||||||| |
|---|---|---|---|---|---|---|---|---|---|
| 2rcs | 3hfl | 3hfm | 1aif | 1a3r | 1bbj | 43c9 | 4fab | 6fab | 7fab |
| 2gfb | 2h1p | 2hfl | 1a6t | 1axt | 1bog | 2hrp | 2jel | 2mcp | 2pcp |
| 1yuh | 2bfv | 2cgr | 8fab | 1ae6 | 1bvl | 2dbl | 2f19 | 2fb4 | 2fbj |
| 1sm3 | 1tet | 1vfa | glb2 | 1a4j | 1cly | 1vge | 1yec | 1yed | 1yee |
| 1nsn | 1opg | 1osp | 1aj7 | 1ay1 | 1clz | 1plg | 1psk | 1rmf | 1sbs |
| 1ncd | 1nfd | 1ngp | 1acy | 1afv | 1cbv | 1nld | 1nma | 1nmb | 1nqb |
| 1mcp | 1mfb | 1mim | 15c8 | 1a5f | 1axs | 1mLb | 1mpa | 1nbv | 1ncb |
| 1jrh | 1kb5 | 1kel | 1ap2 | 1b2w | 1adq | 1kip | 1kir | 1lve | 1mam |
| 1igi | 1igm | 1igt | 1ad0 | 1baf | 1cfv | 1igy | 1ikf | 1jel | 1jhl |
| 1gpo | 1hil | 1hyx | 1a0q | 1bjm | 1clo | 1iai | 1ibg | 1igc | 1igf |
| 1fpt | 1frg | 1fvc | 1aqk | 1bln | 1d5b | 1gaf | 1ggi | 1ghf | 1gig |
| 1fai | 1fbi | 1fdl | 1ad9 | 1bbd | 1f58 | 1fgv | 1fig | 1flr | 1for |
|  | 1dbl | 1dfb | 1a3l | 1bfo | 1eap | 1dsf | 1dvf |  |  |

Figure 4

| Primer | Sequence | SEQ ID NO: |
|---|---|---|
| My96LCBsrG1 | TACAGGTGTACACTCCGATATTGTGATCACCCAGACTCC | 20 |
| My96LCOL1 | ACTGGAAATCAAACGAACTGTGGCTGCACCATCTG | 21 |
| My96LCOL2 | GCCACAGTTCGTTTGATTTCCAGTTTGGTGCCTCC | 22 |
| My96HCBsrG1 | TACAGGTGTACACTCCCAGGTTAAGCTGCAGCAGTCTGG | 23 |
| My96HCOL1 | CCACGGTCACCGTCTCCTCAGCCTCCACC | 24 |
| My96HCOL2 | GAGGCTGAGGAGACGGTGACCGTGGTCCC | 25 |
| My9-6LCNMLS | CAGGTGTACACTCCAATATTGCTCACCCAGAGTCCATCATC | 26 |
| My9-6HCQP | CAGGTGTACACTCCCAGGTTCAGCTGCAGCAGCCTGGGGCTG | 27 |
| MY96HCQ64-1 | AGAAGTTCCAAGGCAAGGCCAC | 28 |
| MY96HCQ64-2 | CTTGCCTTGGAACTTCTGATTG | 29 |
| MY96HCQ105 | CGATGGGCCCTTGGTGGAGGCTGAGGAGACGGTGACCGTGGTCCCTTGGCCCCAGACATC | 30 |
| MY96LCEVGPR | AGGTGTACACTCCGAGATTGTGCTCACCCAGAGTCTCACCCTCTGGCTGTGTCTCCAGGAGAAAGGGTCACTATGAGC | 31 |
| MY96LCR45 | GCCTGGTACCAACAGATACCAGGGCAGTCTCCTAGACTTCTGATCTAC | 32 |
| MY96LCP80-1 | AGCAGTGTTCAACCTGAAGACCTGGC | 33 |
| MY96LCP80-2 | GTCTTCAGGTTGAACACTGCTGATGG | 34 |
| MY96LCQ100 | TTTTAAGCTTCGTTTGATTTCCAGTTTGGTGCCTTGACCGAACGTCCG | 35 |
| My96lcNM | CAGGTGTACACTCCAATATTATGCTCACCCAGAG | 36 |
| MY96LCK45 | GCCTGGTACCAACAGATACCAGGGCAGTCTCCTAAACTTCTGATCTAC | 37 |
| My96HCApa1 | CGATGGGCCCTTGGTGGAGGCTGAGGAGACGGTGACCG | 38 |
| huMy96LCOL1 | ACTGGAAATCAAACGTACGGTGGCTGCACCATCTG | 39 |
| huMy96LCOL2 | GCCACCGTACGTTTGATTTCCAGTTTGGTGCCTTG | 40 |
| My96lcEM | CAGGTGTACACTCCGAGATTATGCTCACCCAGAG | 41 |
| My96lcNV | CAGGTGTACACTCCAATATTGTGCTCACCCAGAG | 42 |
| chMy96lcBsiW1 | TTTTCGTACGTTTGATTTCCAGTTTGGTGCC | 43 |

Figure 6A muMy9-6 Light Chain Amino Terminal Peptide Sequence

| | Kabat# | | | | | 5 | | | | | 10 | | | | | 15 | | | | | 20 | | | 23 | SEQ ID NO: |
|---|---|---|---|---|---|---|---|---|---|---|---|---|---|---|---|---|---|---|---|---|---|---|---|---|---|
| Edman Sequence | | N | I | M | L | T | Q | S | P | S | S | L | A | V | S | A | G | E | K | V | T | M | (S) | X | 44 |
| Deg cDNA | | D | I | V | I | T | Q | T | P | S | S | L | A | V | S | A | G | E | K | V | T | M | S | C | 45 |
| Sac1MK Primer | E L GG GAG CTC | D GAY | I ATT | V GTG | X MTS | T ACM | Q CAR | X WCT | X MCA | | | | | | | | | | | | | | | | 46 |
| Signal Pep Deg cDNA | | N | I | M | L | T | Q | S | P | S | S | L | A | V | S | A | G | E | K | V | T | M | S | C | 47 |

Figure 6B

MS-MS Sequence Analysis of muMy9-6 Light Chain CDR Peptide Fragments

| | | | | | | | | | | | | | | | SEQ ID NO: |
|---|---|---|---|---|---|---|---|---|---|---|---|---|---|---|---|
| CDR1 | K | S | S | Q | S | V | F | F | S | S | Q | K | N | Y | L | A | 48 |
| 1319 Da | | S | S | Q | S | V | F | F | S | S | Q | K | | | | | 49 |
| CDR2 | K | L | L | I | Y | W | A | S | T | R | E | S | | | | | 50 |
| 1122 Da | K | L | L | I | Y | W | A | S | T | R | E | | | | | | 51 |

Figure 7

| | muMy9-6 Heavy Chain Internal/CDR3 Peptide Sequence | SEQ ID NO: |
|---|---|---|
| 1788 Da Sequence | (R) Y F D V W G A G T T V T V S S A K (T) | 52 |
| cDNA clone 2 (match) | E V R L R Y F D V W G A G T T V T V S S<br>        CDR3 | 53 |
| cDNA clone 1 (no match) | M G E D A — M D Y W G Q G T S V T V S S<br>        CDR3 | 54 |

Figure 8A

Light Chain (sequential numbering) (SEQ ID NO:55):

```
  1 aacattatgctgacacagtcgccatcatctctggctgtgtctgca
  1  N  I  M  L  T  Q  S  P  S  S  L  A  V  S  A
```

```
 46 ggagaaaaggtcactatgagctgtaagtccagtcaaagtgttttt
 16  G  E  K  V  T  M  S  C  K  S  S  Q  S  V  F
                                 ‾‾‾‾‾‾‾‾‾‾‾‾‾‾‾
                                       CDR1
```

```
 91 ttcagttcaagtcagaagaactacttggcctggtaccaacagata
 31  F  S  S  S  Q  K  N  Y  L  A  W  Y  Q  Q  I
     ‾‾‾‾‾‾‾‾‾‾‾‾‾‾‾‾‾‾‾‾‾‾‾‾‾‾‾
              CDR1
```

```
136 ccagggcagtctcctaaacttctgatctactgggcatccactagg
 46  P  G  Q  S  P  K  L  L  I  Y  W  A  S  T  R
                                    ‾‾‾‾‾‾‾‾‾‾‾‾
                                        CDR2
```

```
181 gaatctggtgtccctgatcgcttcacaggcagtggatctgggaca
 61  E  S  G  V  P  D  R  F  T  G  S  G  S  G  T
     ‾‾‾‾‾
```

```
226 gatttactcttaccatcagcagtgtacaatctgaagacctggca
 76  D  F  T  L  T  I  S  S  V  Q  S  E  D  L  A
```

```
271 atttattactgtcatcaatacctctcctcgcggacgttcggtgga
 91  I  Y  Y  C  H  Q  Y  L  S  S  R  T  F  G  G
                 ‾‾‾‾‾‾‾‾‾‾‾‾‾‾‾‾‾‾‾‾‾‾‾
                           CDR3
```

```
316 ggcaccaaactggaaatcaaacga
106  G  T  K  L  E  I  K  R
```

Figure 8B

Heavy Chain (sequential numbering) (SEQ ID NO:56):

```
1   caggtgcaactgcagcagcctggggctgaggtggtgaagcctggg
1    Q  V  Q  L  Q  Q  P  G  A  E  V  V  K  P  G 46  gcctcagtgaagatgtcctgcaaggcttctggctacacatttacc
16   A  S  V  K  M  S  C  K  A  S  G  Y  T  F  T 91  agttactatatacactggataaagcagacacctggacagggcctg
31   S  Y  Y  I  H  W  I  K  Q  T  P  G  Q  G  L
        CDR1

136 gaatggttggagttatttatccaggaaatgatgatatttcctac
46   E  W  V  G  V  I  Y  P  G  N  D  D  I  S  Y
                    CDR2

181 aatcagaagttcaaaggcaaggccacattgactgcagacaaatcc
61   N  Q  K  F  K  G  K  A  T  L  T  A  D  K  S
        CDR2

226 tccaccacagcctacatgcaactcagcagcctgacatctgaggac
76   S  T  T  A  Y  M  Q  L  S  S  L  T  S  E  D 271 tctgcggtctattactgtgcaagagaggttcgtctacggtacttc
91   S  A  V  Y  Y  C  A  R  E  V  R  L  R  Y  F
                        CDR3

316 gatgtctggggcgcagggaccacggtcaccgtctcctca
106  D  V  W  G  A  G  T  T  V  T  V  S  S
```

Figure 9

Murine My9-6 CDRs

Light Chain | SEQ ID NO:

CDR1: K S S Q S V F F S S S Q K N Y L A | 4

CDR2: W A S T R E S | 5

CDR3: H Q Y L S S R T | 6

Heavy Chain

CDR1: S Y Y I H | 1

CDR2: V I Y P G N D D I S Y N Q K F K G | 57

CDR3: E V R L R Y F D V | 3

AbM Heavy Chain

CDR1: G Y T F T S Y Y I H | 58

CDR2: V I Y P G N D D I S | 59

CDR3: E V R L R Y F D V | 3

Figure 10

GermLine Sequence Comparisons

```
Light Chain                                                              50
8-27*     NIMMTQSPSSLAVSAGEKVTMSCKSSQSVLYSSNQKNYLAWYQQKPGQSP
muMy9-6   ...L........................FF...S............I.....

99
8-27      KLLIYWASTRESGVPDRFTGSGSGTDFTLTISSVQAEDLAVYYCHQYLS
muMy9-6   ..............................S.:...I........

Heavy Chain                                                              50
V102#     -VQLQQPGAELVKPGASVKVSCKASGYTFTSYWMHWVKQRPGQGLEWIGR
muMy9-6   Q.........V........M.............YI..I..T.......V.V 98
V102      IHPSDSDTNYNQKFKGKATLTVDKSSSTAYMQLSSLTSEDSAVYYCA-
muMy9-6   .Y.GND.IS............A....T....................R
```

\* SEQ ID NO:60
\# SEQ ID NO:61

Sequential residue numbering

Figure 11A

Light Chain Ten Most Homologous Sequences with Structures

```
              1                                                    50
My96    NIMLTQSPSS LAVSAGEKVT MSCKSSQSVF FSSSQKNYLA WYQQIPGQSP
1sbs    DIVMSQSPSS LAVSVGEKVT MTCKSSQSLL YSSNQMNYLA WYQQKPGQSP
1hil    DIVMTQSPSS LTVTAGEKVT MSCTSSQSLF NSGKQKNYLT WYQQKPGQPP
1a5f    DIVMTQSPSS LTVTTGEKVT MTCKSSQSLL NSGAQKNYLT WYQQKPGQSP
1a3r    DIVMTQSPSS LTVTTGEKVT MTCKSSQSLL NSRTQKNYLT WYQQKPGQSP
1frg    DIVMTQSPSS LTVTAGEKVT MSCKSSQSLF NSGKRKNFLT WYHQKPGQPP
1mcp    DIVMTQSPSS LSVSAGERVT MSCKSSQSLL NSGNQKNFLA WYQQKPGQPP
43c9    DVVMTQTPSS LAMSVGQKVT MSCKSSQSLL NISNQKNYLA WYQQKPGQSP
1lve    DIVMTQSPDS LAVSLGERAT INCKSSQSVL YSSNSKNYLA WYQQKPGQPP
1ap2    DIVMTQSPSS LTVTAGEKVT MSCKSSQSLL NSGNQKNYLT WYQQKPGQPP
1ncb    DIVMTQSPKF MSTSVGDRVT ITCKASQDVS T......AVV WYQQKPGQSP 100
My96    KLLIYWASTR ESGVPDRFTG SGSGTDFTLT ISSVQSEDLA IYYCHQYLSS
1sbs    KLLIYWASTR ESGVPDRFTG SGSGTDFTLT ISSVEAEDLA VYYCQQYHSY
1hil    KVLIYWASTR ESGVPDRFTG SGSGTDFTLT ISSVQAEDLA VYYCQNDYSN
1a5f    KLLIYWASTR ESGVPDRFTG SGSGTDFTLS ISGVQAEDLA VYYCQNNYNY
1a3r    KLLIYWASTR ESGVPDRFTG SGSGTDFTLS ISGVQAEDLA VYYCQNNYNY
1frg    KLLIYWASTR ESGVPDRFSG SGSGTDFTLT ITSVQAEDLA IYYCQNDYSH
1mcp    KLLIYGASTR ESGVPDRFTG SGSGTDFTLT ISSVQAEDLA VYYCQNDHSY
43c9    KLLVYFASTR ESGVPDRFIG SGSGTDFTLT ISSVQAEDQA DYFCQQHYRA
1lve    KLLIYWASTR ESGVPDRFSG SGSGTDFTLT ISSLQAEDVA VYYCQQYYST
1ap2    KLLIYWASTR ESGVPDRFTG SGSGTDFTLT ISSVQAEDLA VYYCQNDYSY
1ncb    KLLIYWASTR HIGVPDRFAG SGSGTDYTLT ISSVQAEDLA LYYCQQHYSP 115
My96    .RTFGGGTKL EIKRA    (SEQ ID NO:62)
1sbs    PFTFGSGTKL EIKRA    (SEQ ID NO:63)
1hil    PLTFGGGTKL ELKRA    (SEQ ID NO:64)
1a5f    PLTFGAGTKL ELKRA    (SEQ ID NO:65)
1a3r    PLTFGAGTKL ELKRA    (SEQ ID NO:66)
1frg    PLTFGAGTKL ELKRA    (SEQ ID NO:67)
1mcp    PLTFGAGTKL EIKRA.   (SEQ ID NO:68)
43c9    PRTFGGGTKL EIK      (SEQ ID NO:69)
1lve    PYSFGQGTKL EIKR     (SEQ ID NO:70)
1ap2    PLTFGAGTKL EPG      (SEQ ID NO:71)
1ncb    PWTFGGGTKL EIKRA    (SEQ ID NO:72)
```

Residue numbering is sequential

Figure 11B

Heavy Chain Ten Most Homologous Sequences with Structures

```
           1                                                  50
My96   QVQLQQPGAE VVKPGASVKM SCKASGYTFT SYYIHWIKQT PGQGLEWVGV
1plg   QIQLQQSGPE LVRPGASVKI SCKASGYTFT DYYIHWVKQR PGEGLEWIGW
1ae6   QIQLQQSGPE LVKPGASVKI SCKASGYTFT DYYINWMKQK PGQGLEWIGW
1for   QGQLQQSGAE LVRPGSSVKI SCKASGYAFS SFWVNWVKQR PGQGLEWIGQ
1igy   .VKLQESGAE LARPGASVKM SCKASGYTFT TYTIHWIKQR PGQGLEWIGY
1bbj   XVQLQQSDAE LVKPGASVKI SCKASGYTFT DHAIHWAKQK PEQGLEWIGY
1nqb   .VQLQQSGAE LVKPGASVKL SCKASGYTFT SYWMHWVKQR PGRGLEWIGR
1mim   ..QLQQSGTV LARPGASVKM SCKASGYSFT RYWMHWIKQR PGQGLEWIGA
1a6t   EVQLQQSGPD LVKPGASVKI SCKASGYSFS TYYMHWVKQS HGKSLEWIGR
1d5b   QVQLQQSGAE LMKPGASVKI SCKATGYTFS SFWIEWVKQR PGHGLEWIGE
1fai   QVQLQQSGAE LVRAGSSVKM SCKASGYTFT SYGVNWVKQR PGQGLEWIGY 100
My96   IYPGNDDISY NQKFKGKATL TADKSSTTAY MQLSSLTSED SAVYYCAREV
1plg   IYPGSGNTKY NEKFKGKATL TVDTSSSTAY MQLSSLTSED SAVYFCARGG
1ae6   IDPGSGNTKY NEKFKGKATL TVDTSSSTAY MQLSSLTSED TAVYFCAREK
1for   IYPGDGDNKY NGKFKGKATL TADKSSTTAY MQLYSLTSED SAVYFCARSG
1igy   INPSSVYTNY NQRFKDKATL TRDRSSNTAN IHLSSLTSDD SAVYYCVREG
1bbj   ISPGNDDIKY NEKFKGKATL TADKSSSTAY MQLNSLTSED SAVYFCKRSY
1nqb   IDPNSGGTKY NEKFKSKATL TVDKPSSTAY MQLSSLTSED SAVYYCARYD
1mim   IYPGNSDTSY NQKFEGKAKL TAVTSASTAY MELSSLTHED SAVYYCSRDY
1a6t   VDPDNGGTSF NQKFKGKAIL TVDKSSSTAY MELGSLTSED SAVYYCARRD
1d5b   ILPGSGGTHY NEKFKGKATF TADKSSNTAY MQLSSLTSED SAVYYCARGH
1fai   INPGKGYLSY NEKFKGKTTL TVDRSSSTAY MQLRSLTSED AAVYFCARSF 124
My96   RLRY...... FDVWGAGTTV TVSS    (SEQ ID NO:73)
1plg   K........FA MDYWGQGTSV TVSS   (SEQ ID NO:74)
1ae6   TTYY....YA MDYWGQGTSV TVSS    (SEQ ID NO:75)
1for   NYPY.....A MDYWGQGTSV TVSS    (SEQ ID NO:76)
1igy   .........E VPYWGQGTTV TVSS    (SEQ ID NO:77)
1bbj   YGHW...... ....GQGTTL TVSS    (SEQ ID NO:78)
1nqb   YYGS....SY FDYWGQGTTV TVSS    (SEQ ID NO:79)
1mim   GYYF...... .DFWGQGTTL TVSS    (SEQ ID NO:80)
1a6t   DY.......Y FDFWGQGTSL TVSS    (SEQ ID NO:81)
1d5b   SYYFY....D GDYWGQGTSV TVSS    (SEQ ID NO:82)
1fai   YGGSDLAVYY FDSWGQGTTL TVSS    (SEQ ID NO:83)
```

Residue numbering is sequential

Figure 13A

| muMy9-6 Light Chain Surface Residues ||||||
|---|---|---|---|---|---|---|
| Kabat Position # | Average accessibility | > 30% Ave acc | 25%-35% Ave acc | Identical flank | | muMy9-6 surface |
| 1 | 51.46 | 1 | | | | N1 |
| 3 | 35.42 | 3 | | | | M3 |
| 5 | 31.82 | 5 | 5 | NA | | T5 |
| 7 | 28.04 | | 7 | 26.17 | | |
| 9 | 40.08 | 9 | | | | S9 |
| 10 | 29.04 | | 10 | 27.76 | | |
| 12 | 29.63 | | 12 | 22.32 | other A's | |
| 15 | 34.39 | 15 | 15 | 18.20 | 33.36 | A15 |
| 16 | 25.61 | | 16 | NA | | |
| 17 | 26.21 | | 17 | 25.11 | | |
| 18 | 44.83 | 18 | | | | K18 |
| 20 | 28.91 | | 20 | 29.11 | | |
| 40 | 45.25 | 40 | | | | P40 |
| 41 | 44.52 | 41 | | | | G41 |
| 42 | 35.34 | 42 | | | | Q42 |
| 45 | 32.68 | 45 | 45 | 32.58 | | K45 |
| 57 | 39.81 | 57 | | | | G57 |
| 60 | 46.07 | 60 | | | | D60 |
| 63 | 25.60 | | 63 | 26.87 | | |
| 65 | 25.28 | | 65 | 24.07 | | |
| 67 | 32.05 | 67 | 67 | | 1Ive left out | S67 |
| 70 | 29.16 | | 70 | 29.28 | 30.13 | D70 |
| 76 | 26.02 | | 76 | 24.29 | | |
| 79 | 26.83 | | 79 | NA | | |
| 80 | 32.78 | 80 | 80 | NA | | S80 |
| 81 | 39.95 | 81 | | | | E81 |
| 100 | 33.79 | 100 | 100 | 34.05 | | G100 |
| 103 | 30.30 | 103 | 103 | 30.30 | | K103 |
| 105 | 26.42 | | 105 | 26.96 | | |
| 107 | 41.06 | 107 | | | | K107 |
| 108 | 49.29 | 108 | | | | R108 |
| 109 | 41.85 | 109 | | | | A109 |

Figure 13B

| muMy9-6 Heavy Chain Surface Residues ||||||
|---|---|---|---|---|---|
| Kabat Position # | Average accessibility | > 30% Ave accessibility | 25%-35% Ave acc | Identical flank | muMy9-6 surface |
| 1 | 40.08 | 1 | | | Q1 |
| 3 | 38.62 | 3 | | | Q3 |
| 5 | 28.06 | | 5 | NA | |
| 9 | 35.98 | 9 | | | A9 |
| 11 | 48.07 | 11 | | | V11 |
| 13 | 49.75 | 13 | | | K13 |
| 14 | 32.39 | 14 | 14 | 32.20 | P14 |
| 15 | 30.69 | 15 | 15 | 31.84 | G15 |
| 17 | 26.01 | | 17 | 26.67 | |
| 19 | 37.64 | 19 | | | K19 |
| 23 | 29.92 | | 23 | 30.11 | K23 |
| 26 | 29.48 | | 26 | 31.43 | G26 |
| 28 | 33.67 | 28 | 28 | 35.59 | T28 |
| 41 | 44.46 | 41 | | | P41 |
| 42 | 46.28 | 42 | | | G42 |
| 43 | 42.00 | 43 | | | Q43 |
| 52B | 25.21 | | 52B | 25.21 | |
| 53 | 28.84 | | 53 | 28.84 | |
| 56 | 29.08 | | 56 | 29.08 | |
| 61 | 43.12 | 61 | | | Q61 |
| 62 | 44.46 | 62 | | | K62 |
| 64 | 38.56 | 64 | | | K64 |
| 65 | 41.85 | 65 | | | G65 |
| 68 | 28.38 | | 68 | 28.30 | |
| 70 | 25.14 | | 70 | 28.21 | |
| 73 | 32.97 | 73 | 73 | 35.71 | K73 |
| 74 | 47.68 | 74 | | | S74 |
| 75 | 26.67 | | 75 | 27.22 | |
| 82B | 32.62 | 82B | 82B | 30.58 | S82B |
| 83 | 26.03 | | 83 | 26.52 | |
| 84 | 35.34 | 84 | | | S84 |
| 85 | 37.78 | 85 | | | E85 |
| 105 | 36.29 | 105 | | | A105 |
| 108 | 25.74 | | 108 | 28.73 | |
| 110 | 26.94 | | 110 | 23.38 | |
| 112 | 41.61 | 112 | | | S112 |

Figure 14 muMy9-6 Surface Residues within 5 Å of a CDR Residue

| Light chain | Heavy chain |
|---|---|
| N1 | Q1 |
| M3 | T28 |
| T5 | K64 |
| K45 | K73 |
| G57 | |
| D60 | |
| S67 | |
| D70 | |

Figure 15

Top Five Most Homologous Human Antibody Surfaces

| Antibody | Light Chain | SEQ ID NO: | Heavy Chain | SEQ ID NO: |
|---|---|---|---|---|
| muMy9-6 | N M T S A K P G Q Q K G D S E G K K R A | 84 | Q Q A V K P G K G T P G Q Q K K G K S S S E A S | 90 |
| 21H9 | D Q T S V R P G E K G S S D P E G K K K R T | 85 | Q Q A V K P G K G T P G Q Q K Q G T P S S S E K S | 91 |
| EL-14 | D V T S V R P G K K G S S D P E G K K K R – | 86 | Q Q A A A K P G K G T P G Q Q K Q G G S S S E Q S | 92 |
| CLL-412 | D Q T S V R P G K K G S S D P E Q K K K R T | 87 | Q Q A V K P G K G T P G Q Q K Q G T S S S S E Q S | 93 |
| LC3bPB | E V T G P R P G Q R G D S D P E Q K K K R – | 88 | – Q A V K P G K G T P G Q Q K Q G K S S S S E Q S | 94 |
| CLL1.69 | D V T L L P P G Q R G D A D A E Q K K K R – | 89 | Q Q A V K P G K G T P G Q Q K Q G K S S S S E Q S | 95 |

Figure 16A

Humanized My9-6 Light Chain Versions

```
Kabat #              10         20         27b        34         44
muMy9-6        NIMLTQSPSS LAVSAGEKVT MSCKSSQSVF FSSSQKNYLA WYQQIPGQSP
huMy9-6 V1.0   EIVLTQSPGS LAVSPGERVT MSCKSSQSVF FSSSQKNYLA WYQQIPGQSP
huMy9-6 V1.1   N.M....... .......... .......... .......... ..........
huMy9-6 V1.2   N.M....... .......... .......... .......... ..........
huMy9-6 V1.3   E.V....... .......... .......... .......... ..........
huMy9-6 V1.4   N.M....... .......... .......... .......... ..........
huMy9-6 V1.5   N.M....... .......... .......... .......... ..........
huMy9-6 V1.6   E.V....... .......... .......... .......... ..........
huMy9-6 V1.7   E.V....... .......... .......... .......... ..........
huMy9-6 V1.8   E.M....... .......... .......... .......... ..........
huMy9-6 V1.9   E.M....... .......... .......... .......... ..........
huMy9-6 V1.10  E.M....... .......... .......... .......... ..........
huMy9-6 V1.11  E.M....... .......... .......... .......... ..........
huMy9-6 V1.12  N.V....... .......... .......... .......... ..........
huMy9-6 V1.13  N.V....... .......... .......... .......... ..........
huMy9-6 V1.14  N.V....... .......... .......... .......... ..........
huMy9-6 V1.15  N.V....... .......... .......... .......... ..........

Kabat #              54         64         74         84         94
muMy9-6        KLLIYWASTR ESGVPDRFTG SGSGTDFTLT ISSVQSEDLA IYYCHQYLSS
huMy9-6 V1.0   RLLIYWASTR ESGVPDRFTG SGSGTDFTLT ISSVQPEDLA IYYCHQYLSS
huMy9-6 V1.1   K......... .......... .......... .......... ..........
huMy9-6 V1.2   K......... .......... .......... .......... ..........
huMy9-6 V1.3   R......... .......... .......... .......... ..........
huMy9-6 V1.4   R......... .......... .......... .......... ..........
huMy9-6 V1.5   R......... .......... .......... .......... ..........
huMy9-6 V1.6   K......... .......... .......... .......... ..........
huMy9-6 V1.7   K......... .......... .......... .......... ..........
huMy9-6 V1.8   R......... .......... .......... .......... ..........
huMy9-6 V1.9   R......... .......... .......... .......... ..........
huMy9-6 V1.10  K......... .......... .......... .......... ..........
huMy9-6 V1.11  K......... .......... .......... .......... ..........
huMy9-6 V1.12  R......... .......... .......... .......... ..........
huMy9-6 V1.13  R......... .......... .......... .......... ..........
huMy9-6 V1.14  K......... .......... .......... .......... ..........
huMy9-6 V1.15  K......... .......... .......... .......... ..........

Kabat #                   108
muMy9-6        RTFGGGTKLE IKR         (SEQ ID NO:8)
huMy9-6 V1.0   RTFGQGTKLE IKR         (SEQ ID NO:10)
huMy9-6 V1.1   .......... ...
huMy9-6 V1.2   .......... ...
huMy9-6 V1.3   .......... ...
huMy9-6 V1.4   .......... ...
huMy9-6 V1.5   .......... ...
huMy9-6 V1.6   .......... ...
huMy9-6 V1.7   .......... ...
huMy9-6 V1.8   .......... ...
huMy9-6 V1.9   .......... ...
huMy9-6 V1.10  .......... ...
huMy9-6 V1.11  .......... ...
huMy9-6 V1.12  .......... ...
huMy9-6 V1.13  .......... ...
huMy9-6 V1.14  .......... ...
huMy9-6 V1.15  .......... ...
```

Figure 16B

Humanized My9-6 Heavy Chain Versions

```
Kabat #              10         20         30         40         50
muMy9-6         QVQLQQPGAE VVKPGASVKM SCKASGYTFT SYYIHWIKQT PGQGLEWVGV
huMy9-6 V1.0    QVQLQQPGAE VVKPGASVKM SCKASGYTFT SYYIHWIKQT PGQGLEWVGV
huMy9-6 V1.1    .......... .......... .......... .......... ..........
huMy9-6 V1.2    .......... .......... .......... .......... ..........
huMy9-6 V1.3    .......... .......... .......... .......... ..........
huMy9-6 V1.4    .......... .......... .......... .......... ..........
huMy9-6 V1.5    .......... .......... .......... .......... ..........
huMy9-6 V1.6    .......... .......... .......... .......... ..........
huMy9-6 V1.7    .......... .......... .......... .......... ..........
huMy9-6 V1.8    .......... .......... .......... .......... ..........
huMy9-6 V1.9    .......... .......... .......... .......... ..........
huMy9-6 V1.10   .......... .......... .......... .......... ..........
huMy9-6 V1.11   .......... .......... .......... .......... ..........
huMy9-6 V1.12   .......... .......... .......... .......... ..........
huMy9-6 V1.13   .......... .......... .......... .......... ..........
huMy9-6 V1.14   .......... .......... .......... .......... ..........
huMy9-6 V1.15   .......... .......... .......... .......... ..........

Kabat #              59         69         79         86         96
muMy9-6         IYPGNDDISY NQKFKGKATL TADKSSTTAY MQLSSLTSED SAVYYCAREV
huMy9-6 V1.0    IYPGNDDISY NQKFQGKATL TADKSSTTAY MQLSSLTSED SAVYYCAREV
huMy9-6 V1.1    .......... ....K..... .......... .......... ..........
huMy9-6 V1.2    .......... ....Q..... .......... .......... ..........
huMy9-6 V1.3    .......... ....K..... .......... .......... ..........
huMy9-6 V1.4    .......... ....Q..... .......... .......... ..........
huMy9-6 V1.5    .......... ....K..... .......... .......... ..........
huMy9-6 V1.6    .......... ....Q..... .......... .......... ..........
huMy9-6 V1.7    .......... ....K..... .......... .......... ..........
huMy9-6 V1.8    .......... ....Q..... .......... .......... ..........
huMy9-6 V1.9    .......... ....K..... .......... .......... ..........
huMy9-6 V1.10   .......... ....Q..... .......... .......... ..........
huMy9-6 V1.11   .......... ....K..... .......... .......... ..........
huMy9-6 V1.12   .......... ....Q..... .......... .......... ..........
huMy9-6 V1.13   .......... ....K..... .......... .......... ..........
huMy9-6 V1.14   .......... ....Q..... .......... .......... ..........
huMy9-6 V1.15   .......... ....K..... .......... .......... ..........

Kabat #             105        112
muMy9-6         RLRYFDVWGA GTTVTVSS      (SEQ ID NO:7)
huMy9-6 V1.0    RLRYFDVWGQ GTTVTVSS      (SEQ ID NO:9)
huMy9-6 V1.1    .......... ........
huMy9-6 V1.2    .......... ........
huMy9-6 V1.3    .......... ........
huMy9-6 V1.4    .......... ........
huMy9-6 V1.5    .......... ........
huMy9-6 V1.6    .......... ........
huMy9-6 V1.7    .......... ........
huMy9-6 V1.8    .......... ........
huMy9-6 V1.9    .......... ........
huMy9-6 V1.10   .......... ........
huMy9-6 V1.11   .......... ........
huMy9-6 V1.12   .......... ........
huMy9-6 V1.13   .......... ........
huMy9-6 V1.14   .......... ........
huMy9-6 V1.15   .......... ........
```

Figure 17

| | Direct on Membranes | Competitive on Membranes | Direct on Cells |
|---|---|---|---|
| | pM | pM | nM |
| murine | 51.34+/-8.74 | 173.64+/-39.29 | 1.10+/-0.13 |
| V1.0 | 66.53+/-17.83 | 209.00+/-52.37 | 1.02+/-0.04 |
| V1.1 | 83.57+/-13.82 | 279.50+/-152.03* | 1.07+/-0.11* |
| V1.3 | 63.95+/-0.64* | 203.05+/-153.83* | 1.16+/-0.39* |
| V1.6 | 56.10+/-15.13* | 216.50+/-70.00* | 0.97+/-0.08* |

My9-6 $K_D$ Values

Figure 18
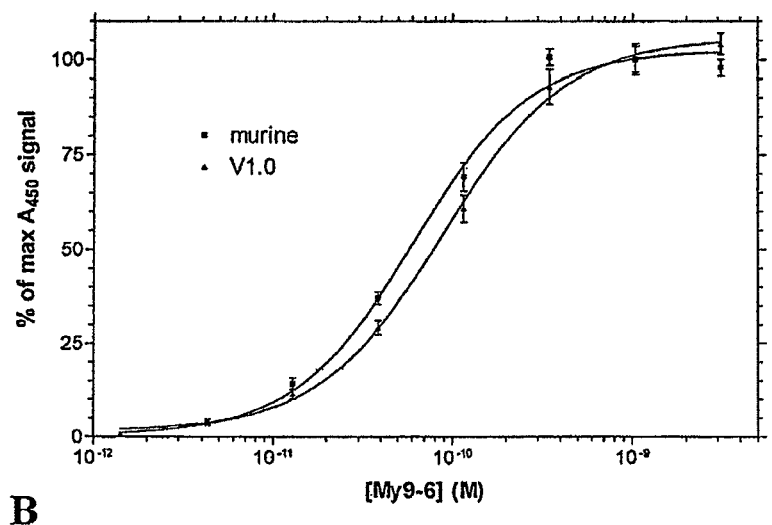
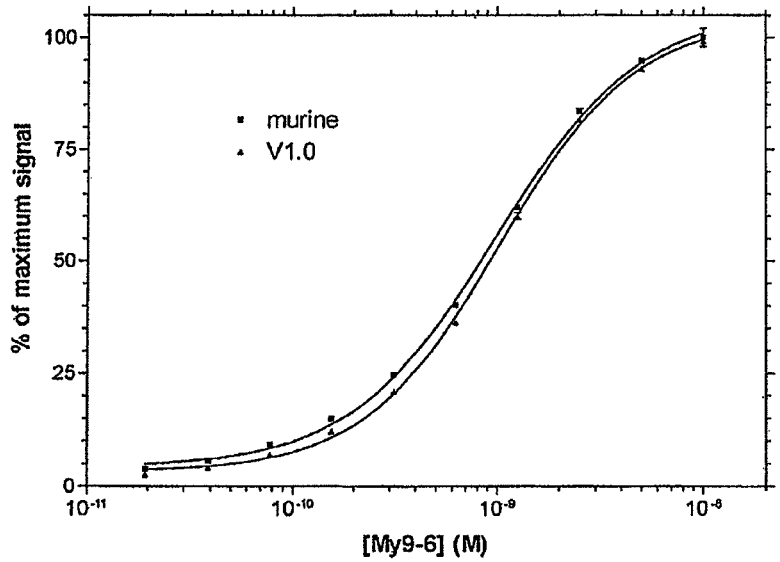

Figure 22
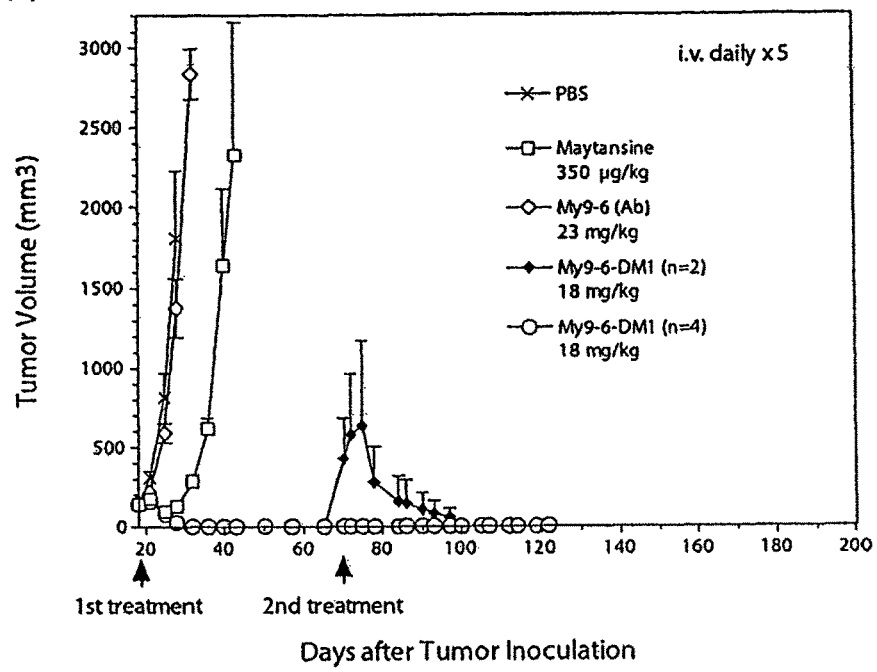
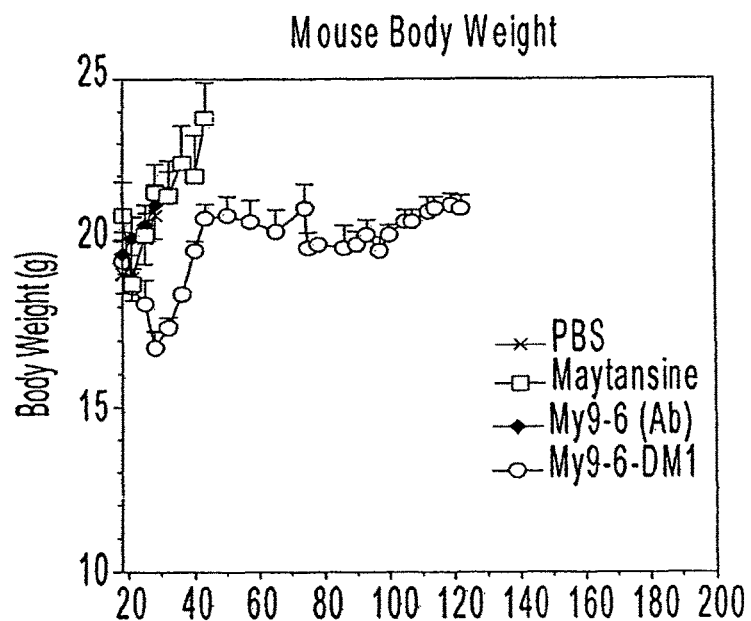

Efficacy of My9-6-DM1 in Survival model

Comparison of My9-6-DM1 to Gemtuzumab Ozogamicin and standard chemotherapy

ANTI-CD33 ANTIBODIES AND METHODS FOR TREATMENT OF ACUTE MYELOID LEUKEMIA USING THE SAME

CROSS-REFERENCE TO RELATED APPLICATIONS

This application is a Continuation of U.S. application Ser. No. 14/249,602, filed Apr. 10, 2014; which is a Divisional of U.S. application Ser. No. 13/680,614, filed Nov. 19, 2012 now U.S. Pat. No. 8,747,851; which is a Divisional of U.S. application Ser. No. 13/019,478, filed Feb. 2, 2011 now U.S. Pat. No. 8,337,855; which is a Continuation of U.S. application Ser. No. 12/358,832, filed Jan. 23, 2009, now abandoned; which is a Continuation of U.S. application Ser. No. 10/700,632, filed Nov. 5, 2003, now U.S. Pat. No. 7,557,189; which claims the benefit of U.S. Provisional Application No. 60/424,332, filed Nov. 7, 2002, the disclosure of each of which is incorporated herein by reference in their entirety.

FIELD OF THE INVENTION

The present invention relates to antibodies that bind CD33. More particularly, the invention relates to anti-CD33 antibodies, fragments and homologues of said antibodies, humanized and resurfaced versions of said antibodies, functional equivalents and improved versions of said antibodies, immunoconjugates and compositions comprising said antibodies, and the uses of same in diagnostic, research and therapeutic applications.

In another aspect, the invention relates to a polynucleotide encoding the antibodies, vectors comprising the polynucleotides, host cells transformed with polynucleotides and methods of producing the antibodies.

BACKGROUND OF THE INVENTION

The leukocyte differentiation antigen CD33 is a 364 amino acid transmembrane glycoprotein with sequence homology to members of the sialoadhesin family, including myelin-associated glycoprotein and CD22, as well as sialoadhesin itself (S. Peiper, 2002, Leucocyte Typing VII, White Cell Differentiation, Antigens, Proceedings of the Seventh International Workshop and Conference, Oxford University Press, p. 777).

Expression of CD33 appears to be highly specific to the hematopoietic compartment, with strong expression by myeloid precursor cells (S. Peiper, 2002). It is expressed by myeloid progenitor cells such as CFU-GEMM, CFU-GM, CFU-G and BFU-E, monocytes/macrophages, granulocyte precursors such as promyelocytes and myelocytes although with decreased expression upon maturation and differentiation, and mature granulocytes though with a low level of expression (S. Peiper, 2002).

In contrast, pluripotent hematopoietic stem cells that give rise to "blast colonies" in vitro (Leary, A. G. et al., 1987, Blood 69:953) and that induce hematopoietic long-term marrow cultures (Andrews R. G. et al., 1989, J. Exp. Med. 169:1721; Sutherland, H. J. et a., 1989, Blood 74:1563) appear to lack expression of CD33.

While the specific function of CD33 is unknown, its homology to sialoadhesin suggested a role in carbohydrate binding characteristic of the lectin family, a role later confirmed (S. Peiper, 2002).

Importantly, anti-CD33 monoclonal antibodies have shown that CD33 is expressed by clonogenic, acute myelogenous leukemia (AML) cells in greater than 80% of human cases (LaRussa, V. F. et al., 1992, Exp. Hematol. 20:442-448).

Due to the selective expression of CD33, immunoconjugates that combine cytotoxic drugs with monoclonal antibodies that specifically recognize and bind CD33 have been proposed for use in selective targeting of AML cells. Such therapies are expected to leave stem cells and primitive hematopoietic progenitors unaffected. Immunoconjugates that utilize anti-CD33 antibodies include anti-CD33-ricin immunoconjugates that have been shown to be highly lethal to AML cells (Roy, D. C. et al., 1991, Blood 77:2404; Lambert, J. M. et al., 1991, Biochemistry 30:3234), yet spare the stem cells that support normal hematopoiesis and hematopoietic reconstitution (LaRussa, V. F. et al., 1992, Exp. Hematol. 20:442-448).

Additional studies using immunoconjugates have shown rapid targeting of radiolabeled anti-CD33 antibodies to leukemic blast cells in peripheral blood and marrow when administered i.v. (Scheinberg, D. A. et al., 1991, J. Clin. Oncol. 9: 478-490; Schwartz, M. A. et al., 1993, J. Clin. Oncol. 11:294-303). Rapid internalization of the antibody by the target cell was also observed in in vitro studies (Tanimot, M. et al., 1989, Leukemia 3: 339-348; Divgi, C. R. et al., 1989, Cancer Res. Suppl. Vol. 30: 404a). Evaluation of a humanized anti-CD33 antibody conjugated to the potent antitumor antibiotic calicheamicin (Gemtuzumab ozogamicin) in pre-clinical studies demonstrated specific killing of leukemia cells in HL-60 cell cultures, HL-60 tumor xenografts in mice, and marrow samples from AML patients (Hamann, P. R. et al., 2002, Bioconjugate Chem. 13: 47-58).

Based on the positive results of these pre-clinical studies, Gemtuzumab ozogamicin was evaluated in phase I and II clinical studies. In Phase I studies, the major toxicity observed was myelosuppression due to the expression of CD33 on myeloid progenitor cells (Sievers, E. L. et al. 1999, Blood 93: 3678-3684; Sievers E. L. et al., 2001, J. Clin. Oncol. 19: 3244-3254.). Phase II studies with a dose of 9 mg/m$^2$ i.v. over 4 hours, repeated after 14 days, yielded a response rate of 30%. Marketing approval of Gemtuzumab ozogamicin was granted by the FDA in May 2000 with indication for the treatment of patients with CD33 positive AML in first relapse who are 60 years of age or older and who are not considered candidates for cytotoxic chemotherapy. Post-marketing reports have indicated the potential for significant toxicity, especially venoocclusive disease (VOD), which has led to labeling revisions and initiation of a patient surveillance program. Much of this toxicity may be related to the drug component calicheamicin, which was shown to cause hepatotoxicity in pre-clinical models, and therefore may not be a direct result of targeting CD33.

While the results discussed above suggest that immunoconjugates comprising an anti-CD33 antibody and a cytotoxic drug may be successfully used in the treatment of AML, there is a need for immunoconjugates that are both safe and effective. The present invention is directed to these and other important ends.

SUMMARY OF THE INVENTION

Accordingly, it is an object of the present invention to provide antibodies that specifically bind to CD33, and that may be used in the treatment of AML.

Thus, in a first embodiment, there is provided an antibody, or epitope-binding fragment thereof, having the ability to bind CD33.

In a second embodiment, there is provided the murine antibody My9-6, which is fully characterized herein with respect to the amino acid sequences of both its light and heavy chain variable regions, the cDNA sequences of the genes for the light and heavy chain variable regions, the identification of its CDRs (complementarity-determining regions), the identification of its surface amino acids, and means for its expression in recombinant form.

In a third embodiment, there are provided humanized or resurfaced versions of the My9-6 antibody wherein surface-exposed residues of the My9-6 antibody or epitope-binding fragments thereof are replaced in both light and heavy chains to more closely resemble known human antibody surfaces. Such humanized antibodies may have increased utility, compared to murine My9-6, as therapeutic or diagnostic agents. Humanized versions of antibody My9-6 are also fully characterized herein with respect to their respective amino acid sequences of both light and heavy chain variable regions, the DNA sequences of the genes for the light and heavy chain variable regions, the identification of the CDRs, the identification of their surface amino acids, and disclosure of a means for their expression in recombinant form.

In a further embodiment, there are provided antibodies or epitope-binding fragments thereof comprising at least one complementarity-determining region having an amino acid sequence selected from the group consisting of SEQ ID NOs:1-6:

SYYIH, (SEQ ID NO: 1)

VIYPGNDDISYNQKFXG, (SEQ ID NO: 2)
wherein X is K or Q,

EVRLRYFDV, (SEQ ID NO: 3)

KSSQSVFFSSSQKNYLA, (SEQ ID NO: 4)

WASTRES, (SEQ ID NO: 5)

HQYLSSRT, (SEQ ID NO: 6)

and having the ability to bind CD33.

In a further embodiment, there are provided antibodies or epitope-binding fragments thereof comprising at least one heavy chain variable region and at least one light chain variable region, wherein said heavy chain variable region comprises three complementarity-determining regions having amino acid sequences represented by SEQ ID NOs:1-3, respectively,

SYYIH, (SEQ ID NO: 1)

VIYPGNDDISYNQKFXG, (SEQ ID NO: 2)
wherein X is K or Q,

EVRLRYFDV, (SEQ ID NO: 3)

and wherein said light chain variable region comprises three complementarity-determining regions having amino acid sequences represented by SEQ ID NOs:4-6, respectively.

KSSQSVFFSSSQKNYLA, (SEQ ID NO: 4)

WASTRES, (SEQ ID NO: 5)

HQYLSSRT. (SEQ ID NO: 6)

In a further embodiment, there are provided antibodies having a heavy chain variable region that has an amino acid sequence that shares at least 90% sequence identity with an amino acid sequence represented by SEQ ID NO:7:

QVQLQQPGAEVVKPGASVKMSCKASGYTFTSYYIHWIKQTPGQGLEWVG

VIYPGNDDISYNQKFKGKATLTADKSSTTAYMQLSSLTSEDSAVYYCAR

EVRLRYFDVWGAGTTVTVSS, more preferably 95% sequence identity with SEQ ID NO:7, most preferably 100% sequence identity with SEQ ID NO:7.

Similarly, there are provided antibodies having a light chain variable region that has an amino acid sequence that shares at least 90% sequence identity with an amino acid sequence represented by SEQ ID NO:8:

NIMLTQSPSSLAVSAGEKVTMSCKSSQSVFFSSSQKNYLAWYQQIPGQS

PKLLIYWASTRESGVPDRFTGSGSGTDFTLTISSVQSEDLAIYYCHQYL

SSRTFGGGTKLEIKR, more preferably 95% sequence identity with SEQ ID NO:8, most preferably 100% sequence identity with SEQ ID NO:8.

In a further embodiment, antibodies are provided having a humanized or resurfaced heavy chain variable region that shares at least 90% sequence identity with an amino acid sequence represented by SEQ ID NO:9:

QVQLQQPGAEVVKPGASVKMSCKASGYTFTSYYIHWIKQTPGQGLEWVG

VIYPGNDDISYNQKFQGKATLTADKSSTTAYMQLSSLTSEDSAVYYCAR

EVRLRYFDVWGQGTTVTVSS, more preferably 95% sequence identity with SEQ ID NO:9, most preferably 100% sequence identity with SEQ ID NO:9.

Similarly, antibodies are provided having a humanized or resurfaced light chain variable region that shares at least 90% sequence identity with an amino acid sequence corresponding to SEQ ID NO:10:

EIVLTQSPGSLAVSPGERVTMSCKSSQSVFFSSSQKNYLAWYQQIPGQS

PRLLIYWASTRESGVPDRFTGSGSGTDFTLTISSVQPEDLAIYYCHQYL

SSRTFGQGTKLEIKR, more preferably 95% sequence identity with SEQ ID NO:10, most preferably 100% sequence identity with SEQ ID NO:10.

In a further embodiment, the present invention provides immunoconjugates comprising a drug or prodrug covalently attached, directly or via a cleavable or non-cleavable linker, to an antibody or epitope-binding fragment thereof of the present invention. In preferred embodiments, the drug or prodrug is a cytotoxic drug or prodrug such as a maytansinoid, a taxoid, CC-1065, a CC-1065 analog, dolastatin and a dolastatin analog.

In a further embodiment, the present invention provides a composition comprising an antibody or epitope-binding fragment thereof of the present invention and a drug or prodrug.

In a further embodiment, the present invention comprises pharmaceutical compositions comprising an antibody, epitope-binding fragment thereof or immunoconjugate of the present invention, either alone or in combination with a drug or prodrug or other therapeutic agent, in the presence of one or more pharmaceutically acceptable agent.

In a further embodiment, the present invention provides for an antibody or epitope-binding fragment thereof that is labeled for use in research or diagnostic applications. In preferred embodiments, the label is a biotin label, an enzyme label, a radio-label, a fluorophore, a chromophore, an imaging agent or a metal ion.

In a further embodiment, the present invention provides methods for inhibiting the growth of a cell expressing CD33 through the use of an antibody, epitope-binding fragment thereof or immunoconjugate of the present invention, either alone or in combination with a drug or prodrug or other therapeutic agent, further alone or in the presence of one or more pharmaceutically acceptable agent.

In an further embodiment, the invention provides methods for the treatment of a subject having a disease wherein CD33 is expressed comprising administering an antibody, an epitope-binding fragment thereof or immunoconjugate of the present invention, either alone or in combination with another a drug or prodrug or another therapeutic agent, further alone or in the presence of one or more pharmaceutically acceptable agent. The disease may be one or more of, for example, myelodysplastic syndrome (MDS), acute myeloid leukemia (AML), chronic myeloid leukemia (CML) and pro-myelocytic leukemia (PML), or other disease yet to be determined in which CD33 is expressed.

The methods of treatment include in vivo, ex vivo and in vitro application of the antibodies, antibody fragments and immunoconjugates of the present invention, either alone or in combination with a drug or prodrug or other therapeutic agent, further alone or in the presence of one or more pharmaceutically acceptable agent.

In a further embodiment, a method of determining whether a biological sample contains a myelogenous cancer cell is provided wherein a biological sample is contacted with a diagnostic reagent, such as a labeled antibody or epitope-binding fragment thereof of the present invention, and the distribution of the reagent within the sample is detected. This method may be used to diagnose a cancer such as acute myeloid leukemia (AML), chronic myeloid leukemia (CML) and pro-myelocytic leukemia (PML).

In a further embodiment, antibodies or epitope-binding fragments thereof of the present invention are provided that have improved properties. For example, antibodies or epitope-binding fragments thereof having improved affinity for CD33 may be prepared by the standard techniques of animal immunization, hybridoma formation and selection for antibodies with specific characteristics.

Improved antibodies may also be prepared by affinity maturation of an antibody or epitope-binding fragment thereof of the present invention through, for example, oligonucleotide-mediated site-directed mutagenesis, cassette mutagenesis, error-prone PCR, DNA shuffling and use of mutator-strains of *E. coli*.

In a further embodiment, the present invention provides polynucleotides encoding the antibodies or epitope-binding fragments thereof of the present invention, recombinant vectors comprising the polynucleotides, host cells transformed with the recombinant vectors and methods for producing said antibodies and epitope-binding fragments thereof by culturing said host cells.

In a final embodiment, the present invention provides a method for obtaining CD33 from a biological material using an antibody or epitope-binding fragment thereof of the present invention.

BRIEF DESCRIPTION OF THE DRAWINGS

FIG. 2 shows the My9-6 degenerate primers for the light chain signal sequence.

FIG. 3 shows the file names of the 127 antibody structures from the Brookhaven database that were used to predict the surface of the muMy9-6 variable region.

FIG. 4 shows the PCR primers used to build the 16 resurfaced My9-6 versions as well as chimeric My9-6 antibody.

FIG. 6A shows the Edman sequencing results compared with amino acid sequence derived from the RT-PCR generated cDNA clones for muMy9-6 light chain.

FIG. 6B shows the results from the MS-MS sequence analysis of the 1319 Da and 1122 Da peptide fragments containing CDR1 and CDR2 sequences respectively. CDR sequences are in bold.

FIG. 7 shows the results from the MS-MS sequence analysis of the 1788 Da peptide and the corresponding sequence derived from two cDNA clones.

FIG. 8A shows the cDNA sequence and the deduced amino acid sequence (SEQ ID NO:95) of the light chain variable region for the murine My9-6 antibody. The three CDRs are underlined.

FIG. 8B shows the cDNA sequence and the deduced amino acid sequence (SEQ ID NO:96) of the heavy chain variable region for the murine My9-6 antibody. The three CDRs are underlined.

FIG. 9 shows the light and heavy chain CDRs as determined by the Kabat definitions.

FIG. 10 shows the light chain and heavy chain amino acid sequence for the murine My9-6 antibody aligned with the germLine sequences for the 8-27 and V102 genes. Dots (.) indicate sequence identity.

FIGS. 11A & B show the ten light chain (A) and heavy chain (B) antibody sequences most homologous to the muMy9-6 sequences that have solved files in the Brookhaven database. Sequences are aligned in order of most to least homology.

FIG. 13A shows the residue solvent accessibilities for the ten most homologous light chain structures, calculated with the MC software, and shows the averages for each Kabat position, tabulated with Excel. This table presents the data for non-CDR positions with average solvent accessibilities greater than 25%. A surface residue is defined as a residue with greater than a 30% average solvent accessibility. Positions with 25%-35% average accessibilities were further analyzed by calculating average accessibilities of structures only with identical residues at that position as well as in the two flanking positions on either side. NA refers to identical flanking positions not available. Positions 15 and 70 required further calculations to arrive at the final surface predictions given in the last column.

FIG. 13B shows the residue solvent accessibilities for the ten most homologous heavy chain structures, calculated with the MC software, and shows the averages for each Kabat position, tabulated with Excel. This table presents the data for non-CDR positions with average solvent accessibilities greater than 25%. A surface residue is defined as a residue with greater than a 30% average solvent accessibility. Positions with 25%-35% average accessibilities were further analyzed by calculating average accessibilities of structures only with identical residues at that position as well as in the two flanking positions on either side. NA refers to identical flanking positions not available.

FIG. 14 shows the My9-6 framework surface residues that fall within 5 Å of a CDR residue.

FIG. 15 shows the top five human sequences extracted from the Kabat database. Alignments were generated by SR (Pedersen, 1993). The muMy9-6 residues that come within 5 Å of a CDR are underlined.

FIGS. 16A & B show the 16 humanized My9-6 light chain variable region sequences (A) and the 16 humanized My9-6 heavy chain variable region sequences (B) aligned with murine My9-6. The dots (.) represent sequence identity with humanized version 1.0. The surface residues that differ in murine and human My9-6 are underlined.

FIG. 17 shows the My9-6 $K_D$ values calculated by direct binding assay on HL-60 membranes and HL-60 whole cells, as well as competitive binding assay on HL-60 membranes. N≥3 except for * where N=2.

FIG. 22 shows a comparison of the efficacy of My9-6-DM1 with the free drug maytansine in SCID mice bearing HL-60 xenografts (A). Mouse body weight was monitored as an indication of toxicity (B). Relapsed tumors in two treated mice were treated with a second course of My9-6-DM1.

DETAILED DESCRIPTION OF THE INVENTION

The present invention provides a novel murine anti-CD33 antibody and humanized versions of this antibody. Further provided are antibodies comprising one or more of the CDRs of the murine anti-CD33 antibody or humanized version thereof that specifically recognize and bind to CD33.

Murine My9-6 Antibody

The murine anti-CD33 antibody of the present invention, variously designated herein as "My9-6", "murine My9-6" and "muMy9-6", is fully characterized with respect to the putative germline amino acid sequence of both light and heavy chain variable regions (FIG. 10), amino acid sequences of both light and heavy chain variable regions (FIGS. 8A & B), the identification of the CDRs (FIG. 9), the identification of surface amino acids (FIGS. 13A & B), and means for its expression in recombinant form.

Figure 1:
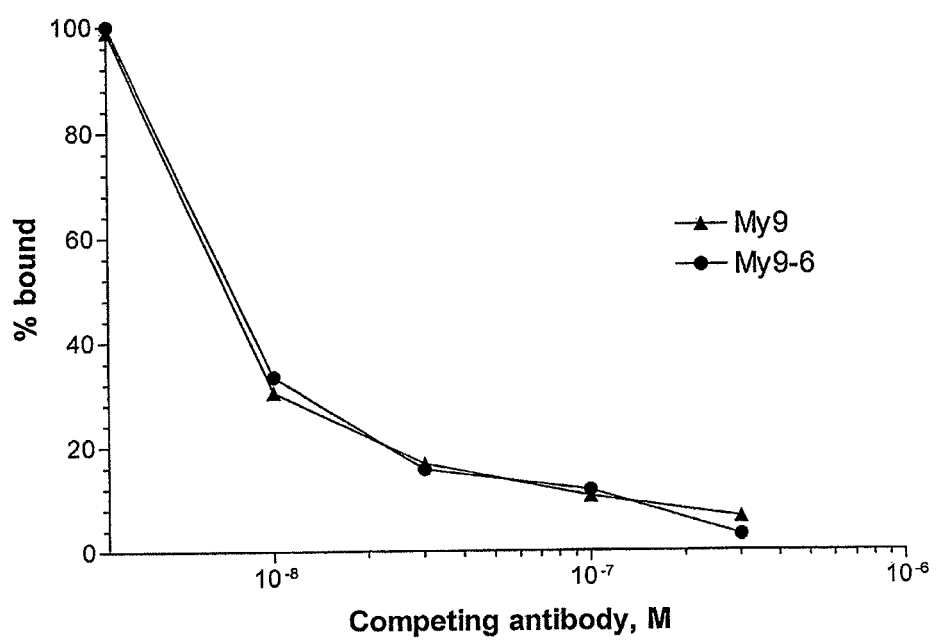
FIG. 1 shows the results of a competition binding experiment in which binding of $^{125}$I-labeled My9-6 antibody ($3\times10^{-9}$ M) to CD33-positive U-937 cells was assayed in the presence of increasing concentrations of either My9 or My9-6 antibody.

The My9-6 antibody has further been functionally characterized and shown to bind with high affinity to CD33 on the surface of CD33-positive U-937 cells (FIG. 1). $^{125}$I-labeled My9-6 binds to U-937 cells and it is competed off the cells by unlabeled My9-6 and the previously characterized anti-CD33 antibody My9 (BioGenex, cat. no. 267M).

The term "variable region" is used herein to describe certain portions of antibody heavy chains and light chains that differ in sequence among antibodies and that cooperate in the binding and specificity of each particular antibody for its antigen. Variability is not usually evenly distributed throughout antibody variable regions. It is typically concentrated within three segments of a variable region called complementarity-determining regions (CDRs) or hypervariable regions, both in the light chain and the heavy chain variable regions. The more highly conserved portions of the variable regions are called the framework regions. The variable regions of heavy and light chains comprise four framework regions, largely adopting a beta-sheet configuration, with each framework region connected by the three CDRs, which form loops connecting the beta-sheet structure, and in some cases forming part of the beta-sheet structure. The CDRs in each chain are held in close proximity by the framework regions and, with the CDRs from the other chain, contribute to the formation of the antigen binding site of antibodies (E. A. Kabat et al. Sequences of Proteins of Immunological Interest, Fifth Edition, 1991, NIH).

The "constant" region is not involved directly in binding an antibody to an antigen, but exhibits various effector functions, such as participation of the antibody in antibody-dependent cellular toxicity.

Humanized My9-6 Antibody

Humanized versions of My9-6, variously designated herein as "huMy9-6", and "humanized My9-6", have also been prepared.

The goal of humanization is a reduction in the immunogenicity of a xenogenic antibody, such as a murine antibody, for introduction into a human, while maintaining the full antigen binding affinity and specificity of the antibody.

Humanized antibodies may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host.

Strategies and methods for the resurfacing of antibodies, and other methods for reducing immunogenicity of antibodies within a different host, are disclosed in U.S. Pat. No. 5,639,641 (Pedersen et al.), which is hereby incorporated in its entirety by reference. Briefly, in a preferred method, (1) position alignments of a pool of antibody heavy and light chain variable regions is generated to give a set of heavy and light chain variable region framework surface exposed positions wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity-determining regions of the rodent antibody; and (5) the humanized rodent antibody having binding specificity is produced.

Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, *Molecular Immunology* 28(4/5):489-498; Studnicka G. M. et al., 1994, *Protein Engineering* 7(6):805-814; Roguska M. A. et al., 1994, PNAS 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

Figure 18:
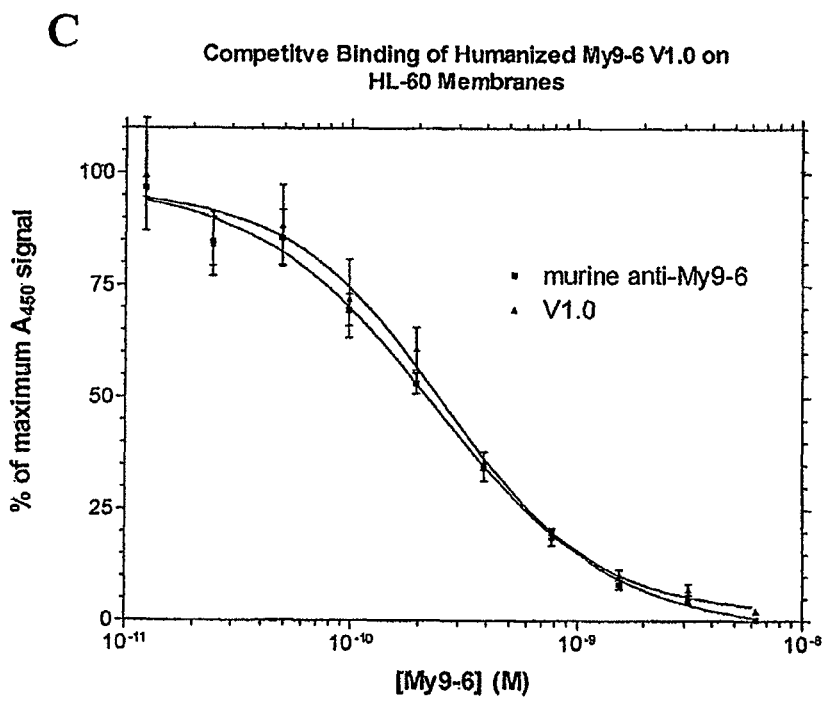
FIG. 18 shows binding curves for huMy9-6 V1.0. (A): direct binding on HL-60 membranes. (B): direct binding on HL-60 whole cells. (C): competitive binding on HL-60 membranes.

As further described herein, the CDRs of My9-6 were identified by modeling and their molecular structures were predicted. Humanized My9-6 antibodies were then prepared and have been fully characterized. The amino acid sequences of the light and heavy chains of a number of huMy9-6 antibodies are shown in FIGS. 16A and 16B. Comparative binding values for murine and humanized My9-6 antibodies are provided in FIG. 17. Binding curves for the antibodies are shown in FIG. 18.

Epitope-Binding Fragments of the My9-6 Antibodies

Although epitope-binding fragments of the murine My9-6 antibody and the humanized My9-6 antibodies are discussed herein separately from the murine My9-6 antibody and the humanized versions thereof, it is understood that the term "antibody" or "antibodies" of the present invention may include both the full length muMy9-6 and huMy9-6 antibodies as well as epitope-binding fragments of these antibodies.

As used herein, "antibody fragments" include any portion of an antibody that retains the ability to bind to CD33, generally termed "epitope-binding fragments." Examples of antibody fragments preferably include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Epitope-binding fragments, including single-chain antibodies, may comprise the variable region(s) alone or in combination with the entirety or a portion of the following: hinge region, $C_H1$, $C_H2$, and $C_H3$ domains.

Such fragments may contain one or both Fab fragments or the F(ab')$_2$ fragment. Preferably, the antibody fragments contain all six CDRs of the whole antibody, although fragments containing fewer than all of such regions, such as three, four or five CDRs, are also functional. Further, the functional equivalents may be or may combine members of any one of the following immunoglobulin classes: IgG, IgM, IgA, IgD, or IgE, and the subclasses thereof.

Fab and F(ab')$_2$ fragments may be produced by proteolytic cleavage, using enzymes such as papain (Fab fragments) or pepsin (F(ab')$_2$ fragments).

The single-chain FVs (scFvs) fragments are epitope-binding fragments that contain at least one fragment of an antibody heavy chain variable region ($V_H$) linked to at least one fragment of an antibody light chain variable region ($V_L$). The linker may be a short, flexible peptide selected to assure that the proper three-dimensional folding of the ($V_L$) and ($V_H$) regions occurs once they are linked so as to maintain the target molecule binding-specificity of the whole antibody from which the single-chain antibody fragment is derived. The carboxyl terminus of the ($V_L$) or ($V_H$) sequence may be covalently linked by a linker to the amino acid terminus of a complementary ($V_L$) and ($V_H$) sequence. Single-chain antibody fragments may be generated by molecular cloning, antibody phage display library or similar techniques well known to the skilled artisan. These proteins may be produced, for example, in eukaryotic cells or prokaryotic cells, including bacteria.

The epitope-binding fragments of the present invention can also be generated using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labeled CD33 or CD33 bound or captured to a solid surface or bead. Phage used in these methods are typically filamentous phage including fd and M13 binding domains expressed from phage with Fab, Fv or disulfide-stabilized Fv antibody domains recombinantly fused to either the phage gene III or gene VIII protein.

Examples of phage display methods that can be used to make the epitope-binding fragments of the present invention include those disclosed in Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187:9-18; Burton et al., 1994, *Advances in Immunology* 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908;

5,516,637; 5,780,225; 5,658,727; 5,733,743 and 5,969,108; each of which is incorporated herein by reference in its entirety.

After phage selection, the regions of the phage encoding the fragments can be isolated and used to generate the epitope-binding fragments through expression in a chosen host, including mammalian cells, insect cells, plant cells, yeast, and bacteria, using recombinant DNA technology, e.g., as described in detail below. For example, techniques to recombinantly produce Fab, Fab' and F(ab')$_2$ fragments can also be employed using methods known in the art such as those disclosed in PCT publication WO 92/22324; Mullinax et al., 1992, *BioTechniques* 12(6):864-869; Sawai et al., 1995, *AJRI* 34:26-34; and Better et al., 1988, Science 240:1041-1043; said references incorporated by reference in their entireties. Examples of techniques which can be used to produce single-chain Fvs and antibodies include those described in U.S. Pat. Nos. 4,946,778 and 5,258,498; Huston et al., 1991, *Methods in Enzymology* 203:46-88; Shu et al., 1993, PNAS 90:7995-7999; Skerra et al., 1988, *Science* 240:1038-1040.

Functional Equivalents

Also included within the scope of the invention are functional equivalents of the My9-6 antibody and the humanized My9-6 antibodies. The term "functional equivalents" includes antibodies with homologous sequences, chimeric antibodies, modified antibody and artificial antibodies, for example, wherein each functional equivalent is defined by its ability to bind to CD33. The skilled artisan will understand that there is an overlap in the group of molecules termed "antibody fragments" and the group termed "functional equivalents."

Antibodies with homologous sequences are those antibodies with amino acid sequences that have sequence identity or homology with amino acid sequence of the murine My9-6 and humanized My9-6 antibodies of the present invention. Preferably identity is with the amino acid sequence of the variable regions of the murine My9-6 and humanized My9-6 antibodies of the present invention. "Sequence identity" and "sequence homology" as applied to an amino acid sequence herein is defined as a sequence with at least about 90%, 91%, 92%, 93%, or 94% sequence identity, and more preferably at least about 95%, 96%, 97%, 98%, or 99% sequence identity to another amino acid sequence, as determined, for example, by the FASTA search method in accordance with Pearson and Lipman, Proc. Natl. Acad. Sci. USA 85, 2444-2448 (1988).

As used herein, a chimeric antibody is one in which different portions of an antibody are derived from different animal species. For example, an antibody having a variable region derived from a murine monoclonal antibody paired with a human immunoglobulin constant region. Methods for producing chimeric antibodies are known in the art. See, e.g., Morrison, 1985, *Science* 229:1202; Oi et al., 1986, *BioTechniques* 4:214; Gillies et al., 1989, *J. Immunol. Methods* 125:191-202; U.S. Pat. Nos. 5,807,715; 4,816,567; and 4,816,397, which are incorporated herein by reference in their entireties.

Artificial antibodies include scFv fragments, diabodies, triabodies, tetrabodies and mru (see reviews by Winter, G. and Milstein, C., 1991, Nature 349: 293-299; Hudson, P. J., 1999, Current Opinion in Immunology 11: 548-557), each of which has antigen-binding ability. In the single chain Fv fragment (scFv), the $V_H$ and $V_L$ domains of an antibody are linked by a flexible peptide. Typically, this linker peptide is about 15 amino acid residues long. If the linker is much smaller, for example 5 amino acids, diabodies are formed, which are bivalent scFv dimmers. If the linker is reduced to less than three amino acid residues, trimeric and tetrameric structures are formed that are called triabodies and tetrabodies. The smallest binding unit of an antibody is a CDR, typically the CDR2 of the heavy chain which has sufficient specific recognition and binding that it can be used separately. Such a fragment is called a molecular recognition unit or mru. Several such mrus can be linked together with short linker peptides, therefore forming an artificial binding protein with higher avidity than a single mru.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, phosphorylation, amidation, derivatization by known protecting/blocking groups, proteolytic cleavage, linkage to a cellular ligand or other protein, etc. The covalent attachment does not prevent the antibody from generating an anti-idiotypic response. These modifications may be carried out by known techniques, including, but not limited to, specific chemical cleavage, acetylation, formylation, metabolic synthesis of tunicamycin, etc. Additionally, the modified antibodies may contain one or more non-classical amino acids.

Functional equivalents may be produced by interchanging different CDRs on different chains within different frameworks. Thus, for example, different classes of antibody are possible for a given set of CDRs by substitution of different heavy chains, whereby, for example, IgG$_{1-4}$, IgM, IgA$_{1-2}$, IgD, IgE antibody types and isotypes may be produced. Similarly, artificial antibodies within the scope of the invention may be produced by embedding a given set of CDRs within an entirely synthetic framework.

Functional equivalents may be readily produced by mutation, deletion and/or insertion within the variable and/or constant region sequences that flank a particular set of CDRs, using a wide variety of methods known in the art.

The antibody fragments and functional equivalents of the present invention encompass those molecules with a detectable degree of binding to CD33, when compared to the murine My9-6 antibody. A detectable degree of binding includes all values in the range of at least 10-100%, preferably at least 50%, 60% or 70%, more preferably at least 75%, 80%, 85%, 90%, 95% or 99% the binding ability of the murine My9-6 antibody to CD33.

Improved Antibodies

The CDRs are of primary importance for epitope recognition and antibody binding. However, changes may be made to the residues that comprise the CDRs without interfering with the ability of the antibody to recognize and bind its cognate epitope. For example, changes that do not affect epitope recognition, yet increase the binding affinity of the antibody for the epitope may be made.

Thus, also included in the scope of the present invention are improved versions of both the murine and humanized antibodies, which also specifically recognize and bind CD33, preferably with increased affinity.

Several studies have surveyed the effects of introducing one or more amino acid changes at various positions in the sequence of an antibody, based on the knowledge of the primary antibody sequence and on its properties such as binding and level of expression (Yang, W. P. et al., 1995, *J. Mol. Biol.*, 254, 392-403; Rader, C. et al., 1998, *Proc. Natl. Acad. Sci. USA,* 95, 8910-8915; Vaughan, T. J. et al., 1998, *Nature Biotechnology,* 16, 535-539).

In these studies, equivalents of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of E. coli (Vaughan, T. J. et al., 1998, Nature Biotechnology, 16, 535-539; Adey, N. B. et al., 1996, Chapter 16, pp. 277-291, in "Phage Display of Peptides and Proteins", Eds. Kay, B. K. et al., Academic Press). These methods of changing the sequence of the primary antibody have resulted in improved affinities of the secondary antibodies (Gram, H. et al., 1992, Proc. Natl. Acad. Sci. USA, 89, 3576-3580; Boder, E. T. et al., 2000, Proc. Natl. Acad. Sci. USA, 97, 10701-10705; Davies, J. and Riechmann, L., 1996, Immunotechnolgy, 2, 169-179; Thompson, J. et al., 1996, J. Mol. Biol., 256, 77-88; Short, M. K. et al., 2002, J. Biol. Chem., 277, 16365-16370; Furukawa, K. et al., 2001, J. Biol. Chem., 276, 27622-27628).

By a similar directed strategy of changing one or more amino acid residues of the antibody, the antibody sequences described herein can be used to develop anti-CD33 antibodies with improved functions, including improved affinity for CD33.

Improved antibodies also include those antibodies having improved characteristics that are prepared by the standard techniques of animal immunization, hybridoma formation and selection for antibodies with specific characteristics Immunoconjugates The present invention is also directed to immunoconjugates, comprising the antibodies, antibody fragments, functional equivalents, improved antibodies and their analogs as disclosed herein, linked to a drug or prodrug. Preferred drugs or prodrugs are cytotoxic agents and include, for example, maytansinoids and maytansinoid analogs, taxoids, CC-1065 and CC-1065 analogs, dolastatin and dolastatin analogs.

The immunoconjugates may be prepared by in vitro methods. In order to link a drug or prodrug to the antibody, a linking group is used. Suitable linking groups are well known in the art and include disulfide groups, thioether groups, acid labile groups, photolabile groups, peptidase labile groups and esterase labile groups. Preferred linking groups are disulfide groups and thioether groups. For example, conjugates can be constructed using a disulfide exchange reaction or by forming a thioether bond between the antibody and the drug or prodrug.

Maytansinoids and maytansinoid analogs are among the preferred cytotoxic agents. Examples of suitable maytansinoids include maytansinol and maytansinol analogs. Suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

With respect to maytansinoids, the linking group may comprise a reactive chemical group. In a preferred embodiment, the reactive chemical group can be covalently bound to the maytansinoid via a disulfide bond linking moiety.

Particularly preferred reactive chemical groups are N-succinimidyl esters and N-sulfosuccinimidyl esters.

Particularly preferred maytansinoids comprising a linking group that contains a reactive chemical group are C-3 esters of maytansinol and its analogs where the linking moiety contains a disulfide bond and the chemical reactive group comprises a N-succinimidyl or N-sulfosuccinimidyl ester.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

Other chemical bonds include acid labile bonds, photolabile bonds, peptidase labile bonds and esterase labile bonds. The disclosure of U.S. Pat. No. 5,208,020, incorporated herein, teaches the production of maytansinoids bearing such bonds.

As described in detail below, the immunocojugate My9-6-DM1 utilizes thiol-containing maytansinoid (DM1). DM1 is represented by the following structural formula (1):

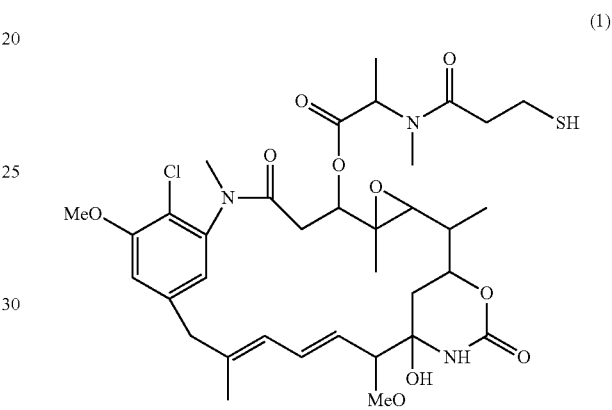

(1)

Taxanes are also preferred cytotoxic agents. Taxanes suitable for use in the present invention are disclosed in U.S. Pat. Nos. 6,372,738 and 6,340,701. Conjugates of the taxanes of the invention and a cell binding agent can be formed using any techniques presently known or later developed. Numerous methods of conjugation are taught in U.S. Pat. No. 5,416,064 and U.S. Pat. No. 5,475,092.

CC-1065 and its analogs are also preferred cytotoxic drugs for use in the present invention. CC-1065 and its analogs are disclosed in U.S. Pat. Nos. 6,372,738; 6,340,701; 5,846,545; and 5,585,499. CC-1065 is a potent antitumor antibiotic isolated from the culture broth of Streptomyces zelensis. CC-1065 is about 1000-fold more potent in vitro than commonly used anti-cancer drugs, such as doxorubicin, methotrexate and vincristine (B. K. Bhuyan et al., Cancer Res., 42, 3532-3537 (1982)).

Drugs such as methotrexate, daunorubicin, doxorubicin, vincristine, vinblastine, melphalan, mitomycin C, chlorambucil, calicheamicin, dolastatin and dolastatin analogs are also suitable for the preparation of conjugates of the present invention. The drug molecules can also be linked to the antibody molecules through an intermediary carrier molecule such as serum albumin.

Inhibiting the Growth of CD33-Expressing Cells

Also included in the present invention are methods for inhibiting the growth of cells expressing CD33. These methods make use of the antibodies or immunoconjugates of the present invention, as well as the antibodies or immunoconjugates of the present invention in conjunction with one or more additional therapeutic agents. Suitable therapeutic agents include those that inhibit the growth of a cell expressing CD33 directly or indirectly.

As used herein the terms "inhibit" and "inhibiting" should be understood to include any inhibitory effect on cell growth, including cell death. The inhibitory effects include temporary effects, sustained effects and permanent effects.

Therapeutic Applications

The present invention also includes therapeutic applications of the antibodies or immunoconjugates of the present invention wherein the antibodies or immunoconjugates may be administered to a subject, in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. They may also be administered by intratumoral, peritumoral, intralesional, or perilesional routes, to exert local as well as systemic therapeutic effects.

A pharmaceutically acceptable dosage form will generally include a pharmaceutically acceptable agent such as a carrier, diluent, and excipient. These agents are well known and the most appropriate agent can be determined by those of skill in the art as the clinical situation warrants. Examples of suitable carriers, diluents and/or excipients include: (1) Dulbecco's phosphate buffered saline, pH ~7.4, containing about 1 mg/ml to 25 mg/ml human serum albumin, (2) 0.9% saline (0.9% w/v NaCl), and (3) 5% (w/v) dextrose.

In other therapeutic applications, the antibodies or immunoconjugates of the invention are co-administered with one or more additional therapeutic agents. Therapeutic agents are those agents that seek to kill or limit the growth of cancer cells while doing minimal damage to the host. Thus, such agents may exploit any difference in cancer cell properties (e.g. metabolism, vascularization or cell-surface antigen presentation) from healthy host cells. Differences in tumor morphology are potential sites for intervention. For example, the therapeutic agent can be an antibody such as an anti-VEGF antibody that is useful in retarding the vascularization of the interior of a solid tumor, thereby slowing its growth rate.

Suitable therapeutic agents include, but are not limited to, cytotoxic or cytostatic agents. Taxol is a preferred therapeutic agent that is also a cytotoxic agent. Other therapeutic agents include, but are not limited to, adjuncts such as granisetron HCL, androgen inhibitors such as leuprolide acetate, antibiotics such as doxorubicin, antiestrogens such as tamoxifen, antimetabolites such as interferon alpha-2a, enzyme inhibitors such as ras farnesyl-transferase inhibitor, immunomodulators such as aldesleukin, and nitrogen mustard derivatives such as melphalan HCl, and the like.

When present in an aqueous dosage form, rather than being lyophilized, the antibody typically will be formulated at a concentration of about 0.1 mg/ml to 100 mg/ml, although wide variation outside of these ranges is permitted. For the treatment of disease, the appropriate dosage of antibody or conjugate will depend on the type of disease to be treated, as defined above, the severity and course of the disease, whether the antibodies are administered for preventive or therapeutic purposes, the course of previous therapy, the patient's clinical history and response to the antibody, and the discretion of the attending physician. The antibody is suitably administered to the patient at one time or over a series of treatments.

Depending on the type and severity of the disease, about 0.015 to 15 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs. However, other dosage regimens may be useful and are not excluded.

The therapeutic applications of the present invention include methods of treating a subject having a disease. The diseases treated with the methods of the present invention are those characterized by the expression of CD33. Such diseases include myelodysplastic syndromes (MDS) and cancers such as acute myeloid leukemia (AML), chronic myeloid leukemia (CML) and pro-myelocytic leukemia (PML). The skilled artisan will understand that the methods of the present invention may also be used to treat other diseases yet to be described but characterized by the expression of CD33.

The therapeutic applications of the present invention can be also practiced in vitro and ex vivo.

Examples of in vitro uses include the purification of cell populations contaminated with CD33-positive cells such as cells of myeloid lineage. The method comprises culturing the cell populations in the presence of a cytotoxic My9-6 immunoconjugate and then removal of dead, CD33-positive cells. The conditions for non-clinical in vitro use are well known (see, e.g., Uckun et al., 1986, *J Exp. Med.* 163, 347-368; Uckun et al., 1985, *J. Immunol.* 134, 3504-3515; Ramakrishnan et al., 1985, *J. Immunol.* 3616-3622).

Examples of clinical ex vivo use include treatment of autologous bone marrow prior to their infusion into the same patient in order to kill diseased or malignant myeloid lineage cells (Roy D. C. et al., 1995, *J. Clin. Immunol.* 15, 51-57).

Diagnostic and Research Applications

In addition to the therapeutic uses of the antibodies discussed herein, the antibodies of the present invention can be employed in many known diagnostic and research applications. Antibodies of the present invention may be used, for example, in the purification, detection, and targeting of CD33, included in both in vitro and in vivo diagnostic methods. For example, the antibodies may be used in immunoassays for qualitatively and quantitatively measuring levels of CD33 expressed by cells in biological samples. See, e.g., Harlow et al., Antibodies: A Laboratory Manual (Cold Spring Harbor Laboratory Press, 2nd ed. 1988), incorporated by reference herein in its entirety.

The antibodies of the present invention may be used in, for example, competitive binding assays, direct and indirect sandwich assays, and immunoprecipitation assays (Zola, Monoclonal Antibodies: A Manual of Techniques, pp. 147-158 (CRC Press, Inc., 1987)).

The antibodies of the invention also are useful for in vivo imaging, wherein an antibody labeled with a detectable moiety such as a radio-opaque agent or radioisotope is administered to a subject, preferably into the bloodstream, and the presence and location of the labeled antibody in the host is assayed. This imaging technique is useful in the staging and treatment of malignancies. The antibody may be labeled with any moiety that is detectable in a host, whether by nuclear magnetic resonance, radiology, or other detection means known in the art.

The label can be any detectable moiety that is capable of producing, either directly or indirectly, a detectable signal. For example, the label may be a biotin label, an enzyme label (e.g., luciferase, alkaline phosphatase, beta-galactosidase and horseradish peroxidase), a radio-label (e.g., $^3$H, $^{14}$C, $^{32}$P, $^{35}$S, and $^{125}$I), a fluorophore such as fluorescent or chemiluminescent compound (e.g., fluorescein isothiocyanate, rhodamine), an imaging agent (e.g., Tc-m99 and indium ($^{111}$In)) and a metal ion (e.g., gallium and europium).

Any method known in the art for conjugating the antibody to the label may be employed, including those methods described by Hunter, et al., 1962, Nature 144:945; David et al., 1974, Biochemistry 13:1014; Pain et al., 1981, J. Immunol. Meth. 40:219; Nygren, J., 1982, Histochem. and Cytochem. 30:407.

The antibodies of the invention also are useful as affinity purification agents. In this process, the antibodies are immobilized on a suitable support, such a Sephadex resin or filter paper, using methods well known in the art. Thus, CD33 may be isolated and purified from a biological sample.

Polynucleotides, Vectors, Host Cells and Methods for Making Antibody

The present invention further provides polynucleotides comprising a nucleotide sequence encoding an antibody of the invention or epitope-binding fragments thereof.

The present invention also encompasses polynucleotides encoding a polypeptide that can bind CD33 and that hybridize under stringent hybridization conditions to polynucleotides that encode an antibody of the present invention, wherein said stringent hybridization conditions include: pre-hybridization for 2 hours at 60° C. in 6×SSC, 0.5% SDS, 5×Denhardt's solution, and 100 µg/ml heat denatured salmon sperm DNA; hybridization for 18 hours at 60° C.; washing twice in 4×SSC, 0.5% SDS, 0.1% sodium pyrophosphate, for 30 min at 60° C. and twice in 2×SSC, 0.1% SDS for 30 min at 60° C.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., 1994, BioTechniques 17:242) which, briefly, involves the synthesis of overlapping oligonucleotides containing portions of the sequence encoding the antibody, annealing and ligation of those oligonucleotides, and then amplification of the ligated oligonucleotides by PCR.

Methods for the construction of recombinant vectors containing antibody coding sequences and appropriate transcriptional and translational control signals are well known in the art. These methods include, for example, in vitro recombinant DNA techniques, synthetic techniques, and in vivo genetic recombination. The invention, thus, provides replicable vectors comprising a nucleotide sequence encoding an antibody molecule of the present invention, or a heavy or light chain thereof, or a heavy or light chain variable domain, or an epitope-binding fragment of any of these, operably linked to a promoter.

The recombinant vector is transferred to a host cell by conventional techniques and the transfected cells are then cultured by conventional techniques to produce an antibody of the invention. Thus, the invention includes host cells containing a polynucleotide encoding an antibody of the invention, or an epitope-binding fragment thereof, operably linked to a heterologous promoter. In preferred embodiments, vectors encoding both the heavy and light chains may be co-expressed in the host cell for expression of an entire immunoglobulin molecule.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Preferably, bacterial cells such as Escherichia coli, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; Cockett et al., 1990, Bio/Technology 8:2).

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.) and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

EXAMPLES

The invention is now described by reference to the following examples, which are illustrative only, and are not intended to limit the present invention.

Example 1. Murine My9-6 Antibody

In this first example, the complete primary amino acid structure and cDNA sequence of the murine My9-6 antibody of the present invention is disclosed, together with its binding properties and means for its expression in recombinant form. Accordingly, there is provided a full and complete disclosure of an antibody of the invention and its preparation, such that one of ordinary skill in the immunological arts would be able to prepare said antibody without undue experimentation.

1.1. Generation, Production and Characterization of My9-6 Antibody

A 3T3 murine fibroblast cell line transfected with the CD33 antigen was used for immunization.

BALB/c female mice, 5 months old, were immunized intraperitoneally on day 0 with the transfected 3T3 murine fibroblast cell line ($2.5\times10^6$ cells, suspended in 0.2 mL PBS). The animals were boosted with 0.2 mL cell suspension as follows: day 13, $5\times10^6$ cells; day 21, $5\times10^6$ cells. On day 24, a mouse was sacrificed and its spleen removed.

The spleen was ground between two frosted glass slides to obtain a single cell suspension, which was washed with serum-free RPMI medium containing penicillin and streptomycin (SFM). The spleen cell pellet was resuspended in 10 mL of 0.83% (w/v) ammonium chloride solution in water for 10 min on ice to lyse the red blood cells, and was then washed with serum-free medium (SFM). Spleen cells ($1.6\times10^8$) were pooled with myeloma cells ($5.4\times10^7$) from the non-secreting mouse myeloma cell line P3X63Ag8.653 (ATCC, Rockville, Md.; cat. no. CRL 1580) in a tube, and washed with the serum-free RPMI-1640 medium (SFM). The supernatant was removed and the cell pellet diluted to $2\times10^7$ cells/mL. The cells were plated at $2\times10^7$ cells/plate onto tissue culture plates that were coated with 15 mg/mL concanavalin A. Plates were incubated for one hour at 37° C. The supernatant was gently removed from the plates. One mL of polyethylene glycol solution (40% PEG w/v) was slowly added dropwise. The plates were swirled and incubated for 30 seconds. The PEG was removed and discarded. The plates were washed twice by slowly adding 5 mL of SFM and then discarding. After the final wash, 5 mL of SFM supplemented with 5% Fetal Bovine Serum (FBS) was added. Plates were incubated overnight at 37° C. Following incubation, cells were scraped off the plates with a cell scraper and pooled. The plates were rinsed and pooled with the cells. Cells were pelleted by centrifugation and resuspended in RPMI-1640 growth media supplemented with 5% FBS, penicillin-streptomycin and hypoxanthine/aminopterin/thymidine (HAT). Cells were plated at $2\times10^5$ cells/well on 96-well flat bottom tissue culture plates containing a macrophage feeder layer. The general conditions used for immunization and hybridoma production were as described by J. Langone and H. Vunakis (Eds., Methods in Enzymology, Vol. 121, "Immunochemical Techniques, Part I"; 1986; Academic Press, Florida) and E. Harlow and D. Lane ("Antibodies: A Laboratory Manual"; 1988; Cold Spring Harbor Laboratory Press, New York). Other techniques of immunization and hybridoma production can also be used, as are well known to those of skill in the art.

Culture supernatants from hybridoma clones were screened for binding to cells transfected with the CD33 antigen and the human histiocytic lymphoma cell line, U-937 (ATCC CRL-1953.2) and for a lack of binding to a mouse fibroblast cell line. These clones were expanded and subcloned. The culture supernatants of the subclones were further screened by the above binding assays. By this procedure, subclone 3E7-H2-3D8 (My9-6) was selected, and the heavy and light chain genes were cloned and sequenced as described below.

Screening of hybridoma supernatants for specific binding to the CD33 antigen was performed using ELISA on cell lines that expressed this antigen and on a cell line negative for this antigen. Cells were separately harvested from tissue culture flasks, suspended in growth medium containing 10% FBS, pelleted by centrifugation, and washed with PBS. The washed cells (100 µL of about $1-3\times10^6$ cells/mL) were added to wells of an Immulon-2HB plate coated with phytohemagglutinin (100 µL of 20 µg/mL PHA), centrifuged and allowed to adhere to PHA-coated wells for 10 min. The plate with cells was flicked to remove PBS and was then dried overnight at 37° C. The wells were blocked with 5 mg/mL BSA solution in PBS for 1 h at 37° C. and were then washed gently with PBS. Aliquots of the supernatants from hybridoma clones (100 µL; diluted in blocking buffer) were then added to wells containing CD33 antigen-expressing cells and to cells not expressing CD33, and were incubated at ambient temperature for 1 h. The wells were washed with PBS, incubated with goat-anti-mouse-IgG-antibody-horseradish peroxidase conjugate (100 µL; in blocking buffer) for 1 h, followed by washes and then binding was detected using an $ABTS/H_2O_2$ substrate. A typical supernatant from a 3E7 hybridoma subclone upon incubation with cells overexpressing CD33 antigen yielded a signal of 0.50 absorbance units, in contrast to a value of 0.10 absorbance units obtained upon incubation with cells negative for the CD33 antigen.

The hybridoma was grown in ascites in BALB/c mice. A vial of frozen hybridoma cells was thawed and the cells were expanded in tissue culture flasks to obtain the necessary number of cells for ascites production. Primed BALB/c mice (mice had been injected i.p. with 0.5 mL of pristane 10-14 days in advance) were injected i.p. with $1\times10^6$ cells in 0.5 mL of phosphate buffered saline (PBS). Twelve to 18 days after injection of the cells, ascites fluid was withdrawn from the peritoneal cavity of the mice with a syringe. The pooled ascites fluid was centrifuged at 1000 rpm for 5 min, the supernatant was then subjected to centrifugation at 12,000 rpm for 30 minutes. The antibody was purified from the clear supernatant as follows: Step 1: ammonium sulfate precipitation. The supernatant on ice was diluted with two volumes of cold PBS, stirred and then treated slowly with one volume of cold, saturated (100%) ammonium sulfate solution. The solution was left standing on ice for about 5 hours, when the precipitate was collected by centrifugation. The pellet was dissolved in a small amount of PBS and the resulting solution was dialyzed into the buffer for the affinity purification step with protein A. Step 2: Affinity purification on Sepharose-Protein A. The isotype of murine My9-6 is IgG1 with a kappa light chain. Therefore the affinity column was equilibrated in 0.1 M tris.HCl buffer containing 3 M NaCl, pH 8.0. The antibody solution in the same buffer was passed through the column, the column was washed well with the equilibrating buffer and then eluted with 0.1 M acetic acid containing 0.15 M NaCl. Fractions were assayed by measuring the UV absorption at 280 nm. Fractions containing the antibody were combined, neutralized with 1 M tris and then dialyzed into PBS for use and storage.

Purified antibody was initially characterized for binding to CD33-expressing cells, such as the transfected murine 3T3 fibroblast cell line and the human U-937 cell line, and the absence of binding to antigen-negative cell lines as described above for the screening of hybridoma supernatants.

To further ascertain its specificity for binding to the CD33 antigen, a competition binding experiment was performed between labeled muMy9-6 and the commercially available anti-CD33 antibody My9. The binding experiment was performed using the method described by Goldmacher et al. (1989, *J. Cell. Physiol.* 141, 222-234). Murine My9-6 antibody was radiolabeled with $^{125}$I using the Iodo-gen technique (Fraker, P. J. and Speck, J. C., 1978, *Biochem. Biophys. Res. Commun.* 80, 849-857). A constant amount ($3\times10^{-9}$ M) of $^{125}$I-labeled muMy9-6 was mixed with increasing concentrations of non-radioactive antibody, either unlabeled muMy9-6 or unlabelled My9, and the mixtures were incubated with cells ($1\times10^6$ cells per sample) at 4° C. for 30 min. These incubations were done in 60 µl of a buffer consisting of Minimum Essential Medium Modified for Suspension Cultures (SMEM) supplemented with 2.5% human serum. The cells were then separated from the media containing non-bound material by centrifugation through a mixture of silicone oil (Aldrich) and paraffin oil (Baker) with a density of 1.009 g/ml. The cell pellet was then removed by cutting the centrifuge tubes at the oil interface and was used to measure the cell-associated radioactivity on a gamma-counter (model RIAgamma 1274 from LKB). The cell-associated radioactivity measured was blotted against the concentrations of the unlabelled, competing antibodies. The results are shown in FIG. 1: both antibodies, My9 and My9-6, give very similar competition binding curves. This demonstrates that My9 and My9-6 bind to the same antigen and furthermore that both antibodies have very similar binding avidities. Since My9 is a published and accepted anti-CD33 standard it was concluded that My9-6 is an anti-CD33 antibody. My9 antibody is commercially available from BioGenex (San Ramon, Calif. 94583; cat. no. AM267-5M).

1.2. Cloning of Heavy and Light Chain Genes of My9-6 Antibody

Total RNA was purified from a confluent T175 flask of My9-6 hybridoma cells as described in Molecular Protocols (NB1455-p173). RNA integrity was checked on a 1% MOPS gel and concentrations were determined by UV spectrophotometry. RT reactions were done with 4-5 µg total RNA using the Gibco Superscript II kit and either oligo dT or random hexamer primers.

PCR reactions were done both by using a RACE method described in Co et al. (1992, *J. Immunol.* 148(4):1149-54) and by using degenerate primers described in Wang et al. (2000, *J. Immunol. Methods.* 233:167-177). The RACE PCR required an intermediate step to add a poly dG tail on the 3' ends of the first strand cDNAs. RT reactions were purified with Qianeasy (Qiagen) columns and eluted in 50 µl×NEB buffer 4. A dG tailing reaction was done on the eluate with 0.25 mM CoCl$_2$, 1 mM dGTP, and 5 units terminal transferase (NEB), in 1×NEB buffer 4. The mixture was incubated at 37° C. for 30 minutes and then ⅕ of the reaction mixture (10 µl) was added directly to a PCR reaction mixture to serve as the template DNA.

The RACE and degenerate PCR reactions were identical except for differences in primers and template. As mentioned above, the terminal transferase reaction mixture was used directly for the RACE PCR template, while the RT reaction mix was used directly for degenerate PCR reactions. In both reaction sets the same 3' light chain primer, HindKL:

(SEQ ID NO: 11)
TATAGAGCTCAAGCTTGGATGGTGGGAAGATGGATACAGTTGGTGC and 3' heavy chain primer, Bgl2IgG1:

(SEQ ID NO: 12)
GGAAGATCTATAGACAGATGGGGGTGTCGTTTTGGC were used.

In the RACE PCR, one poly dC 5' primer was used for both the heavy and light chain, EcoPolydC: TATATCTA-GAATTCCCCCCCCCCCCCCCCC (SEQ ID NO:13), while the degenerate 5' end PCR primers were Sac1MK: GGGAGCTCGAYATTGTGMTSACMCARWCTMCA (SEQ ID NO:14) for the light chain and an equal mix of EcoR1MH1: CTTCCGGAATTCSARGTNMAGCTGSAG-SAGTC (SEQ ID NO:15) and EcoR1MH2: CTTCCG-GAATTCSARGTNMAGCTGSAGSAGTCWGG (SEQ ID NO:16) for the heavy chain (mixed bases: H=A+T+C, S=G+C, Y=C+T, K=G+T, M=A+C, R=A+G, W=A+T, V=A+C+G, N=A+T+G+C).

The PCR reactions were performed on an MJ research thermocycler using a program adapted from Wang et al. (2000, *J. Immunol. Methods.* 233:167-177): 1) 94° C., 3 min; 2) 94° C., 15 sec; 3) 45° C., 1 min; 4) 72° C., 2 min; 5) cycle back to step #2 29 times; 6) finish with a final extension step at 72° C. for 10 min. The PCR products were cloned into pBluescript II SK+ (Stratagene) using restriction enzymes created by the PCR primers. Heavy and light chain clones were sequenced by Lark Technologies or Seqwright sequencing services.

The RACE PCR was never successful for the My9-6 light chain. Thus, in order to confirm the 5' end cDNA sequences, additional degenerate PCR and cloning was done. The My9-6 light chain cDNA sequence, determined from the degenerate PCR clones, was entered into the NCBI's Blast search website (ncbi.nlm.nih.gov/BLAST/) and the top five murine antibody sequences with signal sequence submitted were saved. Degenerate PCR primers were designed from these signal peptides using the Codehop web software (blocks.fhcrc.org/codehop.html). EcoRI restriction sites were added to three of the Codehop degenerate primers (FIG. 2) and these were used in RT-PCR reactions as described above.

1.3. Preparation and Sequencing of Heavy and Light Chain Samples

The heavy and light chains of muMy9-6 antibody were separated by SDS-PAGE under reducing conditions. The reduced and denatured antibody was electrophoresed on a 12% Tris-glycine gel (Novex, San Diego, Calif.). After electrophoresis, the gels were blotted onto an Immobilon$^{psq}$ membrane using CAPS/MeOH buffer. After transfer, the membranes were stained with Ponseau S. The bands corresponding to the light and heavy chains were excised for protein sequencing.

The light chain of the antibody was sequenced directly from the membrane by automated Edman degradation chemistry on an ABI 494 Procise sequencer.

The N-terminus of the heavy chain was blocked, thus the protein was digested, in situ, with trypsin according to Gharandaghi, et al. (1996). The digest mixture was then analyzed by MALDI-TOF mass spectrometry on a Kratos Kompact SEQ instrument. Selected peptides were subjected to MS/MS to determine their sequences.

Example 2. Humanization of Antibody Variable Region by Resurfacing

Resurfacing of the My9-6 antibody to provide humanized versions suitable as therapeutic or diagnostic agents generally proceeds according to the principles and methods disclosed in U.S. Pat. No. 5,639,641, and as follows.

2.1. Surface Prediction

The solvent accessibility of the variable region residues for a set of antibodies with solved structures was used to predict the surface residues for the murine My9-6 antibody variable region. The amino acid solvent accessibility for a set of 127 unique antibody structure files (FIG. 3) were calculated with the MC software package (Pedersen et al., 1994, *J. Mol. Biol.* 235(3):959-973). The ten most similar light chain and heavy chain amino acid sequences from this set of 127 structures was determined using sequence alignment software on the NCBI website ncbi.nlm.nih.gov/BLAST/. The average solvent accessibility for each variable region residue of these ten antibody variable regions was calculated with an Excel spreadsheet and positions with greater than a 30% average accessibility were considered surface residues. Positions with average accessibilities of between 25% and 35% were further considered by calculating the individual residue accessibility for only those structures with two identical residues flanking on either side.

2.2. Molecular Modeling

A molecular model of the variable region of murine My9-6 was generated using the Oxford Molecular software package AbM. The antibody framework was built from structure files for the antibodies with the most similar amino acid sequences (1sbs for the light chain and 1bbj for the heavy chain) and the non-canonical CDRs were built by searching a C-α structure database containing non-redundant solved structures. Models were viewed with the GlaxoSmithKline Swiss-Pdb Viewer and residues that lie within 5 Å of a CDR were determined.

2.3. Human Antibody Selection

The surface positions of the murine My9-6 variable region were compared to the corresponding positions in human antibody sequences in the Kabat database (Johnson and Wu, 2001, Nucleic Acids Res. 29(1):205-6). The antibody database management software SR (Searle, 1998) was used to extract and align the surface residues from natural heavy and light chain human antibody pairs. The human antibody variable region surface with the most identical surface residues, with special consideration given to positions that come within 5 Å of a CDR, was chosen to replace the murine My9-6 antibody variable region surface residues.

2.4. Construction of Humanized Antibody Gene by PCR Mutagenesis

PCR mutagenesis was performed on the murine My9-6 variable region cDNA clones to first change the 5' end sequences to match the peptide sequence, and then build the resurfaced, human My9-6 gene. Primer sets were designed to create the murine residues not originally sequenced in the initial degenerate PCR clones (light chain positions N1, M3, L4, and S7, and heavy chain positions Q3 and P7).

Humanization primer sets were designed to make the 6 amino acid changes required for all versions of huMy9-6 and additional primers were designed to alternatively change the four 5 Å residues (FIG. 4). PCR reactions were performed on an MJ Research thermocycler with the following program: 1) 94° C., 1 min; 2) 94° C., 15 sec; 3) 55° C., 1 min; 4) 72° C., 1 min; 5) cycle back to step #2 29 times; 6) finish with a final extension step at 72° C. for 4 min. The PCR products were digested with their corresponding restriction enzymes and cloned into the pBluescript cloning vectors. Clones were sequenced to confirm the amino acid changes.

2.5. Expression Vector for Humanized Antibodies

Figure 5:
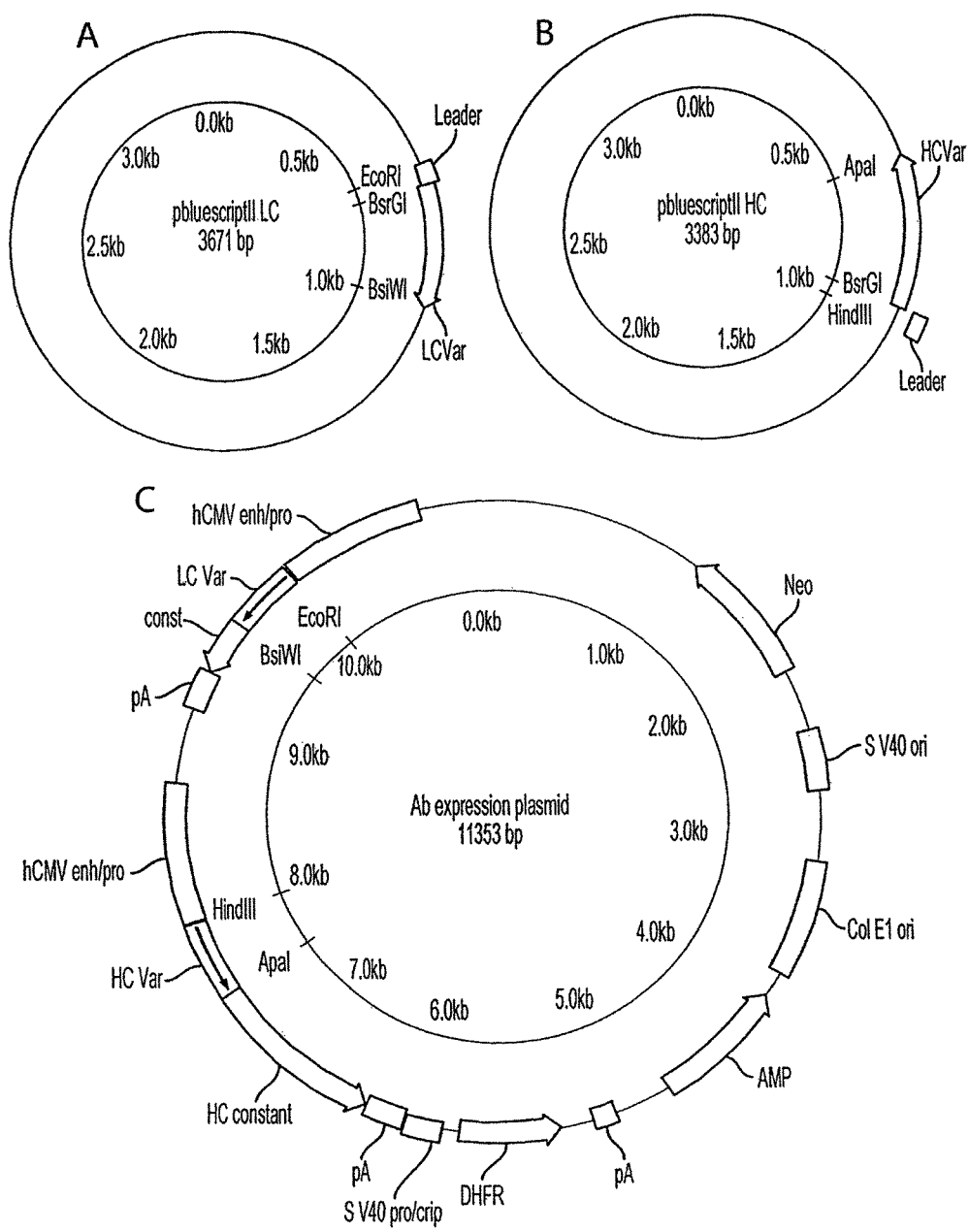
FIG. 5 shows the plasmids used to build and express the humanized antibodies. (A): the light chain cloning plasmid. (B): the heavy chain cloning plasmid. (C): the mammalian antibody expression plasmid.

The light and heavy chain paired sequences were cloned into a single mammalian expression vector. The PCR primers for the human variable sequences created restriction sites that allowed the human signal sequence to be added in the pBluescriptII cloning vector. The variable sequences could then be cloned into the mammalian expression plasmid with EcoRI and BsiWI or HindIII and ApaI for the light chain or heavy chain respectively (FIG. 5). The light chain variable sequences were cloned in-frame onto the human IgKappa constant region and the heavy chain variable sequences were cloned into the human IgGammal constant region sequence. In the final expression plasmids, human CMV promoters drive the expression of both the light and heavy chain cDNA sequences.

2.6. Transient Expression of Humanized Antibodies 293T cells were cultured in Dulbecco's Modified Eagle Medium (DMEM, BioWhittaker, 12-614F), 10% heat-inactivated fetal bovine serum (Hyclone, SH30071.03), 4 mM L-glutamine (BioWhittaker, 17-604E), and 1% penicillin/streptomycin mixture (BioWhittaker, 17-603E) under 6% $CO_2$ in a 37° C. incubator. The cells were split three times per week at a 1:10 dilution maintaining a sub-confluent population. 24 hours prior to transfection, cells were trypsinized (BioWhittaker, 17-161E); live cells were counted by the trypan blue exclusion method and plated on 10 cm, tissue culture treated plates (Corning, 430167) at a density of $2 \times 10^6$ cells per plate. Immediately prior to transfection, cells were washed gently with phosphate buffered saline (PBS, diluted from BioWhittaker 10×PBS, 17-517Q) and cells were overlayed with 7 mL of Hybridoma SFM (InvitroGen, 12045-076) including 1% Ultra Low IgG Serum (Gibco BRL, 16250-078).

The transient transfection methods were adapted from the standard Qiagen Polyfect protocol. For one 10 cm plate to be transfected, 8 μg of CsCl grade DNA was combined with 300 μL Hybridoma SFM and 80 μL Polyfect transfection reagent (Qiagen, 301107). The transfection mix was vortexed for about 5 seconds on low speed and incubated for 5 minutes at ambient temperature. After incubation, 1 mL of Hybridoma SFM, 1% Ultra Low IgG Serum was added to the transfection mix and combined by pipetting up and down about five times. Transfection mix was then added to the 7 mL Hybridoma SFM covering the cells and plates were swirled gently to insure even distribution. The transfection reactions were incubated over-night, generally 16 hours, in a tissue culture incubator. The transfection media was then carefully removed from the cells and replaced with 20 mL of Hybridoma SFM, 1% Ultra Low IgG. The transfected cells were then returned to the incubator for 72 hours, after which the supernatants were harvested and antibody production quantitated by ELISA. Harvested supernatant was stored at 4° C. until purification.

2.7. Purification of Humanized Antibodies

Supernatant was prepared for Protein A affinity chromatography by the addition of ¹/₁₀ volume of 1 M Tris/HCl buffer, pH 8.0. The pH-adjusted supernatant was filtered through a 0.22 μm filter membrane and loaded onto a Protein A Sepharose column (HiTrap Protein A HP, 1 mL, Amersham Biosciences) equilibrated with binding buffer (PBS, pH 7.3). A Q-Sepharose precolumn (10 mL) was connected upstream of the Protein A column during sample loading to reduce contamination from cellular material such as DNA. Following sample loading, the pre-column was removed and the Protein A column orientation was reversed for wash and elution. The column was washed with binding buffer until a stable baseline was obtained with no absorbance at 280 nm. Antibody was eluted with 0.1 M acetic acid buffer containing 0.15 M NaCl, pH 2.8, using a flow rate of 0.5 mL/min. Fractions of approximately 0.25 mL were collected and neutralized by the addition of ¹/₁₀ volume of 1M Tris/HCl, pH 8.0. The peak fraction(s) was dialysed overnight against PBS, pH 7.3. The amount of antibody was quantified by measuring absorbance at 280 nm and the antibody concentration was calculated assuming that $E_{280}^{0.1\%} = 1.4$. Absorbance spectra analysis and SDS-PAGE were conducted on antibody fractions to verify their purity.

Example 3. Testing of Humanized Antibodies

3.1. Growth of Cells for Binding Analysis

HL-60 cells were obtained from the American Type Culture Collection (ATCC#CCL-240). They were maintained in a 5% $CO_2$ atmosphere, 37° C. water-jacketed incubator (Napco Scientific Co., Tualitan, Oreg.). The cells were grown in RPMI media supplemented with L-glutamine (BioWhittaker, Walkersville, Md.) containing 10% fetal bovine serum (Hyclone, Logan, Utah), plus 50 µg/mL of gentamicin sulfate (Life Technologies, Grand Island, N.Y.).

3.2. Direct Binding Assay on HL-60 Cells

HL-60 cells were harvested from T75 flasks (NUN-CLON™, cat. no. 153732), and centrifuged at about 300×g for five minutes in an Omnifuge RT tabletop centrifuge (Haereus Separations, Germany), at 4° C. The cells were resuspended at a density of $3\times10^6$ cells per mL in FACS buffer, comprised of 2% (v/v) goat serum (Sigma Chemical Co., St Louis, Mo.) in MEM Alpha Medium, supplemented with L-glutamine (Life Technologies, Grand Island, N.Y.). Using a multichannel pipetor, $3\times10^5$ cells were added to wells of a Falcon 96-well round bottom plate (cat. no. 3077) and then placed on ice. Using a Falcon 96-well flexible assay plate (cat. no. 353911), eleven twofold serial dilutions of each test or control article were prepared in duplicate in FACS buffer, from a starting concentration of $2\times10^{-8}$ M. Then, 100 µl of either test or control article was mixed with the cells. Control wells only received FACS buffer. The plate was incubated on ice for one hour, and then centrifuged for five minutes at 300× g, in a refrigerated centrifuge. Reagents were removed from the plate wells by quick inversion over a waste beaker containing 10% bleach. The cells were resuspended by gentle vortexing, washed once with cold FACS buffer, centrifuged, and then resuspended with gentle vortexing. FITC labeled goat-anti-human IgG (Jackson ImmunoResearch Laboratories, West Grove, Pa., cat. no. 109-096-003) and FITC labeled goat-anti-mouse IgG (Jackson ImmunoResearch Laboratories, West Grove, Pa., cat. no. 109-095-088) were diluted 1:100 in FACS buffer, and 100 µl was added to appropriate wells on the assay plate. The plate was then incubated for an additional hour on ice, protected from light. Unbound secondary antibody was washed from the wells in the same manner as described above. The cells were resuspended by gentle vortexing, and then fixed by adding 120 µl/well of 1% formaldehyde in phosphate-buffered saline (PBS, 10 mM potassium phosphate, 150 mM sodium chloride, pH 7.2). The assay plate was then analyzed on a FACScan flow cytometer interfaced with an automated 96-well sampling device (Becton Dickinson, Mountain View, Calif.).

3.3. Preparation of Plasma Membranes

Plasma membranes were prepared according to the procedure described in Vater et al. (1995). Briefly, HL-60 cells were grown to a density of $1\times10^6$ cells/mL in RPMI supplemented with L-glutamine, containing 10% fetal bovine serum, and 50 µg/mL of gentamicin sulfate. When a total of $1\times10^9$ cells was obtained, cells were harvested, spun at about 300× g in an Omnifuge RT centrifuge, washed with Hanks balanced salt solution (Life Technologies, cat. no. 14175-095), and combined into one 50 mL conical centrifuge tube. The pellet was then frozen at −80° C. for at least 24 hours, to facilitate cell lysis and homogenization. To prepare plasma membranes, the pellet was thawed quickly at 37° C., and then stored on ice; all subsequent steps were performed at 4° C. The HL-60 cell pellet was resuspended in 8 mL of 10 mM Tris-HCl buffer, pH 7.0, containing 1 mM EDTA, 0.25 M sucrose, and 1 mM phenylmethylsulfonyl-fluoride (PMSF). The cell pellet was then transferred to a 15 mL Dounce tissue grinder (Wheaton, Millville, N.J.) for cellular disruption (20 strokes with a tight fitting borosilicate glass pestle). The homogenate was centrifuged in a Sorval RC-5B Refrigerated Superspeed Centrifuge, using an SS-34 rotor (Wilmington, Del.) at 6000 rpm for ten minutes, and the supernatant carefully removed from the pellet. The pellet was washed an additional time with 8 mL of buffer and processed as described above. The combined supernatants were layered over a 1 mL 37% sucrose cushion buffer in 10 mM Tris-HCl, 1 mM PMSF, 1 mM EDTA, pH 7.0, and processed further in a pre-chilled Beckman L8-M ultracentrifuge, with an SW55ti rotor (Beckman Instruments, Palo Alto, Calif.), at 33,000 rpm for 70 minutes. The opalescent membrane layer, sitting just above the sucrose cushion, was removed from each tube and diluted with four volumes of 10 mM Tris-HCl, 1 mM EDTA, 1 mM PMSF, pH 7.0. This solution was then centrifuged for an additional 30 minutes at 18,000 rpm in the ultracentrifuge. The supernatant was carefully drawn off, and the resultant pellets were resuspended in 10 mM Tris-HCl, 1 mM EDTA, 1 mM PMSF, pH 7.0. The HL-60 membrane preparation was aliquoted into 1.5 mL sterile screw cap Eppendorf tubes, frozen in liquid nitrogen, and then stored at −80° C. for use. The total protein concentration of the final preparation was determined using the Pierce™ BCA Assay (Pierce Chemical Company, Rockford, Ill., cat. no. 23235).

3.4. Direct Binding Assay on HL-60 Membranes

HL-60 membranes, prepared as described above, were dried at a starting concentration of 10 µg/mL in deionized water onto the polystyrene surface of Immulon 2 96-well assay plates (Dynex Laboratories, Chantilly, Va.), using a Labconco vacuum desiccator (Labconco, Corp, Kansas City, Mo.), overnight at ambient temperature. The ELISA plate was then blocked with a 1% fraction V bovine serum albumin (Sigma-Aldrich, Inc., St. Louis, Mo., cat. no. A-3294), 0.05% Tween-20 (Sigma-Aldrich, Inc., St. Louis, Mo., cat. no. P-2287) solution in Tris-buffered saline (50 mM Tris-HCl, 150 mM sodium chloride, pH 7.5, TBS), 300 µL per well, at 37° C. for 1 hour. Following this blocking step, the plate was drained of blocking buffer and blotted onto paper towels. Two, threefold serial dilutions of test or control reagents were prepared in blocking buffer, in quadruplicate, starting at $3.13\times10^{-9}$ M titrated down to $5.29\times10^{-14}$ M on a flexible 96-well assay plate. The negative control wells contained blocking buffer alone. 50 µL of each dilution was transferred to designated wells on the membrane-coated assay plate that was then incubated overnight at 4° C. The well contents were then aspirated into a waste flask containing 10% (v/v) bleach, and the plate washed 3× with TBS containing 0.1% (v/v) Tween-20 (wash buffer) and blotted on paper towels. The amount of bound anti-My9-6 antibody was detected with either goat anti-mouse IgG-HRP or donkey anti-human IgG-HRP diluted 1:1000 with blocking buffer in the appropriate wells. These secondary antibodies were incubated on the assay plate for one hour at room temperature, protected from light. The plate was washed and blotted as before. The plate was developed using TMB (BioFX Laboratories, Randallstown, Md., cat. no. TMBW-0100-01), then quenched with Stop solution (BioFX Laboratories, Randallstown, Md., cat. no. STPR-0100-01). The assay plate was read at A450 nm using a TITERTEK® Multiskan Plus MK II plate reader (Huntsville, Ala.).

3.5. Competition Binding Assay on HL-60 Membranes

HL-60 membranes, prepared as described above, were dried down from a starting concentration of 10 µg/mL in deionized water on the polystyrene surface of Immulon 2 96-well assay plates (Dynex Laboratories, Chantilly, Va.), using a Labconco vacuum desiccator (Labconco, Corp, Kansas City, Mo.), overnight at room temperature. The ELISA plate was then blocked with a 1% fraction V bovine serum albumin (Sigma-Aldrich, Inc., St. Louis, Mo., cat. no. A-3294), 0.05% Tween-20 (Sigma-Aldrich, Inc., St. Louis, Mo., cat. no. P-2287) solution in Tris-buffered saline (50 mM tris, 150 mM sodium chloride, pH 7.5, TBS), 300 µl per well, at 37° C. for 1 hour. Following this blocking step, the plate was drained of blocking buffer and blotted onto paper towels. Two twofold serial dilutions of test or control reagents were prepared in blocking buffer, in quadruplicate, starting at $1.25 \times 10^{-8}$ M titrated down to $2.44 \times 10^{-11}$ M ($2 \times$ the final concentration needed) on a flexible 96-well assay plate. These unlabeled competing reagents were then mixed with an equal volume of $2.5 \times 10^{-10}$ M biotinylated murine anti-My9-6 (ImmunoGen, Inc., Cambridge, Mass.); the positive control contained no competing reagent, whereas the negative control contained blocking buffer alone. 50 µL of these mixtures was transferred to designated wells on the membrane-coated assay plate that was then incubated overnight at 4° C. The well contents were then aspirated into a waste flask containing 10% (v/v) bleach, and the plate washed 3× with TBS containing 0.1% (v/v) Tween-20 (wash buffer). The plate was blotted onto paper towels, and the amount of bound biotinylated murine anti-My9-6 was detected with 100 µL per well of streptavidin-alkaline phosphatase (Jackson ImmunoResearch Laboratories, West Grove, Pa., cat. no. 016-050-084), diluted 1:5,000 in blocking buffer. Following a one hour incubation at room temperature and protected from light, the unbound secondary antibody reagent was washed from the wells, and the plate was developed using TMB (BioFX Laboratories, Randallstown, Md., cat. no. TMBW-0100-01) quenched with Stop solution (BioFX Laboratories, Randallstown, Md., cat. no. STPR-0100-01). The assay plate was read at A450 nm using a TITERTEK® Multiskan Plus MK II plate reader (Huntsville, Ala.).

3.6. Cloning Murine My9-6 Antibody Variable Regions

The murine My9-6 antibody variable regions were cloned by the RT-PCR methods described above. Several individual light and heavy chain clones were sequenced to identify and avoid possible polymerase generated sequence errors. Only a single sequence was obtained for the light chain, but two separate sequences were pulled out of the heavy chain RT-PCR clones.

To confirm the actual sequences of the murine My9-6 light chain variable region, peptide sequences were analyzed by Edman degradation, Matrix Assisted Laser Desorption Ionisation (MALDI) and Tandem Mass Spectrometry (MS-MS). The 22 residues at the amino terminus of the My9-6 light chain were sequenced by Edman degradation and are given in FIG. 6A. The initial cDNA sequence derived from degenerate RT-PCR clones matched all but four residues that were likely generated by the degenerate primers. The peptide sequence determined by Edman degradation was later confirmed by RT-PCR clones generated by degenerate primers in the 5' end signal peptide sequence. MS-MS analysis of tryptic digest fragments also confirmed the sequence of the light chain CDRs 1 and 2 (FIG. 6B). Together, these peptide analyses confirm the predicted murine My9-6 light chain amino acid sequence derived from the RT-PCR generated cDNA clones.

As is common with heavy chain sequences, the muMy9-6 heavy chain amino terminus was blocked by a pyroglutamine residue and therefore could not be sequenced by N-terminal Edman degradation. Instead internal sequence data was generated by tryptic digests and analysis by Matrix Assisted Laser Desorption Ionisation (MALDI) and Tandem Mass Spectrometry (MS-MS). A 1788 dalton fragment was identified with a predicted sequence identical to a portion of cDNA clone 2 (FIG. 7). This sequence includes five residues from CDR3 for cDNA clone 2, and therefore is an ideal peptide to make a positive identification for muMy9-6 heavy chain. Multiple RACE PCR clones producing only the sequence originally obtained from the degenerate RT-PCR clone 2 also confirmed this peptide sequence.

The cumulative results from the various cDNA clones and the peptide sequence analysis provided the final murine My9-6 light and heavy chain sequences presented in FIG. 8. Using Kabat and AbM definitions, the three light chain and heavy chain CDRs were identified (FIGS. 8 and 9). A search of the NCBI IgBlast database indicates that the muMy9-6 antibody light chain variable region most likely derives from the mouse IgVκ 8-27 germline gene while the heavy chain variable region most likely derives from the IgVh V102 germline gene (FIG. 10).

3.7 Determination of the Variable Region Surface Residues of My9-6 Antibody

Figure 12A:
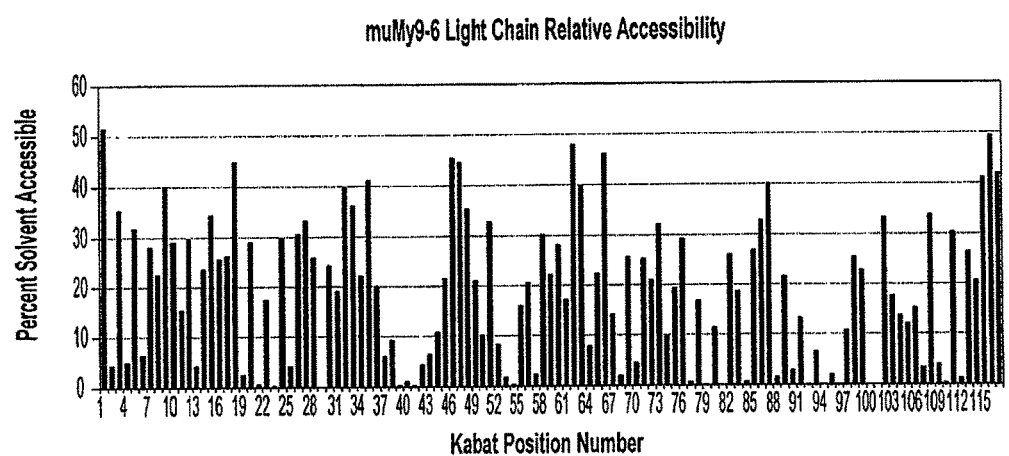
FIGS. 12A & B show the average accessibility for each Kabat position of the muMy9-6 antibody light (A) and heavy (B) chains. The relative solvent accessibilities for each Kabat position of the ten most homologous light and heavy chain sequences were averaged and are presented along the x axis.
Figure 12B:
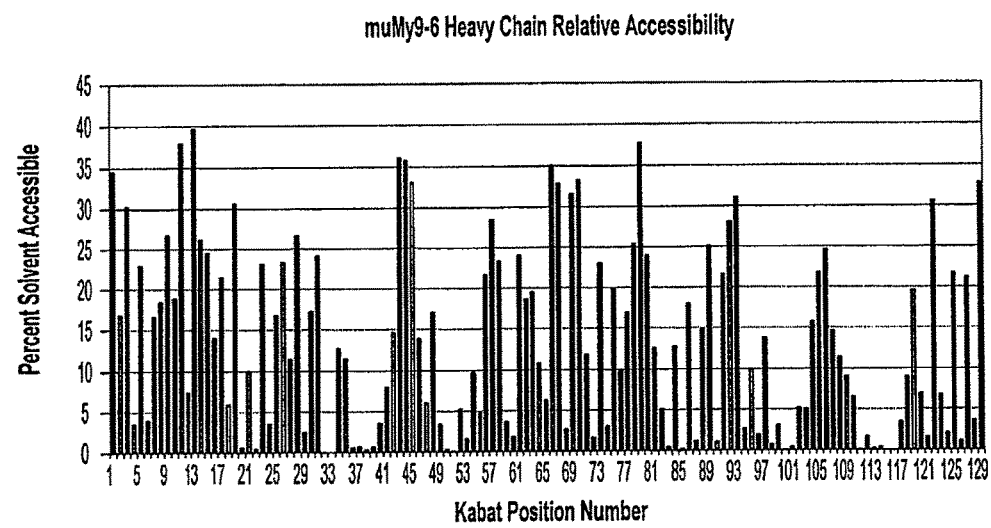

The antibody resurfacing techniques described by Pedersen et al. (1994, *J. Mol. Biol.* 235:959-973) and Roguska et al. (1996, *Protein Eng.* 9:895-904) begin by predicting the surface residues of the murine antibody variable sequences. A surface residue is defined as an amino acid that has at least 30% of its total surface area accessible to a water molecule. In the absence of a solved structure to find the surface residues for muMy9-6, the ten antibodies with the most homologous sequences in the set of 127 antibody structure files were aligned (FIGS. 11A & B). The solvent accessibility for each Kabat position was averaged for these aligned sequences and the distribution of the relative accessibilities for each residue are presented in FIG. 12.

Several surface positions had average accessibilities of between 25% and 35%. These were looked at more closely by averaging only the antibodies with two identical residues flanking on either side (FIGS. 13A and B). The 25 predicted surface residues for the muMy9-6 heavy chain were unchanged after the additional analysis, but Kabat positions 15 and 70 in the light chain required further consideration. The alanine at light chain position 15 had an average accessibility of 34.4% in all ten structures, but only a single structure, 1mcp, had identical flanking residues to those in muMy9-6. In this structure, Ala15 had a relative accessibility of only 18.2%. Because in this single structure Ala15 was dramatically less accessible than the average residue for position 15, the three structures with only a single difference in the flanking residues (1ap2, 1frg, and 1 hil) were also averaged together. The average accessibility for these three structures was again 33.3%, making Ala15 a predicted surface residue. Finally, resurfaced anti-B4, C242, and the resurfacing patent itself predict that light chain position 15 is a surface residue. Taken together, the conservative approach is to assume that muMy9-6 light chain position 15 is a surface residue.

The muMy9-6 light chain position 70 also required special considerations that ultimately resulted in a conservative prediction of it being a surface residue. The initial surface prediction work for the light chain was done with MC data from only the five most homologous light chain structures, and in this group Asp70 was a predicted surface residue.

Later, with the additional five most homologous structures, position 70 was found to have an average accessibility of 29.1% as shown in FIG. 13A. In addition, nine of the ten structures had the identical flanking residues and the average of this set was 29.2% accessible. Because this residue appeared to be so close to the 30% cut off and the resurfacing patent calls position 70 a surface position, the accessibility data was further scrutinized. Position 70 for the structure 1lve has a relative accessibility of 22.5%, which is five percentage points less than the next lowest relative accessibility of 27.2%. Since 1lve is the eighth most homologous structure and it was a low outlier, an average was taken for the eight structures with identical flanking residues besides 1lve and this set had a 30.1% average accessibility. This, together with the fact that the initial muMy9-6 light chain analysis and the resurfacing patent call light chain position 70 a surface position, led to the conservative prediction that the muMy9-6 light chain Asp70 is a surface residue.

3.8. Molecular Modeling to Determine Which Residues Fall Within 5 Å of a CDR

The molecular model, generated with the AbM software package, was analyzed to determine which muMy9-6 surface residues come within 5 Å of a CDR. In order to resurface the antibody, all surface residues outside of a CDR must be changed to it's human counterpart, but residues that come within 5 Å of a CDR may also contribute to antigen binding and specificity. Therefore these 5 Å residues must be identified and considered throughout the humanization process. The CDR definitions used for resurfacing combines the AbM definition for heavy chain CDR2 and Kabat definitions for the remaining five CDRs (FIG. 9). The murine model was analyzed with the Swiss Viewer Software and FIG. 14 shows the residues that are within 5 Å of any CDR residue in either the light or heavy chain sequence.

3.9. Selection of the Most Homologous Human Surface

Candidate human antibody surfaces for resurfacing muMy9-6 were pulled from the Kabat antibody sequence database using SR software. This software provides an interface to search only specified residue positions against the antibody database. To preserve the natural pairs, the surface residues of both the light and heavy chains were compared together. The most homologous human surfaces from the Kabat database were aligned in order of rank of sequence identity. The top five surfaces as aligned by the SR Kabat database software are given in FIG. 15. The surfaces were then compared to identify which human surfaces would require the least changes within 5 Å of a CDR. The anti-Hepatitis C Virus antibody, LC3bPB (Ivanovski M. et al., 1998, *Blood* 91(7):2433-42), requires the least number of surface residue changes (10 total) and only four of these residues come within 5 Å of a CDR. The full length variable region sequence for muMy9-6 was also aligned against the Kabat human antibody database with SR and LC3bPB was identified as the 14th most similar human variable region sequence (data not shown). Since the LC3bPB antibody provides the most homologous surface and requires the least number of 5 Å residue changes, it is the best candidate to resurface muMy9-6.

3.10. Construction of the My9-6 Genes for Humanized My9-6 Antibodies

The ten surface residue changes for huMy9-6 were made using PCR mutagenesis techniques as described above. Since six of the surface residues for LC3bPB were more than 5 Å from a CDR, these residues were changed from murine to human in all versions for humanized My9-6 (FIGS. 16A and B). The four surface residues that did fall within 5 Å of a CDR, Kabat light chain positions 1, 3 and 45 and heavy chain position 64, were either changed to human or retained as murine to make up the 16 humanized versions of My9-6. Of these, the most human is version 1.0 since it has all ten human surface residues. The most conservative version in terms of ensuring maximum binding affinity is version 1.1 which retains the four murine surface residues that are within 5 Å of a CDR. Each of the humanized My9-6 antibody genes were cloned into the antibody expression plasmid (FIG. 5) for transient and stable transfections.

3.11. Binding Data

The key strength of humanization by resurfacing is that by retaining the non-surface murine framework residues, humanized My9-6 should continue to bind CD33 with unchanged affinity. However, the four surface residues that come within 5 Å of a CDR may contribute to antigen binding and, therefore, changing these residues could have a negative effect on binding. To address this concern, the 16 versions of humanized My9-6 include all combinations of either the human or murine residues at each of the four 5 Å residue positions. These range from the optimal or most human version, 1.0, with human residues at every non-CDR surface position, to the most conservative version, 1.1, which retains the murine residues in each of the four 5 Å surface positions and, therefore, should retain wild-type binding. By comparing the binding affinity of the humanized My9-6 versions to murine My9-6, the most human version that retains wild-type binding can be selected as the resurfaced, humanized My9-6.

Direct and competitive binding experiments with the humanized versions of murine My9-6 and with muMy9-6 were done on the CD33 expressing human leukemic cell line, HL-60. The three most human versions (V1.0, V1.3, V1.6) as well as the most conservative version (V1.1) were tested on either HL-60 membranes or whole cells. FIG. 17 gives the KD values for each condition and FIG. 18 shows example binding curves for huMy9-6, V1.0, versus muMy9-6. The KD values calculated for the humanized My9-6 versions including the most human, version 1.0, fall within the experimental error of the KD value of murine My9-6. The competitive binding results also demonstrate that huMy9-6 antibodies can compete equally well for CD33 binding as muMy9-6 itself. With these data demonstrating near wild type binding affinities for the fully humanized My9-6, V1.0, on HL-60 membranes and whole cells, there was no need to test additional versions, since version 1.0 is the optimal humanized My9-6 antibody.

The murine My9-6 antibody has been fully humanized without loss of binding activity. None of the surface residue changes from mouse to human resulted in a loss of binding affinity, even though four of these surface residues were within 5 Å of a CDR. Residues within 5 Å of a CDR are thought to make potentially critical van der Waal contacts that may affect the structure of these CDRs.

The results of the My9-6 humanization suggest that as the numbers of resurfaced antibodies grow, a thorough residue position analysis based on actual binding data might become a more effective way of targeting questionable residues than simply looking to any residue within 5 Å of a CDR.

Humanized My9-6 V1.0 (huMy9-6) is the fourth antibody that was humanized using the procedure described herein. Humanization by resurfacing of the variable region framework of a murine antibody was developed as an improvement upon standard humanization methods, including CDR grafting, which can require extensive development and reengineering to maintain binding activity. This is contrasted by the resurfaced huMy9-6 antibody, which involved changing only ten surface residues to create a fully active antibody with a completely human surface.

Example 4. My9-6-DM1 Immunoconjugate

Preclinical efficacy studies with human tumor xenografts in mice using the My9-6 antibody conjugated to the maytansinoid drug DM1 were performed.

As discussed below, My9-6-DM1 maintained the specificity and binding affinity of the unmodified antibody for CD33, and showed potent antigen-specific cytotoxicity toward CD33-positive tumor cells in vitro. Treatment of SCID mice bearing established subcutaneous HL-60 tumor xenografts with My9-6-DM1, resulted in complete eradication of the tumors at doses (20 mg conjugated antibody/kg/day i.v. ×5 days) which showed no toxicity and were well below the maximum tolerated dose. In contrast, treatment with My9-6 antibody alone had no effect on HL-60 tumor growth compared to vehicle control. Similar curative efficacy was observed with My9-6-DM1 upon treatment of mice bearing subcutaneous THP-1 xenografts.

4.1. Reagents

The antibody was the murine monoclonal My9-6 antibody directed against human CD33 described above.

The antibody modifying agent was N-succinimidyl 4-(2-pyridyldithio)pentanoate (SPP):

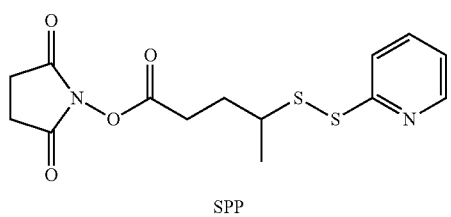 [SMILES: CC(CCC(=O)ON1C(=O)CCC1=O)SSc1ccccn1 ; "SPP"]

SPP

The cytotoxic drug was the maytansine analog, DM1, which is synthesized from a microbial fermentation product, Ansamitocin P3. DM1 is a potent inhibitor of tubulin polymerization.

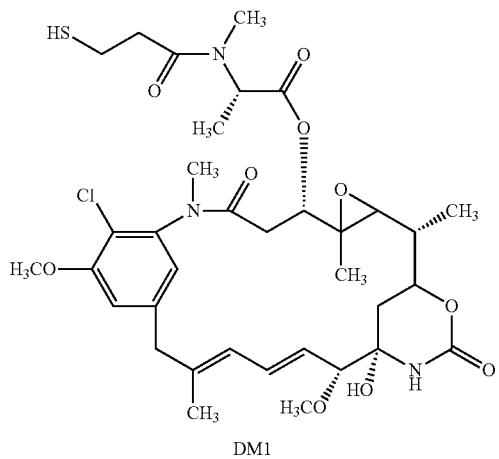

DM1

4.2. Preparation of My9-6-DM1

My9-6-DM1 was prepared by modifying the My9-6 antibody with SPP to introduce 3-5 pyridyldithio groups per molecule of antibody. Disulfide exchange between the thiol substituent on the DM1 and the active disulfide functionality on the antibody provided the DM1-containing antibody conjugate.

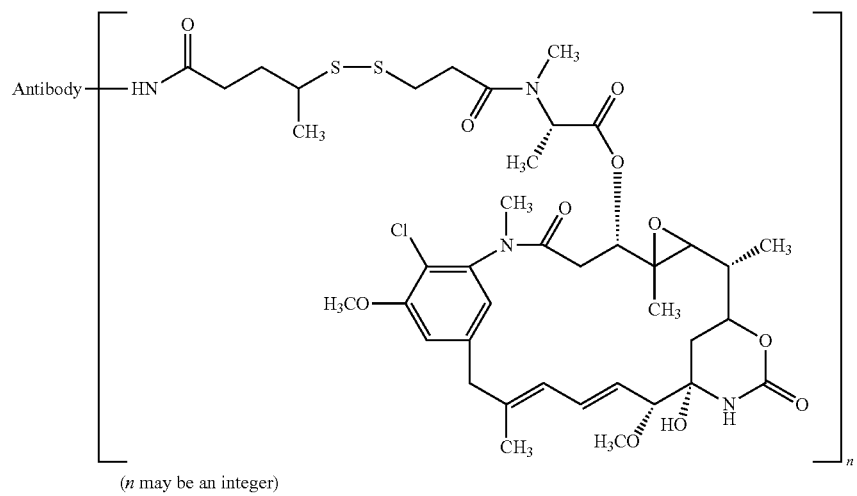

($n$ may be an integer)

4.3. Analysis of Antibody and Antibody Conjugate Binding by Blow-Cytometry

Figure 19:
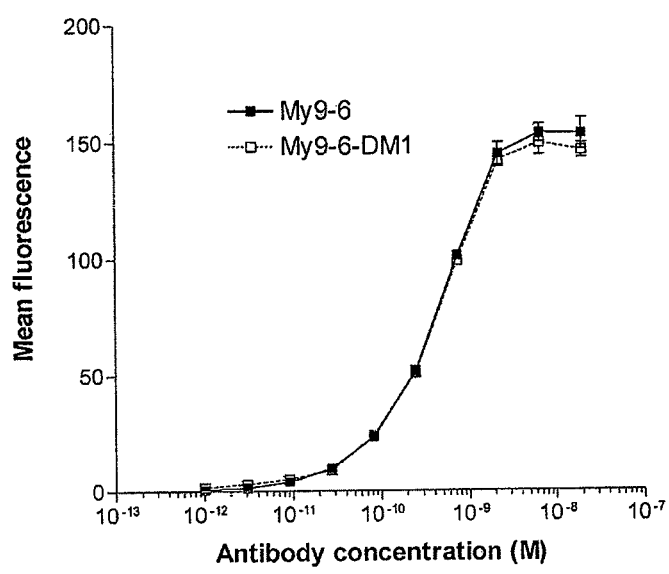
FIG. 19 shows a comparison of binding of My9-6-DM1 with My9-6 antibody on HL-60 cells.

HL-60 cells were incubated with various concentrations of either My9-6 antibody or My9-6-DM1. The cells were then washed and incubated with a secondary FITC-labeled anti-murine IgG antibody. Following an additional wash, cells were fixed with 2% formaldehyde and cell-associated fluorescence was quantified using a BD FACScan flow cytometer. My9-6-DM1 maintains specific CD33 binding comparable to the unmodified antibody (FIG. 19).

4.4. In Vitro Cytotoxicity Assay

The cytotoxicity of My9-6-DM1 was measured using the CD33-expressing THP-1 cell and the CD33-negative cell line Namalwa. Cells were plated in 96-well plates in media containing the conjugate and incubated at 37° C. until colonies had formed (2-3 weeks). Colonies were then scored, and the surviving fractions determined using Poisson distribution in the calculations.

4.5. In Vivo Mouse Tumor Xenograft Studies

Subcutaneous tumor model—HL-60 human promyelocytic leukemia cells ($5 \times 10^6$ cells in 0.1 mL) were subcutaneously inoculated into the right flank of female SCID mice. Mice were treated by intravenous injection into a lateral tail vein starting when tumors reached 100 mm³ in size (400 mm³ in large tumor model). Tumor size and mouse body weight were measured twice per week. Survival model—HL-60 cells ($5 \times 10^6$ cells in 0.1 mL) were intravenously injected into the lateral tail vein of female SCID mice. Eleven days after tumor cell injection treatment was started. Mice were checked every day for moribund, tumor mass, or death. Body weight was measured twice per week.

4.6. In Vitro Specificity and Efficacy of My9-6-DM1

Figure 20:
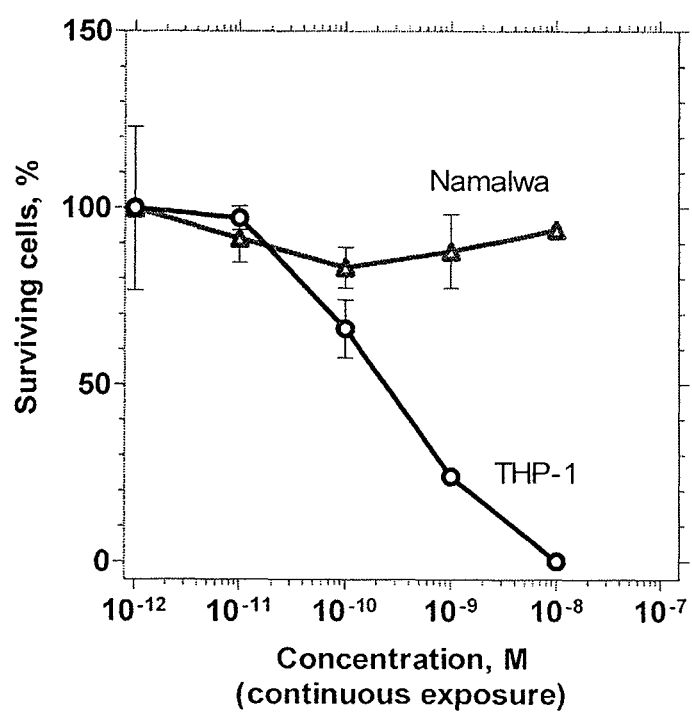
FIG. 20 shows in vitro cytotoxicity of My9-6-DM1 toward CD33-expressing human tumor cells.

The cytotoxicity of My9-6-DM1 toward CD33 expressing cells (THP-1) compared to a CD33-negative cell line (Namalwa) was tested using a clonogenic assay, where cell killing activity is determined by quantifying the number of colonies that can grow following treatment. My9-6-DM1 exhibits potent cell killing activity toward CD33-positive human tumor cells in vitro (FIG. 20). No significant toxicity toward CD33-negative cells was observed, indicating that the CD33-dependent cytotoxicity was due to specific targeting by the anti-CD33 antibody, My9-6.

4.7. Efficacy of My9-6-DM1 Against Human Tumor Xenografts in Mice

Figure 21:
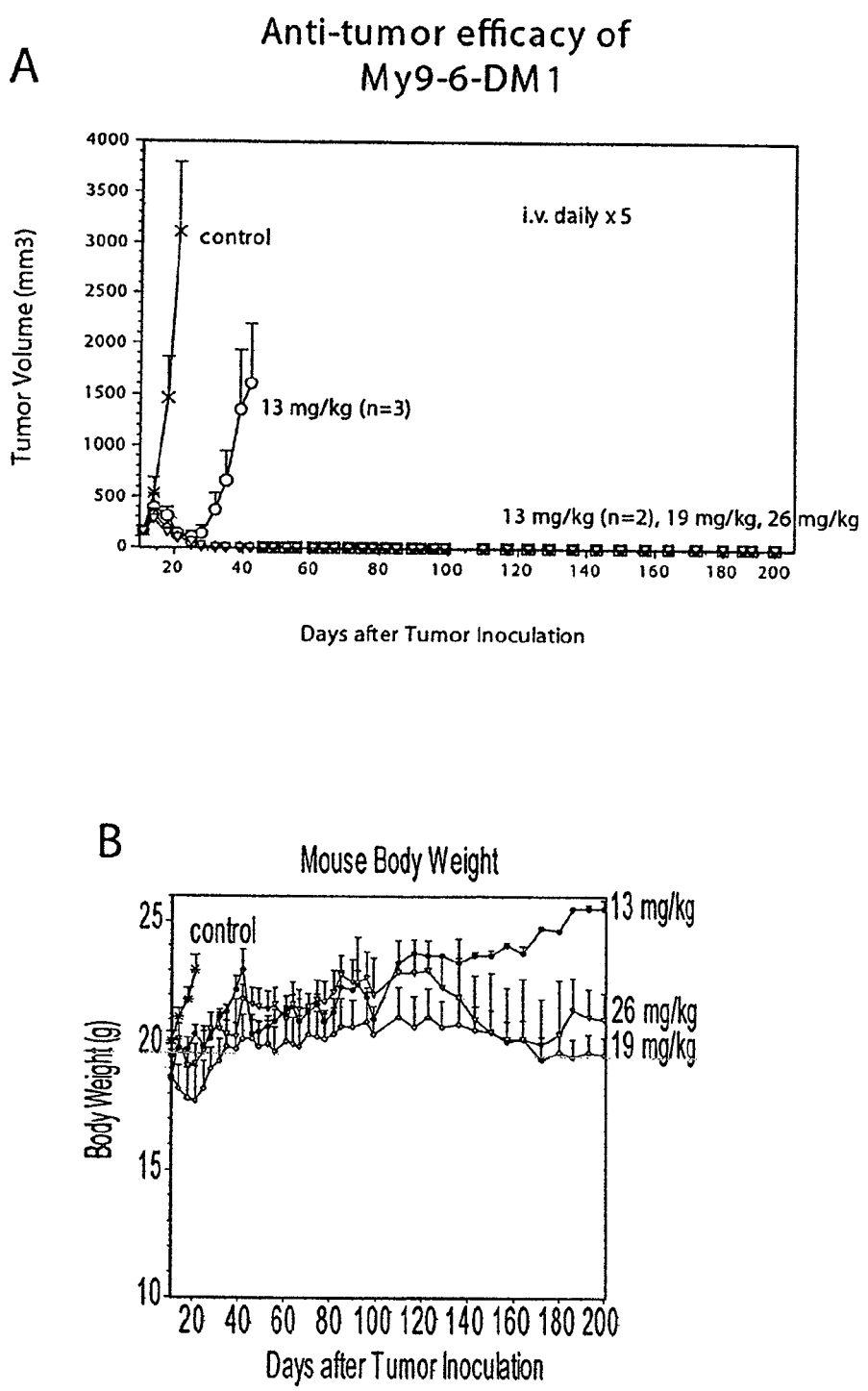
FIG. 21 shows the results of efficacy experiments of My9-6-DM1 in SCID mice bearing HL-60 xenografts. The effect of My9-6-DM1 (A) and unmodified My9-6 antibody (C) on the growth of HL-60 tumors was evaluated. Mouse body weight was monitored as an indication of toxicity (B, D).
Figure 21:
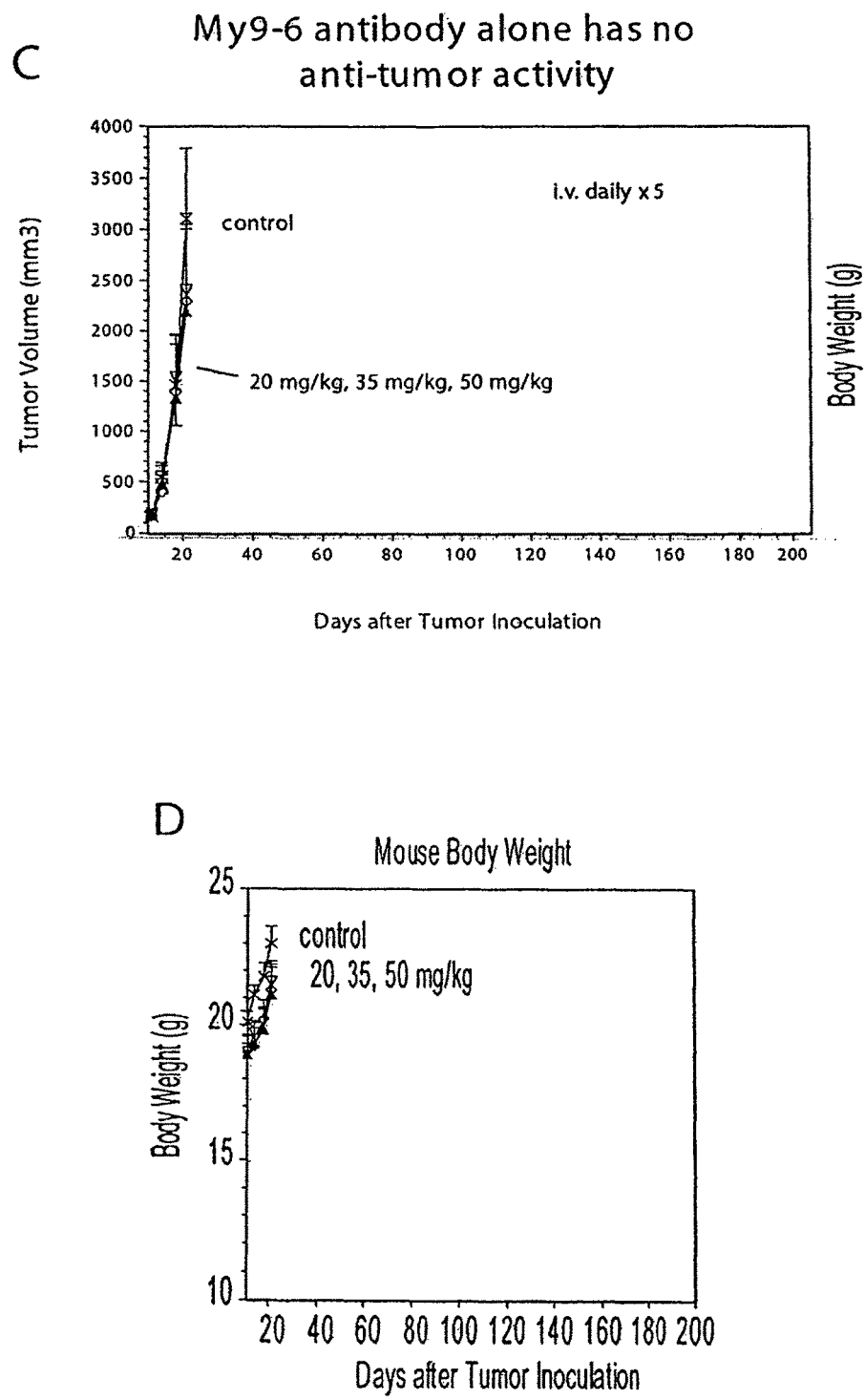

The efficacy of My9-6-DM1 in vivo was determined using SCID mice bearing human HL-60 tumor cell xenografts. HL-60 cells were injected subcutaneously and tumors were allowed to grow to an average size of 100 mm³. My9-6-DM1 conjugate was delivered i.v. once a day for 5 days at the doses indicated in FIG. 21. Dosage is expressed as mg antibody in the conjugate, which corresponds to a DM1 dose of approximately 15 μg DM1 per mg of antibody. Tumor volume was measured as an indication of treatment efficacy and mouse body weight was monitored to indicate toxicity due to treatment. My9-6-DM1 induces long-term cures of mice bearing human HL-60 cell xenografts at doses that cause little toxicity (FIG. 21). At the two highest doses tested (19 and 26 mg/kg), complete regression of the tumors was observed with a maximum body weight loss of less than 10% (FIGS. 21A and B). Even at the lowest dose tested (13 mg/kg), 2 of 5 mice showed complete cures, while the other 3 mice showed tumor regression with tumor growth delayed by approximately 20 days. Similar results were also observed using the THP-1 leukemic cell line where My9-6-DM1 induced long-term cures of mice bearing human THP-1 tumor xenografts (data not shown).

These results are in sharp contrast to those obtained by treatment with My9-6 antibody alone. Antibody alone has no effect on tumor cell growth even at 50 mg/kg (FIG. 21C).

The activity of My9-6-DM1 was compared with the approved anti-CD33 antibody-calicheamicin conjugate Gemtuzumab ozogamicin. Gemtuzumab ozogamicin was administered every 4 days for 3 doses. A preliminary experiment demonstrated that Gemtuzumab ozogamicin at the published MTD for nude mice (0.3 mg/kg) was too toxic for SCID mice (data not shown). Significant toxicity was also observed at the 100 and 200 μg/kg dose in this experiment (FIG. 21F). Gemtuzumab ozogamicin showed only modest tumor regression and growth delay in this model (about 25 days) at the maximum tolerated dose (100 μg/kg) (FIG. 21E).

In a separate experiment, the anti-tumor activity of the My9-6-DM1 conjugate was compared to the activity of the unconjugated parent drug, maytansine. Mice bearing HL-60 tumor xenografts were treated daily for 5 days with conjugate at 23 mg antibody/kg or 350 μg DM1/kg; unconjugated drug at 350 μg/kg; or unconjugated antibody at 23 mg/kg. Three of 6 mice treated with maytansine alone died two days after treatment indicating that this level of drug is quite toxic. However, the drug showed a significant impact on tumor growth in the remaining 3 mice, with a delay in growth of approximately 10 days (FIG. 22).

My9-6 antibody alone had no affect on tumor growth, while My9-6-DM1 conjugate caused complete regression of the tumors. The effect of conjugate treatment on mouse body weight (12% decrease) was slightly greater than in the previous experiment and may reflect batch to batch variation in conjugate synthesis. Regrowth of tumors in two of the six conjugate-treated mice was observed starting at day 70. These animals were subjected to a second treatment of My9-6-DM1 identical to the first treatment. The second treatment resulted in the complete regression of the "relapsing" tumors with no adverse toxicity observed, suggesting that the regrowth of tumor was not due to the growth of conjugate-resistant cells.

Figure 23A:
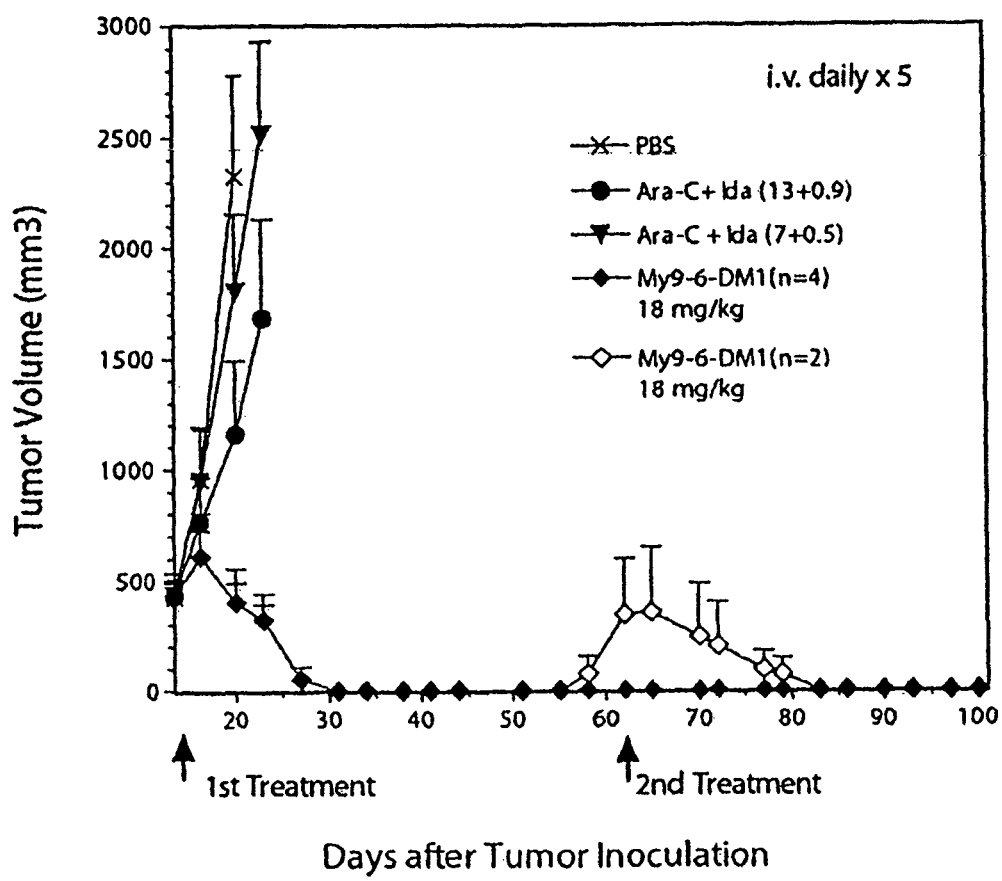
FIGS. 23A & B show a comparison of anti-tumor efficacy of My9-6-DM1 with standard chemotherapy in SCID mice bearing large HL-60 xenografts (A). Mouse body weight was monitored as an indication of toxicity (B). Relapsed tumors in two treated mice were retreated with a second course of My9-6-DM1.
Figure 23B:
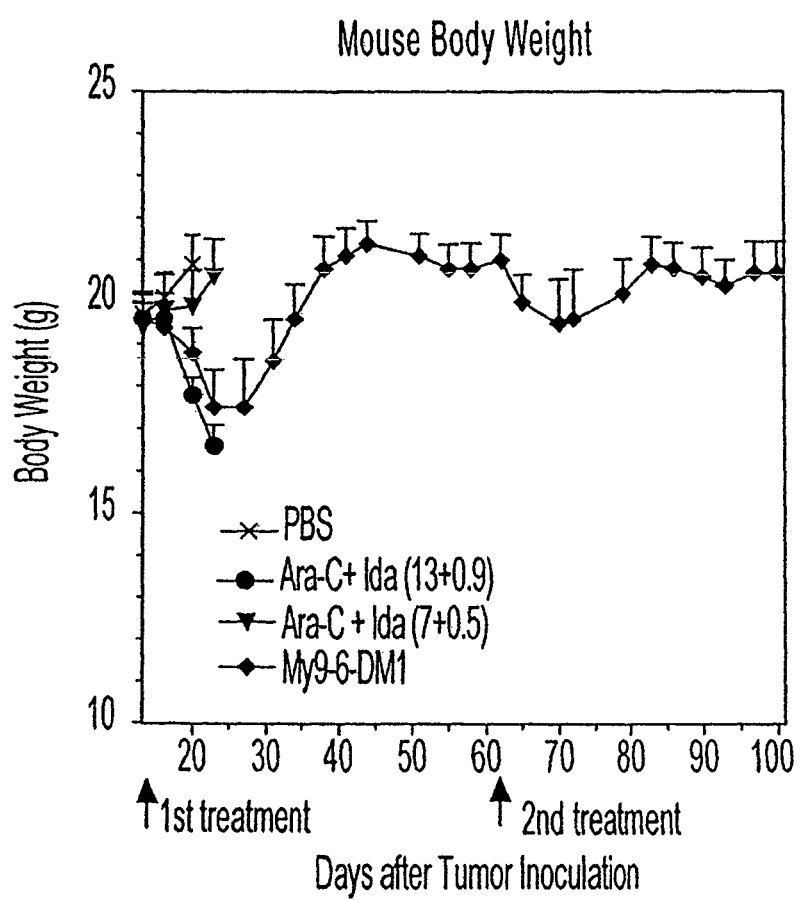

The potent efficacy of My9-6-DM1 in this xenograft model suggested that the conjugate may be effective even against large HL-60 tumors. Tumors were allowed to grow to a tumor volume of >400 mm³ prior to the initiation of treatment. In addition, a comparison of the activity of My9-6-DM1 with standard chemotherapeutic drugs was conducted. My9-6-DM1 caused complete regression of large tumors in SCID mice (FIGS. 23A & B). Again, relapsed tumors (2 of 6 mice) were sensitive to a second treatment of My9-6-DM1. Treatment with standard chemotherapeutic agents (Ara-C and idarubicin) had little effect on tumor growth. Higher drug doses were profoundly toxic to the mice (not shown).

4.8. Efficacy of My9-6-DM1 in HL-60 Cell Mouse Survival Model

Figure 24A:
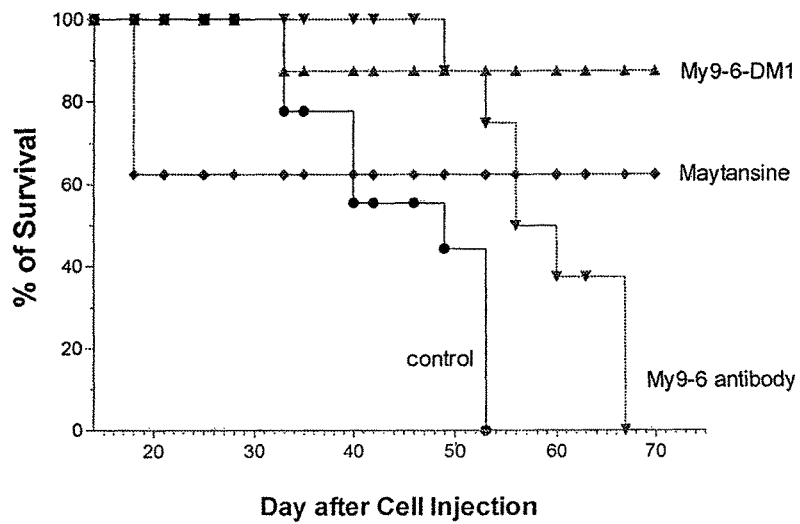
FIGS. 24A & B show anti-tumor efficacy of My9-6-DM1 compared with Gentuzumab ozogamicin and standard chemotherapy in an HL-60 survival model. HL-60 cells were intravenously injected into SCID mice. Indicated treatments were started 11 days following injection of cells. Treatments were i.v. daily ×5 except for Gentuzumab ozogamicin (Q4D×3).
Figure 24B:
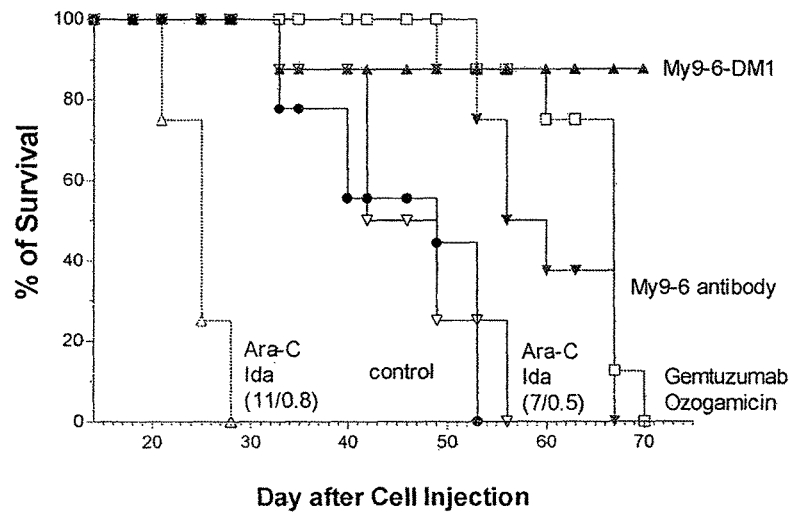

While the efficacy of My9-6-DM1 in the tumor xenograft model is striking, it is also of interest to look at the activity of the conjugate in a mouse survival model where HL-60 cells are injected directly into a mouse tail vein. In this model, control mice die between 30 and 50 days after cell injection. Mice treated with My9-6-DM1 starting 11 days after cell injection showed a dramatic increase in survival, with 7 of 8 mice alive at 70 days (FIG. 24A). Maytansine alone also showed significant impact on mouse survival in this model, though 2 of 8 mice died shortly after the start of treatment indicating drug toxicity. The relative efficacy of maytansine in this model compared to the subcutaneous xenograft model suggests that HL-60 tumors may be more sensitive to the action of the drug in this setting. A further delay in the start of treatment may demonstrate a sharper differential between targeted and untargeted drug. However, even in this model, standard chemotherapy provided no significant survival enhancement (FIG. 24B). The highest combination dose showed significant apparent drug toxicity. Both My9-6 antibody alone and Gemtuzumab ozogamicin showed a modest increase in survival.

Statement of Deposit

The hybridoma that makes murine My9-6 antibodies was deposited with the American Type Culture Collection, PO Box 1549, Manassas, Va. 20108, on Nov. 7, 2002, under the Terms of the Budapest Treaty and was assigned deposit number PTA-4786.

Certain patents and printed publications have been referred to in the present disclosure, the teachings of which are hereby each incorporated in their respective entireties by reference.

While the invention has been described in detail and with reference to specific embodiments thereof, it will be apparent to one of ordinary skill in the art that various changes and modifications can be made thereto without departing from the spirit and scope thereof.

What is claimed is:

1. An isolated antibody or epitope-binding fragment thereof that specifically binds CD33, wherein the antibody or epitope-binding fragment thereof comprises:
   (a) a heavy chain (HC) CDR1 comprising the amino acid sequence of GYTFTSYYIH (SEQ ID NO: 58), a HC CDR2 comprising the amino acid sequence of VIYPGNDDIS (SEQ ID NO: 59), and a HC CDR3 comprising the amino acid sequence of EVRLRYFDV (SEQ ID NO: 3); and
   (b) a light chain (LC) CDR1 comprising the amino acid sequence of KSSQSVFFSSSQKNYLA (SEQ ID NO: 4), a LC CDR2 comprising the amino acid sequence of WASTRES (SEQ ID NO: 5), and a LC CDR3 comprising the amino acid sequence of HQYLSSRT (SEQ ID NO: 6).

2. The antibody or epitope-binding fragment of claim 1, wherein the antibody or epitope-binding fragment thereof comprises a LC variable region comprising the amino acid sequence of SEQ ID NO: 8.

3. The antibody or epitope-binding fragment of claim 1, wherein the antibody or epitope-binding fragment thereof comprises a LC variable region comprising the amino acid sequence of SEQ ID NO:10.

4. A pharmaceutical composition comprising the antibody or epitope-binding fragment thereof of claim 1 and a pharmaceutically acceptable agent.

5. An isolated humanized or resurfaced antibody or epitope-binding fragment thereof that specifically binds to CD33, wherein the antibody or epitope-binding fragment thereof comprises:
   (a) a heavy chain (HC) CDR1 comprising the amino acid sequence of GYTFTSYYIH (SEQ ID NO: 58), a HC CDR2 comprising the amino acid sequence of VIYPGNDDIS (SEQ ID NO: 59), and a HC CDR3 comprising the amino acid sequence of EVRLRYFDV (SEQ ID NO: 3); and
   (b) a light chain (LC) CDR1 comprising the amino acid sequence of KSSQSVFFSSSQKNYLA (SEQ ID NO: 4), a LC CDR2 comprising the amino acid sequence of WASTRES (SEQ ID NO: 5), and a LC CDR3 comprising the amino acid sequence of HQYLSSRT (SEQ ID NO: 6); and
   wherein the antibody or epitope-binding fragment thereof comprises a heavy chain variable region having at least 95% sequence identity to the amino acid sequence of SEQ ID NO: 9 and a light chain variable region having at least 95% sequence identity to the amino acid sequence of SEQ ID NO: 10, wherein the HC CDR1, CDR2, CDR3 and LC CDR1, CDR2, and CDR3 are unchanged.

6. The antibody or epitope-binding fragment thereof of claim 5, wherein the HC variable region comprises the amino acid sequence of SEQ ID NO: 9 and wherein the LC variable region comprises the amino acid sequence of SEQ ID NO: 10.

7. A pharmaceutical composition comprising the antibody or epitope-binding fragment thereof of claim 5 and a pharmaceutically acceptable agent.

8. An immunoconjugate comprising an antibody or epitope-binding fragment thereof that specifically binds to CD33 linked to a drug or prodrug, wherein the antibody or epitope-binding fragment thereof comprises:
   (a) a heavy chain (HC) CDR1 comprising the amino acid sequence of GYTFTSYYIH (SEQ ID NO: 58), a HC CDR2 comprising the amino acid sequence of VIYPGNDDIS (SEQ ID NO: 59), and a HC CDR3 comprising the amino acid sequence of EVRLRYFDV (SEQ ID NO: 3); and
   (b) a light chain (LC) CDR1 comprising the amino acid sequence of KSSQSVFFSSSQKNYLA (SEQ ID NO: 4), a LC CDR2 comprising the amino acid sequence of WASTRES (SEQ ID NO: 5), and a LC CDR3 comprising the amino acid sequence of HQYLSSRT (SEQ ID NO: 6).

9. The immunoconjugate of claim 8, wherein the antibody or epitope-binding fragment thereof comprises a HC variable region comprising the amino acid sequence of SEQ ID NO: 7 and a LC variable region comprising the amino acid sequence of SEQ ID NO: 8.

10. The immunoconjugate of claim 8, wherein the antibody or epitope-binding fragment thereof comprises a HC variable region comprising the amino acid sequence of SEQ ID NO: 9 and a LC variable region comprising the amino acid sequence of SEQ ID NO: 10.

11. The immunoconjugate of claim 8, wherein the drug or prodrug is selected from the group consisting of a maytansinoid, a taxoid, CC-1065, a CC-106 analog, dolastatin, a dolastatin analog, methotrexate, daunorubicin, doxorubicin, vincristine, vinblastine, melphalan, mitomycin C, chlorambucil, and calicheamicin.

12. The immunoconjugate of claim 8, wherein the drug or prodrug is linked to the antibody or epitope-binding fragment thereof through a linking group selected from the group consisting of a disulfide group, a thioether group, an acid labile group, a photolabile group, a peptidase labile group, and an esterase labile group.

13. A pharmaceutical composition comprising the immunoconjugate of claim 8 and a pharmaceutically acceptable agent.

14. An immunoconjugate comprising a humanized or resurfaced antibody or epitope-binding fragment thereof that specifically binds to CD33 linked to a drug or prodrug, wherein the antibody or epitope-binding fragment thereof comprises:
(a) a heavy chain (HC) CDR1 comprising the amino acid sequence of GYTFTSYYIH (SEQ ID NO: 58), a HC CDR2 comprising the amino acid sequence of VIYPGNDDIS (SEQ ID NO: 59), and a HC CDR3 comprising the amino acid sequence of EVRLRYFDV (SEQ ID NO: 3); and
(b) a light chain (LC) CDR1 comprising the amino acid sequence of KSSQSVFFSSSQKNYLA (SEQ ID NO: 4), a LC CDR2 comprising the amino acid sequence of WASTRES (SEQ ID NO: 5), and a LC CDR3 comprising the amino acid sequence of HQYLSSRT (SEQ ID NO: 6); and
wherein the antibody or epitope-binding fragment thereof comprises a HC variable region having at least 95% sequence identity to the amino acid sequence of SEQ ID NO: 9 and a LC variable region having at least 95% sequence identity to the amino acid sequence of SEQ ID NO: 10, wherein the HC CDR1, CDR2, CDR3 and LC CDR1, CDR2, and CDR3 are unchanged.

15. The immunoconjugate of claim 14, wherein the HC variable region comprises the amino acid sequence of SEQ ID NO: 9 and wherein the LC variable region comprises the amino acid sequence of SEQ ID NO: 10.

16. A pharmaceutical composition comprising the immunoconjugate of claim 14 and a pharmaceutically acceptable agent.

17. A diagnostic reagent comprising the antibody or epitope-binding fragment thereof of claim 1, wherein the antibody or epitope-binding fragment is labeled.

18. The diagnostic reagent of claim 17, wherein the label is selected from the group consisting of a biotin label, an enzyme label, a radio-label, a fluorophore, a chromophore, an imaging agent, and a metal ion.

* * * * *

SEQUENCE LISTING

<160> NUMBER OF SEQ ID NOS: 96

<210> SEQ ID NO 1
<211> LENGTH: 5
<212> TYPE: PRT
<213> ORGANISM: Mus musculus

<400> SEQUENCE: 1

Ser Tyr Tyr Ile His
1               5

<210> SEQ ID NO 2
<211> LENGTH: 17
<212> TYPE: PRT
<213> ORGANISM: Mus musculus
<220> FEATURE:
<221> NAME/KEY: MISC_FEATURE
<222> LOCATION: (16)..(16)
<223> OTHER INFORMATION: "X" may be K or Q

<400> SEQUENCE: 2

Val Ile Tyr Pro Gly Asn Asp Asp Ile Ser Tyr Asn Gln Lys Phe Xaa
1               5                   10                  15

Gly

<210> SEQ ID NO 3
<211> LENGTH: 9
<212> TYPE: PRT
<213> ORGANISM: Mus musculus

<400> SEQUENCE: 3

Glu Val Arg Leu Arg Tyr Phe Asp Val
1               5

<210> SEQ ID NO 4
<211> LENGTH: 17
<212> TYPE: PRT
<213> ORGANISM: Mus musculus

<400> SEQUENCE: 4

Lys Ser Ser Gln Ser Val Phe Phe Ser Ser Ser Gln Lys Asn Tyr Leu
1               5                   10                  15

Ala

<210> SEQ ID NO 5
<211> LENGTH: 7
<212> TYPE: PRT
<213> ORGANISM: Mus musculus

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Mus musculus

<400> SEQUENCE: 6

His Gln Tyr Leu Ser Ser Arg Thr
1               5

<210> SEQ ID NO 7
<211> LENGTH: 118

<212> TYPE: PRT
<213> ORGANISM: Mus musculus

<400> SEQUENCE: 7

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
                20                  25                  30

Tyr Ile His Trp Ile Lys Gln Thr Pro Gly Gln Gly Leu Glu Trp Val
            35                  40                  45

Gly Val Ile Tyr Pro Gly Asn Asp Asp Ile Ser Tyr Asn Gln Lys Phe
        50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
                100                 105                 110

Thr Val Thr Val Ser Ser
            115

<210> SEQ ID NO 8
<211> LENGTH: 113
<212> TYPE: PRT
<213> ORGANISM: Mus musculus

<400> SEQUENCE: 8

Asn Ile Met Leu Thr Gln Ser Pro Ser Ser Leu Ala Val Ser Ala Gly
1               5                   10                  15

Glu Lys Val Thr Met Ser Cys Lys Ser Ser Gln Ser Val Phe Phe Ser
                20                  25                  30

Ser Ser Gln Lys Asn Tyr Leu Ala Trp Tyr Gln Gln Ile Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Ile Tyr Tyr Cys His Gln
                85                  90                  95

Tyr Leu Ser Ser Arg Thr Phe Gly Gly Gly Thr Lys Leu Glu Ile Lys
                100                 105                 110

Arg

<210> SEQ ID NO 9
<211> LENGTH: 118
<212> TYPE: PRT
<213> ORGANISM: Artificial Sequence
<220> FEATURE:
<223> OTHER INFORMATION: Humanized My9-6 antibody heavy chain variable
      region

<400> SEQUENCE: 9

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
                20                  25                  30

Tyr Ile His Trp Ile Lys Gln Thr Pro Gly Gln Gly Leu Glu Trp Val
            35                  40                  45

```
Gly Val Ile Tyr Pro Gly Asn Asp Asp Ile Ser Tyr Asn Gln Lys Phe
        50                  55                  60

Gln Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Gln Gly Thr
                100                 105                 110

Thr Val Thr Val Ser Ser
            115

<210> SEQ ID NO 10
<211> LENGTH: 113
<212> TYPE: PRT
<213> ORGANISM: Artificial Sequence
<220> FEATURE:
<223> OTHER INFORMATION: Humanized My9-6 antibody light chain variable
      region

<400> SEQUENCE: 10

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
                20                  25                  30

Ser Ser Gln Lys Asn Tyr Leu Ala Trp Tyr Gln Gln Ile Pro Gly Gln
            35                  40                  45

Ser Pro Arg Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg

<210> SEQ ID NO 11
<211> LENGTH: 46
<212> TYPE: DNA
<213> ORGANISM: Artificial Sequence
<220> FEATURE:
<223> OTHER INFORMATION: PCR primer HindKL

<400> SEQUENCE: 11
tatagagctc aagcttggat ggtgggaaga tggatacagt tggtgc          46

<210> SEQ ID NO 12
<211> LENGTH: 36
<212> TYPE: DNA
<213> ORGANISM: Artificial Sequence
<220> FEATURE:
<223> OTHER INFORMATION: PCR primer Bgl2IgG1

<400> SEQUENCE: 12
ggaagatcta tagacagatg ggggtgtcgt tttggc                      36

<210> SEQ ID NO 13
<211> LENGTH: 30
<212> TYPE: DNA
<213> ORGANISM: Artificial Sequence
```

```
<220> FEATURE:
<223> OTHER INFORMATION: PCR primer EcoPolydC

<400> SEQUENCE: 13
tatatctaga attcccccc ccccccccc                                              30

<210> SEQ ID NO 14
<211> LENGTH: 32
<212> TYPE: DNA
<213> ORGANISM: Artificial Sequence
<220> FEATURE:
<223> OTHER INFORMATION: PCR primer Sac1MK

<400> SEQUENCE: 14
gggagctcga yattgtgmts acmcarwctm ca                                          32

<210> SEQ ID NO 15
<211> LENGTH: 32
<212> TYPE: DNA
<213> ORGANISM: Artificial Sequence
<220> FEATURE:
<223> OTHER INFORMATION: PCR primer EcoR1MH1
<220> FEATURE:
<221> NAME/KEY: misc_feature
<222> LOCATION: (18)..(18)
<223> OTHER INFORMATION: "n" may be any nucleotide

<400> SEQUENCE: 15
cttccggaat tcsargtnma gctgsagsag tc                                          32

<210> SEQ ID NO 16
<211> LENGTH: 35
<212> TYPE: DNA
<213> ORGANISM: Artificial Sequence
<220> FEATURE:
<223> OTHER INFORMATION: PCR primer EcoR1MH2
<220> FEATURE:
<221> NAME/KEY: misc_feature
<222> LOCATION: (18)..(18)
<223> OTHER INFORMATION: "n" may be any nucleotide

<400> SEQUENCE: 16
cttccggaat tcsargtnma gctgsagsag tcwgg                                       35

<210> SEQ ID NO 17
<211> LENGTH: 34
<212> TYPE: DNA
<213> ORGANISM: Artificial Sequence
<220> FEATURE:
<223> OTHER INFORMATION: Degenerate primer Leaddeg1
<220> FEATURE:
<221> NAME/KEY: misc_feature
<222> LOCATION: (26)..(26)
<223> OTHER INFORMATION: "n" may be any nucleotide
<220> FEATURE:
<221> NAME/KEY: misc_feature
<222> LOCATION: (29)..(29)
<223> OTHER INFORMATION: "n" may be any nucleotide

<400> SEQUENCE: 17
ttttgattct gctgtgggtg tccggnacnt gygg                                        34

<210> SEQ ID NO 18
<211> LENGTH: 33
<212> TYPE: DNA
<213> ORGANISM: Artificial Sequence
<220> FEATURE:
<223> OTHER INFORMATION: Degenerate primer Leaddeg2
<220> FEATURE:
```

```
<221> NAME/KEY: misc_feature
<222> LOCATION: (28)..(28)
<223> OTHER INFORMATION: "n" may be any nucleotide
<220> FEATURE:
<221> NAME/KEY: misc_feature
<222> LOCATION: (31)..(31)
<223> OTHER INFORMATION: "n" may be any nucleotide

<400> SEQUENCE: 18
ttttgattcg ctgctgctgc tgtgggtnws ngg                           33

<210> SEQ ID NO 19
<211> LENGTH: 39
<212> TYPE: DNA
<213> ORGANISM: Artificial Sequence
<220> FEATURE:
<223> OTHER INFORMATION: Degenerate primer Leaddeg3
<220> FEATURE:
<221> NAME/KEY: misc_feature
<222> LOCATION: (31)..(31)
<223> OTHER INFORMATION: "n" may be any nucleotide
<220> FEATURE:
<221> NAME/KEY: misc_feature
<222> LOCATION: (34)..(34)
<223> OTHER INFORMATION: "n" may be any nucleotide

<400> SEQUENCE: 19
ttttgattcc caggtgttca tgctgctgyt nytntgggt                     39

<210> SEQ ID NO 20
<211> LENGTH: 39
<212> TYPE: DNA
<213> ORGANISM: Artificial Sequence
<220> FEATURE:
<223> OTHER INFORMATION: Humanization primer My96LCBsrG1

<400> SEQUENCE: 20
tacaggtgta cactccgata ttgtgatcac ccagactcc                     39

<210> SEQ ID NO 21
<211> LENGTH: 35
<212> TYPE: DNA
<213> ORGANISM: Artificial Sequence
<220> FEATURE:
<223> OTHER INFORMATION: Humanization primer My96LCOL1

<400> SEQUENCE: 21
actggaaatc aaacgaactg tggctgcacc atctg                         35

<210> SEQ ID NO 22
<211> LENGTH: 35
<212> TYPE: DNA
<213> ORGANISM: Artificial Sequence
<220> FEATURE:
<223> OTHER INFORMATION: Humanization primer My96LCOL2

<400> SEQUENCE: 22
gccacagttc gtttgatttc cagtttggtg cctcc                         35

<210> SEQ ID NO 23
<211> LENGTH: 39
<212> TYPE: DNA
<213> ORGANISM: Artificial Sequence
<220> FEATURE:
<223> OTHER INFORMATION: Humanization primer My96HCBsrG1

<400> SEQUENCE: 23
tacaggtgta cactcccagg ttaagctgca gcagtctgg                     39
```

<210> SEQ ID NO 24
<211> LENGTH: 29
<212> TYPE: DNA
<213> ORGANISM: Artificial Sequence
<220> FEATURE:
<223> OTHER INFORMATION: Humanization primer My96HCOL1

<400> SEQUENCE: 24
ccacggtcac cgtctcctca gcctccacc                              29

<210> SEQ ID NO 25
<211> LENGTH: 29
<212> TYPE: DNA
<213> ORGANISM: Artificial Sequence
<220> FEATURE:
<223> OTHER INFORMATION: Humanization primer My96HCOL2

<400> SEQUENCE: 25
gaggctgagg agacggtgac cgtggtccc                              29

<210> SEQ ID NO 26
<211> LENGTH: 43
<212> TYPE: DNA
<213> ORGANISM: Artificial Sequence
<220> FEATURE:
<223> OTHER INFORMATION: Humanization primer My9-6LCNMLS

<400> SEQUENCE: 26
caggtgtaca ctccaatatt atgctcaccc agagtccatc atc              43

<210> SEQ ID NO 27
<211> LENGTH: 42
<212> TYPE: DNA
<213> ORGANISM: Artificial Sequence
<220> FEATURE:
<223> OTHER INFORMATION: Humanization primer My9-6HCQP

<400> SEQUENCE: 27
caggtgtaca ctcccaggtt cagctgcagc agcctggggc tg               42

<210> SEQ ID NO 28
<211> LENGTH: 22
<212> TYPE: DNA
<213> ORGANISM: Artificial Sequence
<220> FEATURE:
<223> OTHER INFORMATION: Humanization primer MY96HCQ64-1

<400> SEQUENCE: 28
agaagttcca aggcaaggcc ac                                     22

<210> SEQ ID NO 29
<211> LENGTH: 22
<212> TYPE: DNA
<213> ORGANISM: Artificial Sequence
<220> FEATURE:
<223> OTHER INFORMATION: Humanization primer MY96HCQ64-2

<400> SEQUENCE: 29
cttgccttgg aacttctgat tg                                     22

<210> SEQ ID NO 30
<211> LENGTH: 60
<212> TYPE: DNA
<213> ORGANISM: Artificial Sequence
<220> FEATURE:

<223> OTHER INFORMATION: Humanization primer MY96HCQ105

<400> SEQUENCE: 30
cgatgggccc ttggtggagg ctgaggagac ggtgaccgtg gtcccttggc cccagacatc    60

<210> SEQ ID NO 31
<211> LENGTH: 79
<212> TYPE: DNA
<213> ORGANISM: Artificial Sequence
<220> FEATURE:
<223> OTHER INFORMATION: Humanization primer MY96LCEVGPR

<400> SEQUENCE: 31
aggtgtacac tccgagattg tgctcaccca gagtccagga tctctggctg tgtctccagg    60
agaaagggtc actatgagc                                                 79

<210> SEQ ID NO 32
<211> LENGTH: 48
<212> TYPE: DNA
<213> ORGANISM: Artificial Sequence
<220> FEATURE:
<223> OTHER INFORMATION: Humanization primer MY96LCR45

<400> SEQUENCE: 32
gcctggtacc aacagatacc agggcagtct cctagacttc tgatctac                 48

<210> SEQ ID NO 33
<211> LENGTH: 26
<212> TYPE: DNA
<213> ORGANISM: Artificial Sequence
<220> FEATURE:
<223> OTHER INFORMATION: Humanization primer MY96LCP80-1

<400> SEQUENCE: 33
agcagtgttc aacctgaaga cctggc                                         26

<210> SEQ ID NO 34
<211> LENGTH: 26
<212> TYPE: DNA
<213> ORGANISM: Artificial Sequence
<220> FEATURE:
<223> OTHER INFORMATION: Humanization primer MY96LCP80-2

<400> SEQUENCE: 34
gtcttcaggt tgaacactgc tgatgg                                         26

<210> SEQ ID NO 35
<211> LENGTH: 48
<212> TYPE: DNA
<213> ORGANISM: Artificial Sequence
<220> FEATURE:
<223> OTHER INFORMATION: Humanization primer MY96LCQ100

<400> SEQUENCE: 35
ttttaagctt cgtttgattt ccagtttggt gccttgaccg aacgtccg                 48

<210> SEQ ID NO 36
<211> LENGTH: 34
<212> TYPE: DNA
<213> ORGANISM: Artificial Sequence
<220> FEATURE:
<223> OTHER INFORMATION: Humanization primer My96lcNM

<400> SEQUENCE: 36
caggtgtaca ctccaatatt atgctcaccc agag                                34

<210> SEQ ID NO 37
<211> LENGTH: 48
<212> TYPE: DNA
<213> ORGANISM: Artificial Sequence
<220> FEATURE:
<223> OTHER INFORMATION: Humanization primer MY96LCK45

<400> SEQUENCE: 37
gcctggtacc aacagatacc agggcagtct cctaaacttc tgatctac                48

<210> SEQ ID NO 38
<211> LENGTH: 38
<212> TYPE: DNA
<213> ORGANISM: Artificial Sequence
<220> FEATURE:
<223> OTHER INFORMATION: Humanization primer My96HCApa1

<400> SEQUENCE: 38
cgatgggccc ttggtggagg ctgaggagac ggtgaccg                            38

<210> SEQ ID NO 39
<211> LENGTH: 35
<212> TYPE: DNA
<213> ORGANISM: Artificial Sequence
<220> FEATURE:
<223> OTHER INFORMATION: Humanization primer huMy96LCOL1

<400> SEQUENCE: 39
actggaaatc aaacgtacgg tggctgcacc atctg                              35

<210> SEQ ID NO 40
<211> LENGTH: 35
<212> TYPE: DNA
<213> ORGANISM: Artificial Sequence
<220> FEATURE:
<223> OTHER INFORMATION: Humanization primer huMy96LCOL2

<400> SEQUENCE: 40
gccaccgtac gtttgatttc cagtttggtg ccttg                              35

<210> SEQ ID NO 41
<211> LENGTH: 34
<212> TYPE: DNA
<213> ORGANISM: Artificial Sequence
<220> FEATURE:
<223> OTHER INFORMATION: Humanization primer My96lcEM My96lcNV
      chMy96lcBsiW1

<400> SEQUENCE: 41
caggtgtaca ctccgagatt atgctcaccc agag                               34

<210> SEQ ID NO 42
<211> LENGTH: 34
<212> TYPE: DNA
<213> ORGANISM: Artificial Sequence
<220> FEATURE:
<223> OTHER INFORMATION: Humanization primer My96lcNV

<400> SEQUENCE: 42
caggtgtaca ctccaatatt gtgctcaccc agag                               34

<210> SEQ ID NO 43
<211> LENGTH: 31
<212> TYPE: DNA
<213> ORGANISM: Artificial Sequence

```
<220> FEATURE:
<223> OTHER INFORMATION: Humanization primer chMy96lcBsiW1

<400> SEQUENCE: 43
ttttcgtacg tttgatttcc agtttggtgc c                                  31

<210> SEQ ID NO 44
<211> LENGTH: 23
<212> TYPE: PRT
<213> ORGANISM: Mus musculus
<220> FEATURE:
<221> NAME/KEY: MISC_FEATURE
<222> LOCATION: (23)..(23)
<223> OTHER INFORMATION: "X" may be any amino acid

<400> SEQUENCE: 44

Asn Ile Met Leu Thr Gln Ser Pro Ser Ser Leu Ala Val Ser Ala Gly
 1               5                  10                  15

Glu Lys Val Thr Met Ser Xaa
            20

<210> SEQ ID NO 45
<211> LENGTH: 23
<212> TYPE: PRT
<213> ORGANISM: Mus musculus

<400> SEQUENCE: 45

Asp Ile Val Ile Thr Gln Thr Pro Ser Ser Leu Ala Val Ser Ala Gly
 1               5                  10                  15

Glu Lys Val Thr Met Ser Cys
            20

<210> SEQ ID NO 46
<211> LENGTH: 32
<212> TYPE: PRT
<213> ORGANISM: Artificial Sequence
<220> FEATURE:
<223> OTHER INFORMATION: Degenerate primer Sac1MK

<400> SEQUENCE: 46

Gly Gly Gly Ala Gly Cys Thr Cys Gly Ala Tyr Ala Thr Thr Gly Thr
 1               5                  10                  15

Gly Met Thr Ser Ala Cys Met Cys Ala Arg Trp Cys Thr Met Cys Ala
            20                  25                  30

<210> SEQ ID NO 47
<211> LENGTH: 23
<212> TYPE: PRT
<213> ORGANISM: Mus musculus

<400> SEQUENCE: 47

Asn Ile Met Leu Thr Gln Ser Pro Ser Ser Leu Ala Val Ser Ala Gly
 1               5                  10                  15

Glu Lys Val Thr Met Ser Cys
            20

<210> SEQ ID NO 48
<211> LENGTH: 17
<212> TYPE: PRT
<213> ORGANISM: Mus musculus

<400> SEQUENCE: 48

Lys Ser Ser Gln Ser Val Phe Phe Ser Ser Ser Gln Lys Asn Tyr Leu
 1               5                  10                  15
```

Ala

<210> SEQ ID NO 49
<211> LENGTH: 12
<212> TYPE: PRT
<213> ORGANISM: Mus musculus

<400> SEQUENCE: 49

Ser Ser Gln Ser Val Phe Phe Ser Ser Ser Gln Lys
1               5                   10

<210> SEQ ID NO 50
<211> LENGTH: 12
<212> TYPE: PRT
<213> ORGANISM: Mus musculus

<400> SEQUENCE: 50

Lys Leu Leu Ile Tyr Trp Ala Ser Thr Arg Glu Ser
1               5                   10

<210> SEQ ID NO 51
<211> LENGTH: 11
<212> TYPE: PRT
<213> ORGANISM: Mus musculus

<400> SEQUENCE: 51

Lys Leu Leu Ile Tyr Trp Ala Ser Thr Arg Glu
1               5                   10

<210> SEQ ID NO 52
<211> LENGTH: 19
<212> TYPE: PRT
<213> ORGANISM: Mus musculus

<400> SEQUENCE: 52

Arg Tyr Phe Asp Val Trp Gly Ala Gly Thr Thr Val Thr Val Ser Ser
1               5                   10                  15

Ala Lys Thr

<210> SEQ ID NO 53
<211> LENGTH: 20
<212> TYPE: PRT
<213> ORGANISM: Mus musculus

<400> SEQUENCE: 53

Glu Val Arg Leu Arg Tyr Phe Asp Val Trp Gly Ala Gly Thr Thr Val
1               5                   10                  15

Thr Val Ser Ser
            20

<210> SEQ ID NO 54
<211> LENGTH: 19
<212> TYPE: PRT
<213> ORGANISM: Mus musculus

<400> SEQUENCE: 54

Met Gly Glu Asp Ala Met Asp Tyr Trp Gly Gln Gly Thr Ser Val Thr
1               5                   10                  15

Val Ser Ser

<210> SEQ ID NO 55
<211> LENGTH: 339

<212> TYPE: DNA
<213> ORGANISM: Mus musculus

<400> SEQUENCE: 55

```
aacattatgc tgacacagtc gccatcatct ctggctgtgt ctgcaggaga aaaggtcact    60
atgagctgta gtccagtcaa agtgttttt ttcagttcaa gtcagaagaa ctacttggcc   120
tggtaccaac agataccagg gcagtctcct aaacttctga tctactgggc atccactagg   180
gaatctggtg tccctgatcg cttcacaggc agtggatctg ggacagattt tactcttacc   240
atcagcagtg tacaatctga agacctggca atttattact gtcatcaata cctctcctcg   300
cggacgttcg gtggaggcac caaactggaa atcaaacga                         339
```

<210> SEQ ID NO 56
<211> LENGTH: 354
<212> TYPE: DNA
<213> ORGANISM: Mus musculus

<400> SEQUENCE: 56

```
caggtgcaac tgcagcagcc tggggctgag gtggtgaagc ctggggcctc agtgaagatg    60
tcctgcaagg cttctggcta cacatttacc agttactata tacactggat aaagcagaca   120
cctggacagg gcctggaatg ggttggagtt atttatccag gaaatgatga tatttcctac   180
aatcagaagt tcaaaggcaa ggccacattg actgcagaca atcctccac acagcctac    240
atgcaactca gcagcctgac atctgaggac tctgcggtct attactgtgc aagagaggtt   300
cgtctacggt acttcgatgt ctggggcgca gggaccacgg tcaccgtctc ctca        354
```

<210> SEQ ID NO 57
<211> LENGTH: 17
<212> TYPE: PRT
<213> ORGANISM: Mus musculus

<400> SEQUENCE: 57

```
Val Ile Tyr Pro Gly Asn Asp Asp Ile Ser Tyr Asn Gln Lys Phe Lys
1               5                   10                  15

Gly
```

<210> SEQ ID NO 58
<211> LENGTH: 10
<212> TYPE: PRT
<213> ORGANISM: Mus musculus

<400> SEQUENCE: 58

```
Gly Tyr Thr Phe Thr Ser Tyr Tyr Ile His
1               5                   10
```

<210> SEQ ID NO 59
<211> LENGTH: 10
<212> TYPE: PRT
<213> ORGANISM: Mus musculus

<400> SEQUENCE: 59

```
Val Ile Tyr Pro Gly Asn Asp Asp Ile Ser
1               5                   10
```

<210> SEQ ID NO 60
<211> LENGTH: 99
<212> TYPE: PRT
<213> ORGANISM: Mus musculus

<400> SEQUENCE: 60

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser

<210> SEQ ID NO 61
<211> LENGTH: 96
<212> TYPE: PRT
<213> ORGANISM: Mus musculus

<400> SEQUENCE: 61

Val Gln Leu Gln Gln Pro Gly Ala Glu Leu Val Lys Pro Gly Ala Ser
1               5                   10                  15

Val Lys Val Ser Cys Lys Ala Ser Gly Tyr Thr Phe Thr Ser Tyr Trp
            20                  25                  30

Met His Trp Val Lys Gln Arg Pro Gly Gln Gly Leu Glu Trp Ile Gly
        35                  40                  45

Arg Ile His Pro Ser Asp Ser Asp Thr Asn Tyr Asn Gln Lys Phe Lys
50                  55                  60

Gly Lys Ala Thr Leu Thr Val Asp Lys Ser Ser Ser Thr Ala Tyr Met
65                  70                  75                  80

Gln Leu Ser Ser Leu Thr Ser Glu Asp Ser Ala Val Tyr Tyr Cys Ala
                85                  90                  95

<210> SEQ ID NO 62
<211> LENGTH: 114
<212> TYPE: PRT
<213> ORGANISM: Mus musculus

<400> SEQUENCE: 62

Asn Ile Met Leu Thr Gln Ser Pro Ser Ser Leu Ala Val Ser Ala Gly
1               5                   10                  15

Glu Lys Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Ile Tyr Tyr Cys His Gln
                85                  90                  95

Tyr Leu Ser Ser Arg Thr Phe Gly Gly Gly Thr Lys Leu Glu Ile Lys
                100                 105                 110

Arg Ala

-continued

<210> SEQ ID NO 63
<211> LENGTH: 115
<212> TYPE: PRT
<213> ORGANISM: Mus musculus

<400> SEQUENCE: 63

Asp Ile Val Met Ser Gln Ser Pro Ser Ser Leu Ala Val Ser Val Gly
1               5                   10                  15

Glu Lys Val Thr Met Thr Cys Lys Ser Ser Gln Ser Leu Leu Tyr Ser
            20                  25                  30

Ser Asn Gln Met Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Glu Ala Glu Asp Leu Ala Val Tyr Tyr Cys Gln Gln
                85                  90                  95

Tyr His Ser Tyr Pro Phe Thr Phe Gly Ser Gly Thr Lys Leu Glu Ile
            100                 105                 110

Lys Arg Ala
        115

<210> SEQ ID NO 64
<211> LENGTH: 115
<212> TYPE: PRT
<213> ORGANISM: Mus musculus

<400> SEQUENCE: 64

Asp Ile Val Met Thr Gln Ser Pro Ser Ser Leu Thr Val Thr Ala Gly
1               5                   10                  15

Glu Lys Val Thr Met Ser Cys Thr Ser Ser Gln Ser Leu Phe Asn Ser
            20                  25                  30

Gly Lys Gln Lys Asn Tyr Leu Thr Trp Tyr Gln Gln Lys Pro Gly Gln
        35                  40                  45

Pro Pro Lys Val Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Asn Pro Leu Thr Phe Gly Gly Gly Thr Lys Leu Glu Leu
            100                 105                 110

Lys Arg Ala
        115

<210> SEQ ID NO 65
<211> LENGTH: 115
<212> TYPE: PRT
<213> ORGANISM: Mus musculus

<400> SEQUENCE: 65

Asp Ile Val Met Thr Gln Ser Pro Ser Ser Leu Thr Val Thr Thr Gly
1               5                   10                  15

Glu Lys Val Thr Met Thr Cys Lys Ser Ser Gln Ser Leu Leu Asn Ser
            20                  25                  30

Gly Ala Gln Lys Asn Tyr Leu Thr Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Gly Val Gln Ala Glu Asp Leu Ala Val Tyr Tyr Cys Gln Asn
                85                  90                  95

Asn Tyr Asn Tyr Pro Leu Thr Phe Gly Ala Gly Thr Lys Leu Glu Leu
            100                 105                 110

Lys Arg Ala
    115

<210> SEQ ID NO 66
<211> LENGTH: 115
<212> TYPE: PRT
<213> ORGANISM: Mus musculus

<400> SEQUENCE: 66

Asp Ile Val Met Thr Gln Ser Pro Ser Ser Leu Thr Val Thr Thr Gly
1               5                   10                  15

Glu Lys Val Thr Met Thr Cys Lys Ser Ser Gln Ser Leu Leu Asn Ser
                20                  25                  30

Arg Thr Gln Lys Asn Tyr Leu Thr Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Gly Val Gln Ala Glu Asp Leu Ala Val Tyr Tyr Cys Gln Asn
                85                  90                  95

Asn Tyr Asn Tyr Pro Leu Thr Phe Gly Ala Gly Thr Lys Leu Glu Leu
            100                 105                 110

Lys Arg Ala
    115

<210> SEQ ID NO 67
<211> LENGTH: 115
<212> TYPE: PRT
<213> ORGANISM: Mus musculus

<400> SEQUENCE: 67

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Phe Asn Ser
                20                  25                  30

Gly Lys Arg Lys Asn Phe Leu Thr Trp Tyr His Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Val Gln Ala Glu Asp Leu Ala Ile Tyr Tyr Cys Gln Asn
                85                  90                  95

Asp Tyr Ser His Pro Leu Thr Phe Gly Ala Gly Thr Lys Leu Glu Leu
            100                 105                 110

Lys Arg Ala
    115

-continued

<210> SEQ ID NO 68
<211> LENGTH: 115
<212> TYPE: PRT
<213> ORGANISM: Mus musculus

<400> SEQUENCE: 68

Asp Ile Val Met Thr Gln Ser Pro Ser Ser Leu Ser Val Ser Ala Gly
1               5                   10                  15

Glu Arg Val Thr Met Ser Cys Lys Ser Ser Gln Ser Leu Leu Asn Ser
            20                  25                  30

Gly Asn Gln Lys Asn Phe Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Ile
            100                 105                 110

Lys Arg Ala
    115

<210> SEQ ID NO 69
<211> LENGTH: 113
<212> TYPE: PRT
<213> ORGANISM: Mus musculus

<400> SEQUENCE: 69

Asp Val Val Met Thr Gln Thr Pro Ser Ser Leu Ala Met Ser Val Gly
1               5                   10                  15

Gln Lys Val Thr Met Ser Cys Lys Ser Ser Gln Ser Leu Leu Asn Ile
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Gln Ala Asp Tyr Phe Cys Gln Gln
                85                  90                  95

His Tyr Arg Ala Pro Arg Thr Phe Gly Gly Gly Thr Lys Leu Glu Ile
            100                 105                 110

Lys

<210> SEQ ID NO 70
<211> LENGTH: 114
<212> TYPE: PRT
<213> ORGANISM: Mus musculus

<400> SEQUENCE: 70

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Tyr Leu Ala Trp Tyr Gln Gln Lys Pro Gly Gln

```
                35                  40                  45
Pro Pro Lys Leu Leu Ile Tyr Trp Ala Ser Thr Arg Glu Ser Gly Val
 50                  55                  60

Pro Asp Arg Phe Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Tyr Ser Phe Gly Gln Gly Thr Lys Leu Glu Ile
                100                 105                 110

Lys Arg

<210> SEQ ID NO 71
<211> LENGTH: 113
<212> TYPE: PRT
<213> ORGANISM: Mus musculus

<400> SEQUENCE: 71

Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
                 20                  25                  30

Gly Asn Gln Lys Asn Tyr Leu Thr Trp Tyr Gln Gln Lys Pro Gly Gln
                 35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Pro
                100                 105                 110

Gly

<210> SEQ ID NO 72
<211> LENGTH: 109
<212> TYPE: PRT
<213> ORGANISM: Mus musculus

<400> SEQUENCE: 72

Asp Ile Val Met Thr Gln Ser Pro Lys Phe Met Ser Thr Ser Val Gly
 1               5                  10                  15

Asp Arg Val Thr Ile Thr Cys Lys Ala Ser Gln Asp Val Ser Thr Ala
                 20                  25                  30

Val Val Trp Tyr Gln Gln Lys Pro Gly Gln Ser Pro Lys Leu Leu Ile
                 35                  40                  45

Tyr Trp Ala Ser Thr Arg His Ile Gly Val Pro Asp Arg Phe Ala Gly
 50                  55                  60

Ser Gly Ser Gly Thr Asp Tyr Thr Leu Thr Ile Ser Ser Val Gln Ala
 65                  70                  75                  80

Glu Asp Leu Ala Leu Tyr Tyr Cys Gln Gln His Tyr Ser Pro Pro Trp
                 85                  90                  95

Thr Phe Gly Gly Gly Thr Lys Leu Glu Ile Lys Arg Ala
                100                 105

<210> SEQ ID NO 73
<211> LENGTH: 117
```

```
<212> TYPE: PRT
<213> ORGANISM: Mus musculus

<400> SEQUENCE: 73

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
            100                 105                 110

Thr Val Thr Val Ser
            115

<210> SEQ ID NO 74
<211> LENGTH: 116
<212> TYPE: PRT
<213> ORGANISM: Mus musculus

<400> SEQUENCE: 74

Gln Ile Gln Leu Gln Gln Ser Gly Pro Glu Leu Val Arg Pro Gly Ala
1               5                   10                  15

Ser Val Lys Ile Ser Cys Lys Ala Ser Gly Tyr Thr Phe Thr Asp Tyr
            20                  25                  30

Tyr Ile His Trp Val Lys Gln Arg Pro Gly Glu Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Lys Phe Ala Met Asp Tyr Trp Gly Gln Gly Thr Ser
            100                 105                 110

Val Thr Val Ser
            115

<210> SEQ ID NO 75
<211> LENGTH: 119
<212> TYPE: PRT
<213> ORGANISM: Mus musculus

<400> SEQUENCE: 75

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Met Lys Gln Lys Pro Gly Gln Gly Leu Glu Trp Ile
        35                  40                  45

Gly Trp Ile Asp Pro Gly Ser Gly Asn Thr Lys Tyr Asn Glu Lys Phe
```

```
                    50                  55                  60
Lys Gly Lys Ala Thr Leu Thr Val Asp Thr Ser Ser Ser Thr Ala Tyr
 65                  70                  75                  80

Met Gln Leu Ser Ser Leu Thr Ser Glu Asp Thr Ala Val Tyr Phe Cys
                     85                  90                  95

Ala Arg Glu Lys Thr Thr Tyr Tyr Tyr Ala Met Asp Tyr Trp Gly Gln
                100                 105                 110

Gly Thr Ser Val Thr Val Ser
            115
```

<210> SEQ ID NO 76
<211> LENGTH: 118
<212> TYPE: PRT
<213> ORGANISM: Mus musculus

<400> SEQUENCE: 76

```
Gln Gly Gln Leu Gln Gln Ser Gly Ala Glu Leu Val Arg Pro Gly Ser
 1               5                  10                  15

Ser Val Lys Ile Ser Cys Lys Ala Ser Gly Tyr Ala Phe Ser Ser Phe
                20                  25                  30

Trp Val Asn Trp Val Lys Gln Arg Pro Gly Gln Gly Leu Glu Trp Ile
            35                  40                  45

Gly Gln Ile Tyr Pro Gly Asp Gly Asp Asn Lys Tyr Asn Gly Lys Phe
        50                  55                  60

Lys Gly Lys Ala Thr Leu Thr Ala Asp Lys Ser Ser Thr Thr Ala Tyr
 65                  70                  75                  80

Met Gln Leu Tyr Ser Leu Thr Ser Glu Asp Ser Ala Val Tyr Phe Cys
                 85                  90                  95

Ala Arg Ser Gly Asn Tyr Pro Tyr Ala Met Asp Tyr Trp Gly Gln Gly
                100                 105                 110

Thr Ser Val Thr Val Ser
            115
```

<210> SEQ ID NO 77
<211> LENGTH: 113
<212> TYPE: PRT
<213> ORGANISM: Mus musculus

<400> SEQUENCE: 77

```
Val Lys Leu Gln Glu Ser Gly Ala Glu Leu Ala Arg Pro Gly Ala Ser
 1               5                  10                  15

Val Lys Met Ser Cys Lys Ala Ser Gly Tyr Thr Phe Thr Tyr Thr
                20                  25                  30

Ile His Trp Ile Lys Gln Arg Pro Gly Gln Gly Leu Glu Trp Ile Gly
            35                  40                  45

Tyr Ile Asn Pro Ser Ser Val Tyr Thr Asn Tyr Asn Gln Arg Phe Lys
        50                  55                  60

Asp Lys Ala Thr Leu Thr Arg Asp Arg Ser Ser Asn Thr Ala Asn Ile
 65                  70                  75                  80

His Leu Ser Ser Leu Thr Ser Asp Asp Ser Ala Val Tyr Tyr Cys Val
                 85                  90                  95

Arg Glu Gly Glu Val Pro Tyr Trp Gly Gln Gly Thr Thr Val Thr Val
                100                 105                 110

Ser
```

<210> SEQ ID NO 78

<211> LENGTH: 113
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: "X" may be any amino acid

<400> SEQUENCE: 78

```
Xaa Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Ala Lys Gln Lys Pro Glu Gln Gly Leu Glu Trp Ile
        35                  40                  45

Gly Tyr Ile Ser Pro Gly Asn Asp Asp Ile Lys Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Asn Ser Leu Thr Ser Glu Asp Ser Ala Val Tyr Phe Cys
                85                  90                  95

Lys Arg Ser Tyr Tyr Gly His Trp Gly Gln Gly Thr Thr Leu Thr Val
                100                 105                 110

Ser
```

<210> SEQ ID NO 79
<211> LENGTH: 118
<212> TYPE: PRT
<213> ORGANISM: Mus musculus

<400> SEQUENCE: 79

```
Val Gln Leu Gln Gln Ser Gly Ala Glu Leu Val Lys Pro Gly Ala Ser
1               5                   10                  15

Val Lys Leu Ser Cys Lys Ala Ser Gly Tyr Thr Phe Thr Ser Tyr Trp
            20                  25                  30

Met His Trp Val Lys Gln Arg Pro Gly Arg Gly Leu Glu Trp Ile Gly
        35                  40                  45

Arg Ile Asp Pro Asn Ser Gly Gly Thr Lys Tyr Asn Glu Lys Phe Lys
    50                  55                  60

Ser Lys Ala Thr Leu Thr Val Asp Lys Pro Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Tyr Asp Tyr Tyr Gly Ser Ser Tyr Phe Asp Tyr Trp Gly Gln Gly
                100                 105                 110

Thr Thr Val Thr Val Ser
        115
```

<210> SEQ ID NO 80
<211> LENGTH: 114
<212> TYPE: PRT
<213> ORGANISM: Mus musculus

<400> SEQUENCE: 80

```
Gln Leu Gln Gln Ser Gly Thr Val Leu Ala Arg Pro Gly Ala Ser Val
1               5                   10                  15

Lys Met Ser Cys Lys Ala Ser Gly Tyr Ser Phe Thr Arg Tyr Trp Met
            20                  25                  30
```

```
His Trp Ile Lys Gln Arg Pro Gly Gln Gly Leu Glu Trp Ile Gly Ala
            35                  40                  45

Ile Tyr Pro Gly Asn Ser Asp Thr Ser Tyr Asn Gln Lys Phe Glu Gly
 50                  55                  60

Lys Ala Lys Leu Thr Ala Val Thr Ser Ala Ser Thr Ala Tyr Met Glu
 65                  70                  75                  80

Leu Ser Ser Leu Thr His Glu Asp Ser Ala Val Tyr Tyr Cys Ser Arg
                 85                  90                  95

Asp Tyr Gly Tyr Tyr Phe Asp Phe Trp Gly Gln Gly Thr Thr Leu Thr
             100                 105                 110

Val Ser

<210> SEQ ID NO 81
<211> LENGTH: 116
<212> TYPE: PRT
<213> ORGANISM: Mus musculus

<400> SEQUENCE: 81

Glu Val Gln Leu Gln Gln Ser Gly Pro Asp Leu Val Lys Pro Gly Ala
  1               5                  10                  15

Ser Val Lys Ile Ser Cys Lys Ala Ser Gly Tyr Ser Phe Ser Thr Tyr
             20                  25                  30

Tyr Met His Trp Val Lys Gln Ser His Gly Lys Ser Leu Glu Trp Ile
         35                  40                  45

Gly Arg Val Asp Pro Asp Asn Gly Gly Thr Ser Phe Asn Gln Lys Phe
 50                  55                  60

Lys Gly Lys Ala Ile Leu Thr Val Asp Lys Ser Ser Thr Ala Tyr
 65                  70                  75                  80

Met Glu Leu Gly Ser Leu Thr Ser Glu Asp Ser Ala Val Tyr Tyr Cys
                 85                  90                  95

Ala Arg Arg Asp Asp Tyr Tyr Phe Asp Phe Trp Gly Gln Gly Thr Ser
             100                 105                 110

Leu Thr Val Ser
         115

<210> SEQ ID NO 82
<211> LENGTH: 119
<212> TYPE: PRT
<213> ORGANISM: Mus musculus

<400> SEQUENCE: 82

Gln Val Gln Leu Gln Gln Ser Gly Ala Glu Leu Met Lys Pro Gly Ala
  1               5                  10                  15

Ser Val Lys Ile Ser Cys Lys Ala Thr Gly Tyr Thr Phe Ser Ser Phe
             20                  25                  30

Trp Ile Glu Trp Val Lys Gln Arg Pro Gly His Gly Leu Glu Trp Ile
         35                  40                  45

Gly Glu Ile Leu Pro Gly Ser Gly Gly Thr His Tyr Asn Glu Lys Phe
 50                  55                  60

Lys Gly Lys Ala Thr Phe Thr Ala Asp Lys Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly His Ser Tyr Tyr Phe Tyr Asp Gly Asp Tyr Trp Gly Gln
             100                 105                 110

Gly Thr Ser Val Thr Val Ser
```

<210> SEQ ID NO 83
<211> LENGTH: 123
<212> TYPE: PRT
<213> ORGANISM: Mus musculus

<400> SEQUENCE: 83

Gln Val Gln Leu Gln Gln Ser Gly Ala Glu Leu Val Arg Ala Gly Ser
1               5                   10                  15

Ser Val Lys Met Ser Cys Lys Ala Ser Gly Tyr Thr Phe Thr Ser Tyr
            20                  25                  30

Gly Val Asn Trp Val Lys Gln Arg Pro Gly Gln Gly Leu Glu Trp Ile
        35                  40                  45

Gly Tyr Ile Asn Pro Gly Lys Gly Tyr Leu Ser Tyr Asn Glu Lys Phe
    50                  55                  60

Lys Gly Lys Thr Thr Leu Thr Val Asp Arg Ser Ser Ser Thr Ala Tyr
65                  70                  75                  80

Met Gln Leu Arg Ser Leu Thr Ser Glu Asp Ala Ala Val Tyr Phe Cys
                85                  90                  95

Ala Arg Ser Phe Tyr Gly Gly Ser Asp Leu Ala Val Tyr Tyr Phe Asp
            100                 105                 110

Ser Trp Gly Gln Gly Thr Thr Leu Thr Val Ser
        115                 120

<210> SEQ ID NO 84
<211> LENGTH: 21
<212> TYPE: PRT
<213> ORGANISM: Homo sapien

<400> SEQUENCE: 84

Asn Met Thr Ser Ala Lys Pro Gly Gln Lys Gly Asp Ser Asp Ser Glu
1               5                   10                  15

Gly Lys Lys Arg Ala
            20

<210> SEQ ID NO 85
<211> LENGTH: 21
<212> TYPE: PRT
<213> ORGANISM: Homo sapien

<400> SEQUENCE: 85

Asp Gln Thr Ser Val Arg Pro Gly Glu Lys Gly Ser Ser Asp Pro Glu
1               5                   10                  15

Gly Lys Lys Arg Thr
            20

<210> SEQ ID NO 86
<211> LENGTH: 20
<212> TYPE: PRT
<213> ORGANISM: Homo sapien

<400> SEQUENCE: 86

Asp Val Thr Ser Val Arg Pro Gly Lys Lys Gly Ser Ser Asp Pro Glu
1               5                   10                  15

Gly Lys Lys Arg
            20

<210> SEQ ID NO 87
<211> LENGTH: 21

```
<212> TYPE: PRT
<213> ORGANISM: Homo sapien

<400> SEQUENCE: 87

Asp Gln Thr Ser Val Arg Pro Gly Lys Gly Ser Ser Asp Pro Glu
1               5                   10                  15

Gln Lys Lys Arg Thr
            20

<210> SEQ ID NO 88
<211> LENGTH: 20
<212> TYPE: PRT
<213> ORGANISM: Homo sapien

<400> SEQUENCE: 88

Glu Val Thr Gly Pro Arg Pro Gly Gln Arg Gly Asp Ser Asp Pro Glu
1               5                   10                  15

Gln Lys Lys Arg
            20

<210> SEQ ID NO 89
<211> LENGTH: 20
<212> TYPE: PRT
<213> ORGANISM: Homo sapien

<400> SEQUENCE: 89

Asp Val Thr Leu Leu Pro Pro Gly Gln Arg Gly Asp Ala Asp Ala Glu
1               5                   10                  15

Gln Lys Lys Arg
            20

<210> SEQ ID NO 90
<211> LENGTH: 24
<212> TYPE: PRT
<213> ORGANISM: Homo sapien

<400> SEQUENCE: 90

Gln Gln Ala Val Lys Pro Gly Lys Gly Thr Pro Gly Gln Gln Lys Lys
1               5                   10                  15

Gly Lys Ser Ser Ser Glu Ala Ser
            20

<210> SEQ ID NO 91
<211> LENGTH: 24
<212> TYPE: PRT
<213> ORGANISM: Homo sapien

<400> SEQUENCE: 91

Gln Gln Ala Val Lys Pro Gly Lys Gly Thr Pro Gly Gln Gln Lys Gln
1               5                   10                  15

Gly Thr Pro Ser Ser Glu Lys Ser
            20

<210> SEQ ID NO 92
<211> LENGTH: 24
<212> TYPE: PRT
<213> ORGANISM: Homo sapien

<400> SEQUENCE: 92

Gln Gln Ala Ala Lys Pro Gly Lys Gly Thr Pro Gly Gln Gln Lys Gln
1               5                   10                  15

Gly Gly Ser Ser Ser Glu Gln Ser
```

```
<210> SEQ ID NO 93
<211> LENGTH: 24
<212> TYPE: PRT
<213> ORGANISM: Homo sapien

<400> SEQUENCE: 93

Gln Gln Ala Val Lys Pro Gly Lys Gly Thr Pro Gly Gln Gln Lys Gln
1               5                   10                  15

Gly Thr Ser Ser Ser Glu Gln Ser
            20

<210> SEQ ID NO 94
<211> LENGTH: 23
<212> TYPE: PRT
<213> ORGANISM: Homo sapien

<400> SEQUENCE: 94

Gln Ala Val Lys Pro Gly Lys Gly Thr Pro Gly Gln Gln Lys Gln Gly
1               5                   10                  15

Lys Ser Ser Ser Glu Gln Ser
            20

<210> SEQ ID NO 95
<211> LENGTH: 113
<212> TYPE: PRT
<213> ORGANISM: Mus musculus

<400> SEQUENCE: 95

Asn Ile Met Leu Thr Gln Ser Pro Ser Ser Leu Ala Val Ser Ala Gly
1               5                   10                  15

Glu Lys Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ser Glu Asp Leu Ala Ile Tyr Tyr Cys His Gln
                85                  90                  95

Tyr Leu Ser Ser Arg Thr Phe Gly Gly Gly Thr Lys Leu Glu Ile Lys
            100                 105                 110

Arg

<210> SEQ ID NO 96
<211> LENGTH: 118
<212> TYPE: PRT
<213> ORGANISM: Mus musculus

<400> SEQUENCE: 96

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Tyr Ile His Trp Ile Lys Gln Thr Pro Gly Gln Gly Leu Glu Trp Val
        35                  40                  45

Gly Val Ile Tyr Pro Gly Asn Asp Asp Ile Ser Tyr Asn Gln Lys Phe
```

-continued

```
            50                  55                  60
Lys Gly Lys Ala Thr Leu Thr Ala Asp Lys Ser Ser Thr Ala Tyr
65                      70                  75                  80

Met Gln Leu Ser Ser Leu Thr Ser Glu Asp Ser Ala Val Tyr Tyr Cys
                85                  90                  95

Ala Arg Glu Val Arg Leu Arg Tyr Phe Asp Val Trp Gly Ala Gly Thr
                100                 105                 110

Thr Val Thr Val Ser Ser
        115
```